(12) United States Patent
Stauderman et al.

(10) Patent No.: US 8,507,269 B2
(45) Date of Patent: Aug. 13, 2013

(54) CALCIUM CHANNEL PROTEINS AND USES THEREOF

(75) Inventors: Kenneth A. Stauderman, San Diego, CA (US); Jack Roos, San Diego, CA (US); Gonul Velicelebi, San Diego, CA (US)

(73) Assignee: CalciMedica, Inc., La Jolla, CA (US)

( * ) Notice: Subject to any disclaimer, the term of this patent is extended or adjusted under 35 U.S.C. 154(b) by 565 days.

(21) Appl. No.: 12/127,729

(22) Filed: May 27, 2008

(65) Prior Publication Data
US 2008/0293092 A1 Nov. 27, 2008

Related U.S. Application Data

(60) Provisional application No. 60/939,922, filed on May 24, 2007.

(51) Int. Cl.
*C12N 5/00* (2006.01)
(52) U.S. Cl.
USPC .......................................... 435/325; 435/465
(58) Field of Classification Search
USPC .................................................. 435/325, 465
See application file for complete search history.

(56) References Cited

U.S. PATENT DOCUMENTS

| | | | |
|---|---|---|---|
| 6,875,581 | B1 | 4/2005 | Voelkel |
| 2002/0034728 | A1 | 3/2002 | Normant |
| 2005/0107588 | A1 | 5/2005 | Duggan |
| 2006/0134663 | A1 | 6/2006 | Harkin |
| 2007/0031814 | A1 | 2/2007 | Roos |
| 2007/0099251 | A1 | 5/2007 | Zhang |
| 2008/0039392 | A1 | 2/2008 | Cahalan |
| 2008/0096227 | A1 | 4/2008 | Penner |
| 2008/0293092 | A1 | 11/2008 | Stauderman |
| 2009/0178146 | A1 | 7/2009 | Rao et al. |
| 2011/0269174 | A1 | 11/2011 | Rao et al. |

FOREIGN PATENT DOCUMENTS

| | | |
|---|---|---|
| EP | 0976823 A | 2/2000 |
| WO | WO-99-32619 | 7/1999 |
| WO | WO-02-30976 | 4/2002 |
| WO | WO-2005-016962 | 2/2005 |
| WO | WO-2007-081804 | 7/2007 |
| WO | WO-2007-139926 A2 | 12/2007 |

OTHER PUBLICATIONS

Peinelt et al. "Amplification of CRAC current by STIM1 and CRACM1 (Orai1)", Nature Cell Biology, 2006, 8(7):771-773.*
Soboloff et al. "Orai1 and STIM reconstitute store-operated calcium channel function", JBC, 2006, 281(30):20661-20665.*
Mercer et al. "Large store-operated calcium selective currents due to co-expression of Orai1 or Orai2 with the intracullar calcium sensor, Stim1" JBC, 2006, 281(34):24979-24990.*
Roos et al. "STIM1, an essential and conxerved component of store-operated Ca2+ channel function", JCB, 2005, 169(3):435-445.*
Vig et al. "CRACM1 is a plasma membrane protein essential fro store-operated Ca2+ entry", Science, 2006, 312:1220-1222.*
Kuhns, D.B. et al., "Ca2+-dependent production and release of IL-8 in human neutrophils," J. Immunol. 161:4332-4339 (1998).
Lorin-Nebel, C. et al., "CRAC channel activity in *C. elegans* is mediated by orai 1 and STIM 1 homologues and is essential for ovulation and fertility," J. Physiol. 580:67-85 (2007).
Smyth, J.T. et al., "Emerging perspectives in store-operated Ca2+ entry: Roles of Orai, Stim and TRP," Biochimica et Biophysica Acta 1763:1147-1160 (2006).
Soboloff, J. et al., "Calcium signals mediated by STIM and Orai proteins-a new pardigm in inter-organelle communication," Biochimica et Biophysica Acta 1763:1161-1168 (2006).
PCT/US08/64915 Search Report dated Aug. 1, 2008.
Abbas et al., 2005, computer printout pp. 2-6.
Abecasis, G. R. et al., "Merlin-rapid analysis of dense genetic maps using sparse gene low trees." Nature Genetics 30:97-101, 2002.
Altshuler, D. et al., "A haplotype map of the human genome." Nature 437(7063):1299-1320, 2005.
Aramburu, J. et al., "Affinity-Driven Peptide Selection of an NFAT Inhibitor More Selective Than Cyclosporin A." Science 285:2129-2133, 1999.
Arnaudeau et al., "Calreticulin differentially modulates calcium uptake and release in the endoplasmic reticulum and mitochondria," J. Biol. Chem. 29:277(48):46696-46705 (2002).
Badou, A. et al., "Requirement of Voltage-Gated Calcium Channel 14 Subunit for T Lymphocyte Functions." Science 307:117-121, 2005.
Beals, C. R. et al., "Nuclear Export of NF-ATc Enhanced by Glycogen Synthase Kinase-3." Science 275:1930-1933, 1997.
CA 2,688,417 Office Action dated Sep. 19, 2011.
Cahill, J., "Protein and antibody arrays and their medical applications," Immunol. Meth. 250:81-91 (2001).
Chan et al., "Structural characteristics that govern binding to, and modulation through, the cardiac ryanodine receptor nucleotide binding site," Mol. Pharmacol. 63(1):174-182 (2003).
Chattopadhyay et al., " Effect of single amino acid mutations in the conserved GDNQ motif of L protein of Rinderpest virus on RNA synthesis in vitro and in vivo," Virus Research 99(2):139-145 (2004).
Chen et al., TH1 and TH2 cytokine inhibition by 3,5-bis(trifluoromethyl)pyrazoles, a novel class of immunomodulators, Cell Immunol. 2002, vol. 220 pp. 134-142.
Churchill and Louis, "Imaging of intracellular calcium stores in single permeabilized lens cells," Am. J. Physiol. 276(2 Pt 1):C426-434 (1999).
Clemens et al,, "Use of double-stranded RNA interference in Drosophila cell lines to dissect signal transduction pathways," PNAS USA 97:6499-6503 (2000).
Clipstone, N. A. et al., "Molecular Analysis of the Interaction of Calcineurin with Drug-Immunophilin Complexes." J. Biol Chem 269(42):26431-26437, 1994.
Correa et al., "Structural determinants of adenophostin A activity at inositol trisphosphate receptors," Mol. Pharmacol. 59(5):1206-1215 (2001).
Courtois, G. et al., "A hypermorphic I-kappa-B-beta mutation is associated with autosomal dominant anhidrotic ectodermal dysplasia and T cell immunodeficiency." J. Clin Invest 112:1108-1115, 2003.

(Continued)

*Primary Examiner* — Bin Shen
(74) *Attorney, Agent, or Firm* — Wilson, Sonsini, Goodrich & Rosati

(57) ABSTRACT

Described herein are compositions and uses thereof related to $Ca^{2+}$ release-activated $Ca^{2+}$ (CRAC) channel activity. Also described herein CRAC channel modulators for treating diseases or conditions that would benefit from inhibition of SOC channel activity.

7 Claims, 11 Drawing Sheets

(56) References Cited

OTHER PUBLICATIONS

Crabtree, G. R. and Olson, E. N., "NFAT Signaling: Choreographing the Social Lives of Cells." Cell 109:S67-S79, 2002.
Cui, J. et al., "CaT1 Contributes to the Stores-operated Calcium Current in Jurkat T-lymphocytes." J. Biol. Chem 277 (49)47175-47183, 2002.
Doffinger, R. et al., "X-linked anhidrotic ectodermal dysplasia with immunodeficiency is caused by impaired NF- kappa-B signaling." Nature Genetics 27:277-285, 2001.
Duggan at al., US-495-148-92, computer printout pp. 11-14.(2004).
Eck et al., 1996, Goodman & Gilman's The Pharmacological Basis of Therapeutics, McGraw-Hill, New York, p. 77-101.
Ellinor et al. (1995) "$Ca^{2+}$ channel selectivity at a single locus for high-affinity $Ca^{2+}$ interactions." *Neuron*, 15(5): 1121-1132.
EP 08756325 Examination Report dated Apr. 4, 2012.
EP 08756325 Search Report and Written Opinion mailed May 25, 2010.
Eroshkin et al., "Algorithm and computer program Pro_Anal for analysis of relationship between structure and activity in a family of proteins or peptides," Comput. Appl. Biosei. 9:491-497 (1993).
Fagan et al. "Regulation of the Ca2+-inhibitable adenylyl cyclase type VI by capacitative Ca2+ entry requires localization in cholesterol-rich domains," *J. Biol Chem*. Aug. 25, 2000;275(34):26530-7.
Fanger et al., "Characterization of T cell mutants with defects in capacitative calcium entry: genetic evidence for the physiological roles of CRAC channels," J. Cell Biol. 131:655-657 (1995).
Feske et al., "A Mutation in Orai1 Causes Immune Defifiency by Abrogating CRAC Channel Function" Native 441:179-185 (2006).
Feske, S. et al., "A severe defect in CRAC Ca2+ channel activation and altered K+ channel gating in T cells from immunodefieient patients." JEM 202(5):651-662, 2005.
Feske, S. et al., "Ca2+/calcineurin signalling in cells of the immune system," Biochemical and Biophysical Research Communications 311:1117-1132, 2003.
Feske, S. et al., "Gene regulation mediated by calcium signals in T lymphocytes." Nature Immunology 2(4):316-324, 2001.
Feske, S. et al., "The Duration of Nuclear Residence of NFAT Determines the Pattern of Cytokine Expression in Human SCID T Cells." J. Immunol 165:297-305, 2000.
Gabriel, S. B. et al., "The Structure of Haplotype Blocks in the Human Genome." Science 296:2225-2229, 2002.
Gallo et al. (2006) "Lymphocyte calcium signaling from membrane to nucleus," *Nature Immunology*, 7(1):25-32.
Gorecki, D., 2001, Expert Opin. Emerging Drugs, 6(2): 187-198.
Gudbjartsson, D. F. et al., "Allegro, a new computer program for multipoint linkage analysis." Nature Genetics 25:12-13, 2000.
Gwack, Y. et al., "A genome-wide Drosophila RNAi screen identifies DYRK-family kinases as regulators of NFAT." Nature 441:646-650, 2006.
Hanes and Pluckthin, "In vitro selection and evolution of functional proteins by using ribosome display," PNAS USA 13:4937-4942 (1997).
Hermosura, M. C. et al., "Dissociation of the store-operated calcium current Icrac and the Mg-nucleotide-regulated metal ion current MagNuM." J Physiol 539(2):445-458, 2002.
Hess and Tsien (1984) "Mechanism of ion permeation through calcium channels." Nature, 309: 453-456.
Hogan, P. G. et al., "Transcriptional regulation by calcium, caleineurin, and NFAT." Genes & Dev 17:2205-2232, 2003.
Horsley, V. and Pavlath, G. K., "NFAT: ubiquitous regulator of cell differentiation and adapation." J Cell Biol 156 (5):711-774, 2002.
Hoth et al. (1992) "Depletion of intracellular calcium stores activates a calcium current in mast cells." *Nature*, 355: 353-356.
Im, S. and Rao, A., "Activation and Deactivation of Gene Expression by Ca2+/Calcineurin-NFAT-mediated Signaling." Mol Cells 18(1):1-9, 2004.
Kall, L. et al., "A Combined Transmembrane Topology and Signal Peptide Prediction Method." J Mol Bio1338:1027-1036, 2004.

Kanno, T. and Siebenlist, U., "Activation of Nuclear Factor-kappa-B via T Cell Receptor Requires a Raf Kniase and Ca2+ Influx." J Immunol 157:5277-5283, 1996.
Karvonen et al., "Psoriasis and altered calcium metabolism: downregulated capacitative calcium influx and defective calcium-mediated cell signaling in cultured psoriatic keratinocytes," J. invest. Dermatol. 114:693-700 (2000).
Kim, E. and Sheng, M., "PDZ Domain Proteins of Synapses," Nature Reviews Neuroscience 5:771-781, 2004.
Kodama et al., 2006, Current Medicinal Chemistry, vol. 13, p. 2155-2161.
Kol et al., "Tumor cell growth arrest caused by subchromosomal transferable DNA fragments from chromosome 11," Science 260:361-364 (1993).
Kotturi, M. F. et al., "Identification and Functional Characterization of Voltage-dependent Calcium Channels in T Lymphocytes." J Biol Chem 278(47):46949-46960, 2003.
Kozak et al. "Distinct properties of CRAC and MIC chamiels in RBL cells." *The Journal of General Physiology*, 120(2): 221-235. (2002).
Krogh, A. et al., "Predicting Transmembrane Protein Topology with a Hidden Markov Model: Application to Complete Genomes," J Mol Biol 305:567-580, 2001.
Le Deist, F. et al., "A primary T-cell immunodeficiency associated with defective transmembrane calcium influx." Blood 85:1053-1062, 1995.
Lepple-Wienhues, A. and Cahalan, M. D., "Conductance and Permeation of Monovalent Cations through Depletion-Activated Ca2+ Channels (Icrac) in Jurkat T Cells." Biophysical Journal 71:787-794, 1996.
Lewis, R. S., "Calcium Signaling Mechanisms in T Lymphocytes," Annu Rev Immunol 19:497-521, 2001.
Leykin, I. et al., "Comparative linkage analysis and visualization of high-density oligonucleotide SNP array data." BMC Genetics 6(7):1-16, 2005.
Liou, J. et al., "STIM Is a Ca2+ Sensor Essential for Ca2-+-Store-Depletion-Triggered Ca2+ Influx." Current Biology 15:1235-1241, 2005.
Liu, J., "FK506 and cyclosporin, molecular probes for studying intracellular signal transduction," Immunology Today 14 (6):290-295, 1993.
Macian et al., "Transcriptional mechanisms underlying lymphocyte tolerance," *Cell*, Jun. 14, 2002;109(6)719-31.
Macian, F "Partners in transcription: NFAT and AP-1." Oncogene 20:2476-2489, 2001.
Macian, F "NFAT Proteins: Key Regulators of T-Cell Development and Function," Nature 5:472-484, 2005.
Markianos, K. et al., "Efficient Multipoint Linkage Analysis through Reduction of Inheritance Space." Am J Hum Genet 68:963-977, 2001.
Martin et al., "Relation between phosphatidylserine exposure and store-operated Ca2+ entry in stimulated cells," Biochem. Biophys. Res. Commun. 279:639-645 (2000).
Martinez et al., "Significance of capacitative Ca entry in the regulation of phosphatidylserine expression at the surface of stimulated cells," Biochem. 38:10092-10098(1999).
Mercer et al., "Large Store-operated Calcium Selective Currents Due to Co-expression of Orai1 or Orai2 with the Intracellular Calcium Sensor, Stim1," Journ. Biol. Chemc, vol. 281, No. 34, pp. 24979-24990, XP002506223, (2006).
Michalak et al., "Ca2+ signaling and calcium binding chaperones of the endoplasmic reticulum," Cell Calcium 32:269-278 (2002).
Minta et al., "Fluorescent indicators for cytosolic calcium based on Rhodamine and Fluorescein chromphores," J. Biol. Chem. 264(14):8171-8178 (1989).
Miyawaki et al., "Fluorescent indicators for Ca2+ based on green fluorescent proteins and calmodulin," *Nature*, Aug. 28, 1997;388(6645):882-7.
Mori, Y. et al., "Transient Receptor Potential 1 Regulates Capacitative Ca2+ Entry and Ca2+ Release from Endoplasmic Reticulum in B Lymphocytes." J Exp Med 195(6):673-681, 2002.
Myers, E. W. et al., "A Whole-Genome Assembly of Drosophila." Science 287:2196-2204, 2000.

Ng and Henikoff, "Predicting deleterious amino acid substitutions," Genome Res, 11(5):863-874 (2001).
Nishikawa et al., 2001, Human Gene Therapy, vol. 12, p. 861-870.
Nunez et al., "Cell proliferation depends on mitochondrial Ca2+ uptake: inhibition by salicylate," *J Physiol.* Feb. 15, 2006:571(Pt 1):57-73. Epub Dec. 8, 2005.
Okamura, H. et al., "Concerted Dephosphorylation of the Transcription Factor NFAT1 Induces a Conformational Switch that Regulates Transcriptional Activity." Molecular Cell 6:539-550, 2000.
Okamura, H. et al., "A Conserved Docking Motif for CK1 Binding Controls the Nuclear Localization of NFAT1." Molecular and Cellular Biology 24(10):4184-4195, 2004.
Oritani and Kincade, "Identification of stromal cell products that interact with pre-B cells," J. Cell Biol. 134:771-782 (1996).
Pan et al., 1997, Biochemical and Biophysical Research Communications, vol. 240, p. 314-323.
Parekh, A. B. and Penner, R., "Store Depletion and Calcium Influx." Physiological Reviews 77(4):901-930, 1997.
Parekh, A. B. and Putney, Jr., J. W., "Store-Operated Calcium Channels" Physiol Rev 85:757-810, 2005.
Parekh, A,B., "Cell Biology: Cracking the calcium entry code," Nature 441(11):163165 (2006).
Partiseti, M. et al., "The Calcium Current Activated by T Cell Receptor and Store Depletion in Human Lymphocytes Is Absent in a Primary Immunodeficiency." J Biol Chem 269(51):32327-32335, 1994.
PCT/US2007/000280 International Search Report dated Jan. 18, 2008.
Peinelt et al., "Amplification of CRAC current by STIM1 and CRACM1 (Orai1);" Nature Cell Biology, vol. 8, No. 7, pp. 771-773, XP-002489913 (2006)
Petersen et al., "The role of endplasmic reticulum calcium pumps during cytosolic calcium spiking; in pancreatic acinar cells," J. Biol. Chem. 268(30):22262-22264 (1993).
Philipp, S. et aL, "TRPC3 Mediates T-cell Receptor-dependent Calcium Entry in Human T-lymphocytes." J Biol Chem 278(29):26629-26638, 2003.
Prakriya and Lewis (2001) "Potentiation and inhibition of $Ca^{2+}$ release-activated $Ca^{2+}$ channels by 2-am inoethyldiphenyl borate (2-APB) occurs independently of $IP_3$ receptors." *Journal of Physiology*, 536(1): 3-19.
Prakriya et al. (2006) "Orai1 is an essential pore subunit of the CRAC channel." *Nature,* 443: 230-233.
Prakriya, M. and Lewis, R. S., "Separation and Characterization of Currents through Store-operated CRAC Channels and Mg2+-inhibited Cation (MIC) Channels." J Gen Physiol 119(5):487-508, 2002.
Prakriya, M. and Lewis, R. S., "CRAC channels: activation, permeation, and the search for a molecular identity." Cell Calcium 33:311-321, 2003.
Puel, A. et al., "Inherited disorders of NF-kappa-B-mediated immunity in man." Current Opinion in Immunology 16:34-41, 2004.
Putney et al., "A model for receptor-regulated calcium entry," *Cell Calcium.* Feb. 1986;7(1):1-12.
Putney et al., "New Molecular Players in capacitative $Ca^{2+}$Entry," Journ. Cell Science, 120(Pt. 12) pp. 1959-1969 (2007).
Putney et al., "Recent breakthroughs in the molecular mechanism of capacitative calcium entry (with thoughts o how we got here)," Cell Calcium 42(2):103-110 (2007).
Putney et al., "The signal for capacitative calcium entry," *Cell.* Oct. 22, 1993;75(2):199-201.
Rao et al., "Transcription factors of the NFAT family: regulation and function," *Annu Rev Immunol.* 1997;15:707-47.
Robinson, L.C, and Marchant, J.S., "Calcium Influx: Beyond 'Current' Biology," Current Biology 16(14):R548-550 (2006).
Roderick, H. L. and Bootman, M. D., "Calcium Influx: Is Homer the Missing Link?" Current Biology 13:R976-R978, 2003.
Rodi et al., "One from col. A and two from col. B: the benefits of phage display in molecular-recognition studies," Curr. Capin. Chem. Biol. 6:92-96 (2002).
Roos, J. et al., "STIM1, an essential and conserved component of store-operated Ca2+ channel function." J Cell Biol 169(3):435-445, 2005.
Rubinson et al., "A lentivirus-based system to functionally silence genes in primary mammalian cells, stem cells and transgenic mice by RNA interference," Nature Genet. 33:401-406(2003) and Corrigendum, vol. 39(6):803 (2007).
Rudensky et al., "FOXP3 and NFAT: partners in tolerance," *Cell.* Jul. 28, 2006;126(2):253-6.
Salazar, C. and Hofer, T., "Allosteric Regulation of the Transcription Factor NFAT1 by Multiple Phosphorylation Sites: A Mathematical Analysis." J. Mol. Biol. 327:31-45, 2003.
Salazar, C. et al., "Activation of the Transcription Factor NFAT1: concerted or modular regulation?" FEBS Lett 579:621-626, 2005.
Schmidt-Ulrich, R. et al., "Requirement of NF-kappa-B/Rel for the development of hair follicles and other epidermal appendices." Development 128:3843-3853, 2001.
SIFT Algorithm, http://blocks.fherc.org/sift/SIFT.html, printed on Jul. 24, 2008.
Skolnick, et al., "From genes to protein structure and function: novel applications of computational approaches in the genomic era," Trends in Biotechnology 18(1)34-9 (2000).
Smahi, A. et al., "The NF-kappa-B signalling ptahway in human diseases: from incontinentia pigmenti to ectodermal dysplasias and immune-deficiency syndromes." Human Molecular Genetics 11(20):2371-2375, 2002.
Smallwood et al., "Different substitutions at conserved amino acids in domains II and III in the Sendia L RNA polymerase protein inactivate viral RNA synthesis,". Virology, 304(1):135-145 (2002).
Soboloff et al., "Orai1 and STIM Reconstitute Store-operated Calcium Channel Function," Journ. Biol. Chem, vol. 281, No. 30, pp, 20661-20665, XP-002489195 (2006).
Strange et al., "Physiological roles of STIM1 and Orai1 homologs and CRAC channels in the genetic model organism Caenorhabditis elegans," Cell Calcium, Churchill Livingstone Medical Journals 42(2):193-203 (2007).
Strausberg et al., GenEmbl Accession No. BC069270, computer printout, pp. 13-17 (2004).
Streb et al, "Release of Ca2+ from nonmitochondrial intracellular store in pancreatic acinar cells by inositol-1,4,5-trisphosphate," *Nature.* Nov. 3-9, 1983;306(5938):67-9.
Suzuki et al,, "Design and synthesis of calcium and magnesium ionophores based on double-armed diazacrown ether compounds and their application to an ion-sensing component for an ion-selective electrode," Anal. Chem. 67:324-334 (1995).
The International HapMaP Consortium, "The International HapMap Project." Nature 426:789-796, 2003.
Tiscornia et al., "A general method for gene knockdown in mice by using lentiviral vectors expressing small interfering RNA," PNAS 100:1844-1848 (2003).
Tomasinsig et al., "The cathelicidins—structure, function and evolution," Curr. Protein and Peptide Sci., 6(1):23-24 (2005).
Trevilyan et al., "Potent inhibition of NFAT activation and T cell cytokine production by novel low molecular weight pyrazole compounds.," *J Biol Chem.* Dec. 21, 2001;276(51):48118-26. Epub Oct. 9, 2001
U.S. Appl. No. 11/807,244 Office Action dated Mar. 7, 2011.
U.S. Appl. No. 11/807,244 Office Action dated Dec. 12, 2011.
U.S. Appl. No. 11/807,244 Office Action dated Nov. 16, 2009.
U.S. Appl. No. 11/807,244 Office Action dated Jul. 18, 2012.
U.S. Appl. No. 11/807,244 Office Action dated Jan. 26, 2009.
U.S. Appl. No. 11/807,244 Office Action dated Jun. 29, 2010.
U.S. Appl. No. 12/160,030 Office Action dated Dec. 5, 2011.
U.S. Appl. No. 12/160,030 Office Action dated Mar. 7, 2011.
U.S. Appl. No. 12/160,030 Office Action dated Aug. 18, 2010.
U.S. Appl. No. 12/160,030 Office Action dated Apr. 30, 2012.
U.S. Appl. No. 13/161,307 Office Action dated Jan. 11, 2012.
Venkatachalam, K. et al., "The cellular and molecular basis of store-operated calcium entry." Nature Cell Biology 4:E263-E272, 2002.
Vig et al., "CRACM1 is a plasma membrane protein essenial for store-operated Ca2+ enty,"Science 312(5777):1220-1223(2006).
Voets et al. (2004) "Outer pore architecture of a $Ca^{2+}$-selective TRP channel," *Journal of Biological Chemistry,* 279(15): 15223-15230.
Voets, T. et al., "CaT1 and the Calcium Release-activated Calcium Channel Manifest Distinct Pore Properties." J Biol Chem 276(51):47767-47770, 2001.

Welch, "Quantitative relationships between ryanoids, receptor affinity, and channel conductance," Frontiers in Bioscience 7:1727-1742 (2002).

Williams et al., "Identification and characterization of the STIM (stromal inreraction molecule) gene family: coding for a novel class of transmembrane proteins," Biochem. J. 357:673-685 (2001).

Williams et al., "Stromal interaction molecule 1 (STIM1), a transmembrane protein with growth suppressor activity, contains an extracellular SAM domain modified by N-linked glycosylation," Biochim. Biophys. Acta 1596:131-137 (2002).

Winslow et al., "Calcium signalling in lymphocytes," Current Opinion in Immunology, 16:299-307 (2003).

Wu et al., "FOXP3 controls regulatory T cell function through cooperation with NFAT," *Cell*. Jul. 28, 2006;126(2):375-87.

Xu et al., "Specific structural requirements for the inhibitory effect of Thapsigargin on the $Ca^{2+}$ ATPase SERCA," J. Biol. Chem. 279(17):17973-17979 (2004).

Yeromin, A. V. et al., "A Store-operated Calcium Channel in Drosophila S2 Cells." J Gen Physiol 123:167-182, 2004.

Yeromin, A. V. et al., "Molecular identification of the CRAC channel by altered ion selectivity in a mutant of Orai," Nature 443(7108):226-229 (2006).

Yue, L. et al., "CaT1 manifests the pore properties of the calcium-release-activated calcium channel." Nature 410:705-709, 2001.

Zhang et al., "Genome Wide RNAi Screen of Ca2+ influx identifies Genes that Regulate Ca2+ Channel Activity," PNAS USA 103(4):9357-9362 (2006).

Zhang, S. L. et al., "STIM1 is a Ca2+ sensor that activates CRAC channels and migrates from the Ca2+ store to the plasma membrane." Nature 437(7060):902-905, 2005.

Zweifach and Lewis (1993) "Mitogen-regulated Can) current of T lymphocytes is activated by depletion of intracellular $Ca^{++}$ stores." *Proceedings of the National Academy of Sciences*. USA, 90(13): 6295-6299.

Zweifach, A. and Lewis, R. S., "Calcium-dependent Potentiation of Store-operated Calcium Channels in T Lymphocytes." J Gen Physiol 107:597-610, 1996.

Zweifach, A. and Lewis, R. S., "Rapid Inactivation of Depletion-activated Calcium Current (Icrac) Due to Local Calcium Feedback." J Gen Physiol 105:209-226, 1995.

* cited by examiner

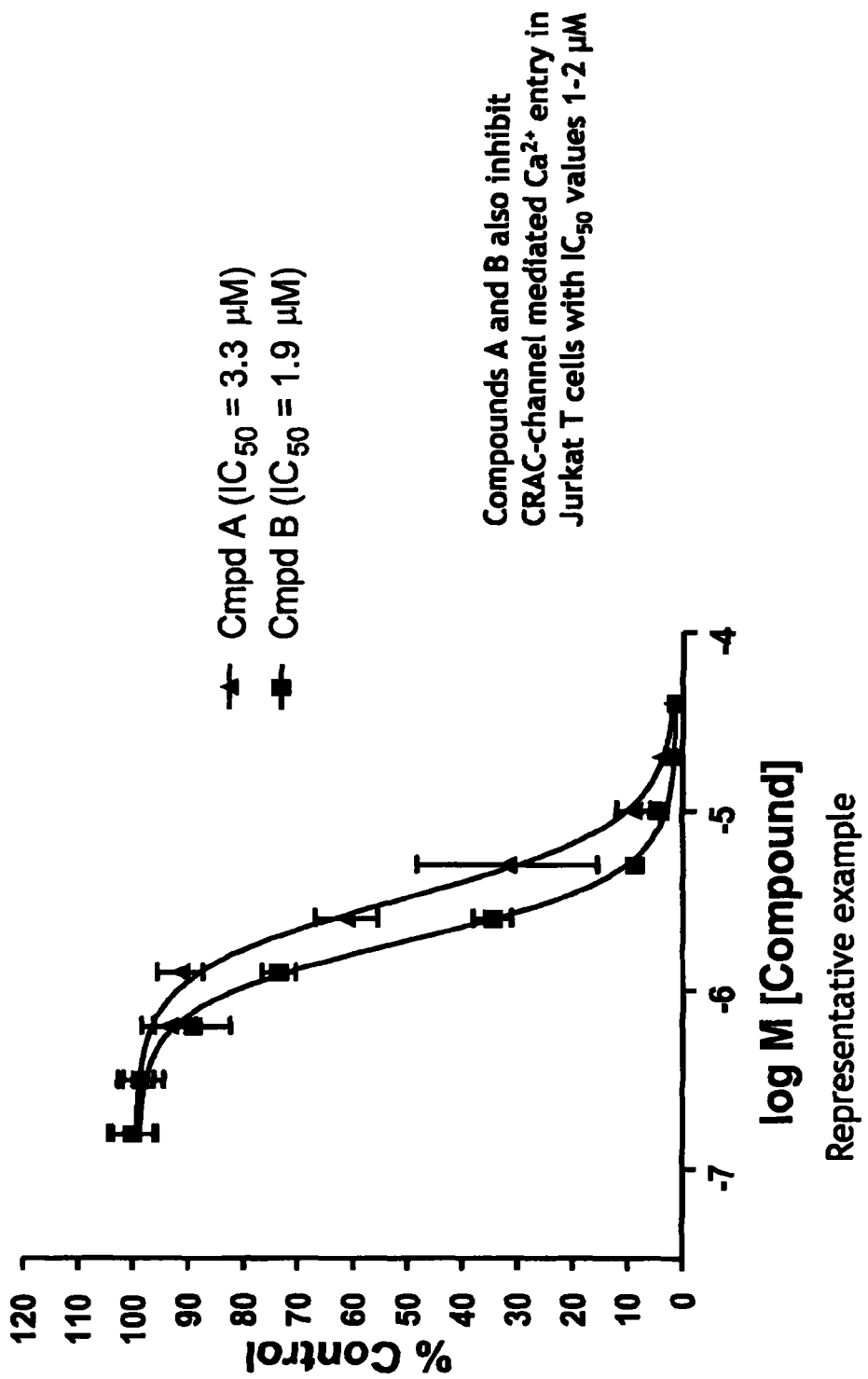

CALCIUM CHANNEL PROTEINS AND USES THEREOF

CROSS REFERENCE TO RELATED APPLICATIONS

This patent application claims the benefit of priority from U.S. Provisional Patent Application Ser. No. 60/939,922, filed May 24, 2007, which is incorporated herein by reference in its entirety.

SEQUENCE LISTING

The instant application contains a Sequence Listing which has been submitted via EFS-Web and is hereby incorporated by reference in its entirety. Said ASCII copy, created on Jul. 27, 2010, is named 34517221.txt and is 14,773 bytes in size.

FIELD OF THE INVENTION

Described herein are compositions and uses related to $Ca^{2+}$ release-activated $Ca^{2+}$ (CRAC) channel activity.

BACKGROUND OF THE INVENTION

The regulation of intracellular calcium is a key element in the transduction of signals into and within cells. Cellular responses to growth factors, neurotransmitters, hormones and a variety of other signal molecules are initiated through calcium-dependent processes.

Virtually all cell types depend in some manner upon the generation of cytoplasmic $Ca^{2+}$ signals to regulate cell function, or to trigger specific responses. Cytosolic $Ca^{2+}$ signals control a wide array of cellular functions ranging from short-term responses such as contraction and secretion to longer-term regulation of cell growth and proliferation. Usually, these signals involve some combination of release of $Ca^{2+}$ from intracellular stores, such as the endoplasmic reticulum (ER), and influx of $Ca^{2+}$ across the plasma membrane. In one example, cell activation begins with an agonist binding to a surface membrane receptor, coupled to phospholipase C (PLC) through a G-protein mechanism. PLC activation leads to the production of inositol 1,4,5-triphosphate ($IP_3$), which in turn activates the $IP_3$ receptor causing release of $Ca^{2+}$ from the ER. The fall in ER $Ca^{2+}$ then signals to plasma membrane store-operated calcium (SOC) channels.

Store-operated calcium (SOC) influx is a process in cellular physiology that controls such diverse functions such as, but not limited to, refilling of intracellular $Ca^{2+}$ stores (Putney et al. *Cell*, 75, 199-201, 1993), activation of enzymatic activity (Fagan et al., *J. Biol. Chem.* 275:26530-26537, 2000), gene transcription (Lewis, *Annu. Rev. Immunol.* 19:497-521, 2001), cell proliferation (Nunez et al., *J. Physiol.* 571.1, 57-73, 2006), and release of cytokines (Winslow et al., *Curr. Opin. Immunol.* 15:299-307, 2003). In some nonexcitable cells, e.g., blood cells, immune cells, hematopoietic cells, T lymphocytes and mast cells, SOC influx occurs through calcium release-activated calcium (CRAC) channels, a type of SOC channel.

SUMMARY OF THE INVENTION

Disclosed herein are methods of identifying an agent that modulates intracellular calcium comprising: contacting one or more test cells comprising a stromal interacting molecule (STIM) protein or a portion thereof and an Orai protein or a portion thereof, assessing the effect(s) of the agent on intracellular calcium, and identifying an agent that has an effect on intracellular calcium. In some embodiments, the STIM protein is STIM1 or STIM2, or a portion thereof. Alternatively, the STIM protein is at least 95% identical to an amino acid sequence of a STIM protein. In other embodiments, the Orai protein is Orai1, or a portion thereof. In yet other embodiments, the Orai protein is at least 95% identical to an amino acid sequence of an Orai protein.

In one aspect, the agent modulating intracellular calcium levels acts by decreasing intracellular calcium levels. In other embodiments, the methods disclosed herein further comprise a fluorescent protein or luminescent protein that is used in monitoring or measuring intracellular calcium levels. In some embodiments, the fluorescent protein is an aequorin-like protein or a chameleon or chameleon-like protein. In yet other embodiments, the methods disclosed herein further comprise a calcium depleting agent that provides for reduction of calcium levels in an intracellular calcium store. In some alternatives, the calcium depleting agent is thapsigargin. In other embodiments, the method includes an that agent modulates an activity of, modulates an interaction of, or modulates the level of, or binds to, or interacts with STIM1, Orai 1 or a combination thereof. In still her embodiments, the agent further modules a cytokine expression or secretion.

In other aspects, a mammalian cell is provided which comprises a stromal interacting molecule (STIM) protein or a portion thereof, and an Orai protein or a portion thereof. In some embodiments, the STIM protein of the mammalian cell is STIM1 or STIM2, or a portion thereof. In yet other embodiments, the Orai protein is Orai1, or a portion thereof. In still other embodiments, a mammalian cell is provided, comprising a first amino acid sequence at least 95% identical to the amino acid sequence of STIM1 and a second amino acid sequence at least 95% identical to the amino acid sequence of Orai1.

In other embodiments, a method of treating a disease, disorder or condition in a mammal is provided where the mammal would benefit from inhibition of store operated calcium channel activity, the method comprising administering a compound capable of modulating a STIM protein and/or an Orai protein, or pharmaceutically acceptable salt, pharmaceutically acceptable solvate, or pharmaceutically acceptable prodrug thereof. In other embodiments, a method of decreasing cytokine expression by inhibiting a store-operated calcium entry activation in a mammal is provided, the method comprising administering a compound capable of modulating a STIM protein and/or an Orai protein, or pharmaceutically acceptable salt, pharmaceutically acceptable solvate, or pharmaceutically acceptable prodrug thereof.

In still other embodiments, an article of manufacture, comprising packaging material, a cell comprising a stromal interacting molecule (STIM) protein or a portion thereof, and an Orai protein or a portion thereof. In some embodiments, the STIM protein of the article of manufacture is STIM1 or STIM2, and the Orai protein is Orai1.

In one aspect, described herein is a method of modulating store-operated calcium (SOC) channel activity comprising contacting the store-operated calcium (SOC) channel complex, or portion thereof, with a compound that inhibits intracellular calcium levels, or pharmaceutically acceptable salt, pharmaceutically acceptable solvate, or pharmaceutically acceptable prodrug thereof. In one embodiment, the contacting occurs in vitro. In another embodiment, the contacting occurs in vivo. In one embodiment, the intracellular calcium modulating compounds identified and described herein modulate an activity of, modulates an interaction of, or modulates the level of, or binds to, or interacts with at least one portion of the store operated calcium channel complex selected from stromal interaction molecules (STIM) or Orai family of proteins. In one embodiment, the intracellular calcium modulating compound modulates an activity of, modulates an interaction of, or modulates the level of, or binds to, or interacts with at least one portion of STIM1 or STIM2. In another embodiment the intracellular calcium modulating compound modulates an activity of, modulates an interactino of, or modulates the level of, or binds to, or interacts with at least one portion of Orai1. In one embodiment, modulating store operated calcium channel activity with an intracellular calcium modulating compound inhibits store-operated calcium entry (SOCE). In another embodiment, the store operated calcium channel complex is calcium-release activated calcium (CRAC) channel complex. In one embodiment modulating calcium release activated calcium (CRAC) activity with a compound capable of modulating a STIM protein and/or an Orai protein, inhibits the electrophysiological current ($I_{CRAC}$) directly associated with activated CRAC channels.

Also described herein are methods of treating a disease, disorder or condition in a mammal that would benefit from inhibition of store operated calcium channel activity comprising administering to the mammal an intracellular calcium modulating compound, or pharmaceutically acceptable salt, pharmaceutically acceptable solvate, or pharmaceutically acceptable prodrug thereof. In one aspect the intracellular calcium modulating compound modulates the activity of, modulates an interaction of, or binds to, or interacts with a mammalian STIM1 protein, or a mammalian STIM2 protein. In another aspect, the intracellular calcium modulating compound modulates the activity of, modulates an interaction of, or binds to, or interacts with a mammalian Orai protein. In one aspect, the intracellular calcium modulating compound modulates the activity of, modulates an interaction of, or binds to, or interacts with a mammalian STIM1 protein and a mammalian Orai1 protein.

In one embodiment, the disease, disorder or condition in a mammal is selected from diseases/disorders involving inflammation, glomerulonephritis, uveitis, hepatic diseases or disorders, renal diseases or disorders, chronic obstructive pulmonary disease, rheumatoid arthritis, inflammatory bowel disease, vasculitis, dermatitis, osteoarthritis, inflammatory muscle disease, allergic rhinitis, vaginitis, interstitial cystitis, scleroderma, osteoporosis, eczema, allogeneic or xenogeneic transplantation, graft rejection, graft-versus-host disease, lupus erythematosus, type I diabetes, pulmonary fibrosis, dermatomyositis, thyroiditis, myasthenia gravis, autoimmune hemolytic anemia, cystic fibrosis, chronic relapsing hepatitis, primary biliary cirrhosis, allergic conjunctivitis, hepatitis and atopic dermatitis, asthma, Sjogren's syndrome, cancer and other proliferative diseases, and autoimmune diseases or disorders.

Also described herein is a method of inhibiting store-operated calcium entry (SOCE) activation of nuclear factor of activated T cells (NFAT) in a mammal comprising administering a compound capable of modulating a STIM protein and/or an Orai protein, or pharmaceutically acceptable salt, pharmaceutically acceptable solvate, or pharmaceutically acceptable prodrug thereof. In one embodiment, the compounds identified and described herein modulate an interaction of, or modulates the level of, or binds to, or interacts with a mammalian STIM1 protein, or a mammalian STIM2 protein.

Also provided herein is a method of decreasing cytokine expression by inhibiting the store-operated calcium entry activation of NFAT in a manual comprising administering a compound capable of modulating a STIM protein and/or an Orai protein levels, or pharmaceutically acceptable salt, pharmaceutically acceptable solvate, or pharmaceutically acceptable prodrug thereof. In one embodiment, the compounds disclosed herein modulate an interaction of, or modulates the level of, or binds to, or interacts with a mammalian STIM1 protein or a mammalian STIM2 protein. In one embodiment, the cytokine is selected from IL-2, IL-3, IL-4, IL-5, IL-6, IL-7, IL-8, IL-9, IL-10, IL-11, IL-12, IL-13, IL-15, IL-16, IL-17, IL-18, IL-1α, IL-1β, IL-1 RA, granulocyte colony stimulating factor (G-CSF), granulocyte-macrophage colony stimulating factor (GM-CSF), oncostatin M, erythropoietin, leukemia inhibitory factor (LIF), interferons, gamma-interferon (γ-IFN), B7.1 (CD80), B7.2 (B70, CD86), TNF-α, TNF-β, LT-β, CD40 ligand, Fas ligand, CD27 ligand, CD30 ligand, 4-1BBL, Trail, beta-hexosaminidase, and migration inhibitory factor (MIF).

Other objects, features and advantages of the compounds, compositions, methods, and uses described herein will become apparent from the following detailed description. It should be understood, however, that the detailed description and the specific examples, while indicating specific embodiments, are given by way of illustration only.

BRIEF DESCRIPTION OF THE FIGURES

The novel features of the disclosed herein are set forth with particularity in the appended claims. A better understanding of the features and advantages will be obtained by reference to the following detailed description that sets forth illustrative embodiments and the accompanying drawings of which:

FIG. 11 depicts the inhibition of Orai1/STIM1-dependent $Ca^{2+}$ entry in stably transfected cells by Cmpd A and Cmpd B.

DETAILED DESCRIPTION

Figure 1:
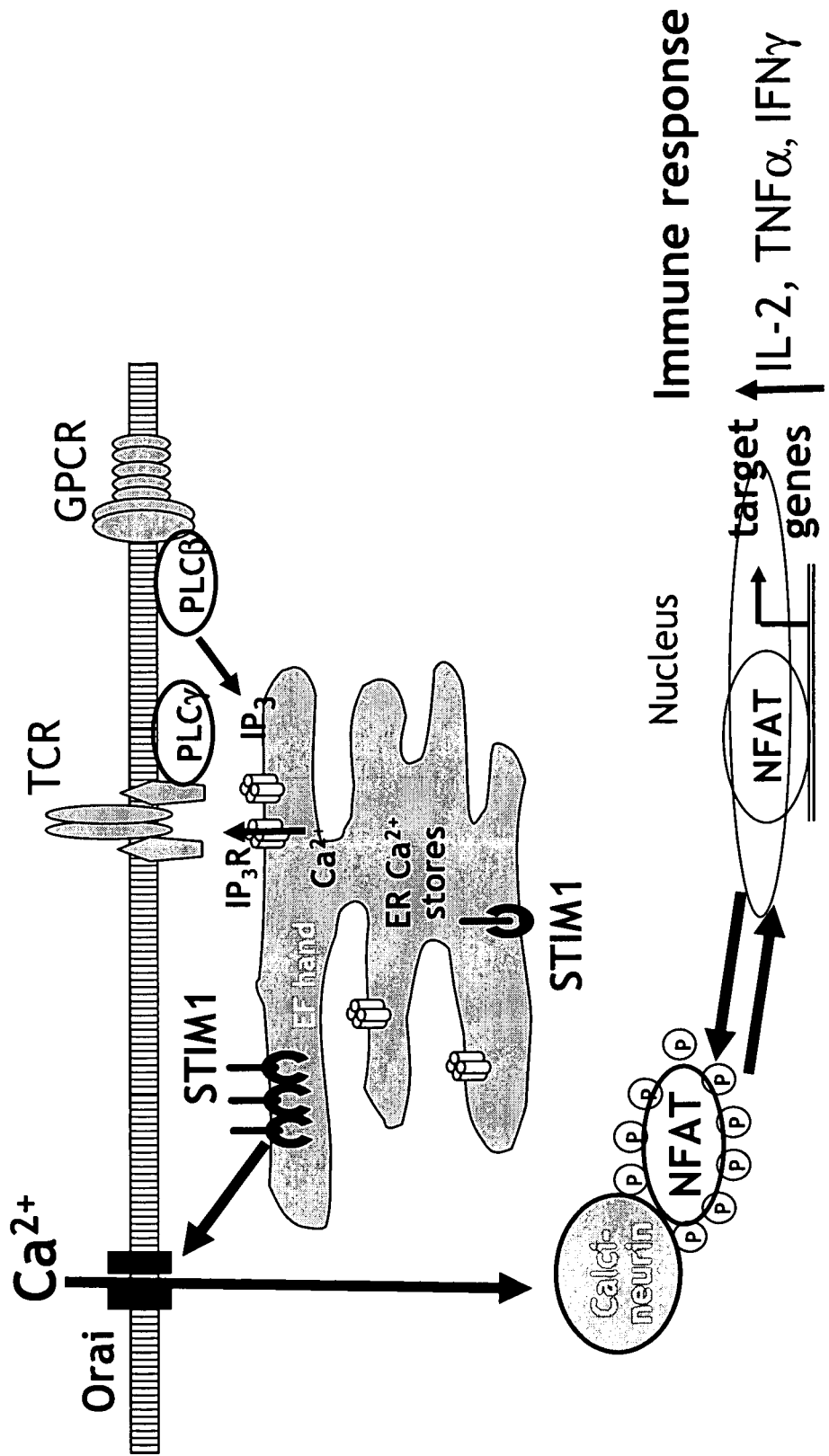
FIG. 1 outlines CRAC-regulated calcium entry pathway.

Patch-clamp experiments have identified the biophysical characteristics of $Ca^{2+}$ release-activated $Ca^{2+}$ (CRAC) channels in lymphocytes and other human cell types. Store-operated $Ca^{2+}$ (SOC) influx in *Drosophila* S2 cells occurs through a channel that shares biophysical properties with CRAC channels in human T lymphocytes. A medium-throughput RNA interference (RNAi) screen targeting 170 candidate genes in S2 cells, found an essential conserved role of Stim and the mammalian homolog STIM1 in SOC influx and CRAC channel activity. Yeromin et al. *J. Gen. Physiol* (2004) 123:167-182. STIM1 and STIM2 also were identified in an independently performed screen of HeLa cells by using the *Drosophila* enzyme Dicer to generate small interfering RNA species from dsRNA. *Drosophila* Stim and the mammalian homolog STIM1 appear to play dual roles in the CRAC channel activation sequence, sensing the luminal $Ca^{2+}$ store content through an EF hand motif and trafficking from an endoplasmic reticulum (ER)-like localization to the plasma membrane to trigger CRAC channel activity. However, as single-pass transmembrane proteins, Stim and its mammalian homolog STIM1 are unlikely to form the CRAC channel itself. To search systematically for additional components of the CRAC channel, and to analyze the signaling network and other required factors that lead to SOC channel activity, a genome-wide screen on S2 cells was devised and performed based on a fluorescence assay of $Ca^{2+}$ influx. The library at Harvard's *Drosophila* RNAi Screening Center (DRSC) of 23,845 dsRNA amplicons has been used in several functional screens.

A genetic defect was identified in patients with severe combined immune deficiency (SCID). The screen in the genome-wide study made use of the ability of thapsigargin (TG) to send GFP-tagged nuclear factor of activated T cells (NFAT) to the nucleus in S2 cells, providing an assay for disruption of signaling anywhere in the cascade from elevated $[Ca^{2+}]_i$ to calcineurin activation and nuclear relocalization of NFAT. The fly gene olf186-F (named Orai) was identified in the screen, and a human homolog on chromosome 12 was shown to be mutated in SCID patients, resulting in the loss of CRAC channel activity. Heterologous expression of the wild-type human homolog, which was named Orai1, restored CRAC channel activity in SCID T cell lines.

Based on direct $Ca^{2+}$ influx measurements in a genome-wide screen, several genes were identified that are required for CRAC channel function in S2 cells, including confirmation of the role of STIM1, as well as a functional requirement of olf186-F (Orai) for $Ca^{2+}$ signaling. Moreover, the results show the synergistic activity of STIM1 and Grail in the inhibition of $Ca^{2+}$ influx or entry into the cell. The results were further extended to investigate effects of knockdown and overexpression on CRAC channel activity. Also shown was the role of sarco-/ER calcium ATPase (SERCA) pump and the trafficking protein Syntaxin 5 as required for CRAC channel activity.

This genome-wide screening, based on direct $Ca^{2+}$ influx measurements, validated Stim and identified several additional genes that are required for CRAC channel activity. Thus, independently identified was olf186-F (Orai) as essential for $Ca^{2+}$ signaling and activation of CRAC current in *Drosophila* S2 cells. In addition, Orai based on overexpression assays likely forms an essential part of the CRAC channel. In mammalian cells overexpression of STIM1 increases $Ca^{2+}$ influx rates and CRAC currents by only ≈2-fold, but in *Drosophila* S2 cells, the data support that overexpression of Stim alone does not increase CRAC current, consistent with Stim serving as a channel activator rather than the channel itself. In contrast, transfection of olf186-F by itself increased CRAC current densities 3-fold, and cotransfection of olf186-F with Stim resulted in an 8-fold enhancement and the largest CRAC currents ever recorded. These results support that olf186-F constitutes part of the CRAC channel and that Stim serves as the messenger for its activation. Consistent with this hypothesis, the CRAC channel activation kinetics during passive $Ca^{2+}$ store depletion were significantly faster with cotransfected Stim.

Similar to Stim, knockdown of olf186-F did not produce a severe cell growth phenotype (data not shown). The olf186-F gene is a member of a highly conserved gene family that contains three homologs in mammals, two in chicken, three in zebrafish, and one member only in fly and worm (see FIG. 5A). C09F5.2, the only homolog in *Caenorhabditis elegans*, is expressed in intestine, hypodermis, and reproductive system as well as some neuron-like cells in the head and tail regions (www.wormbase.org). Worms under RNAi treatment against C09F5.2 are sterile. Analysis of hydrophobic regions of the predicted protein from the fly gene and the three mammalian homologs suggested the presence of four conserved transmembrane segments. Cytoplasmic C termini are suggested by the presence of coiled-coil motifs in each sequence. A predicted transmembrane topology and the sequence for the fly gene are shown in FIG. 8C. Sequence alignment between members from human, chicken, and fly revealed strong sequence conservation in putative transmembrane regions and conserved negatively charged residues in loops between transmembrane segments. All three human members are expressed in the immune system (GNF Symatlas; http://symatlas.gnf.org/SymAtlas). Mutation of a human homolog of *Drosophila* olf186-F, ORAI1 on chromosome 12, appears to be the cause of defective CRAC channel activity in severe combined immune deficiency patient T cells, consistent with a requirement for functional CRAC channels in the immune response. Interestingly, microarray data from public databases (GEO profiles; www.ncbi.nlm.nih.gov) combined with tissue-specific EST counts show that all three human members are expressed in a variety of nonexcitable tissues including thymus, lymph node, intestine, dermis, and many other tissues including the brain, although expression patterns and levels are different among the three members.

Ca-P60A has been proposed to be the only *Drosophila* SERCA gene. The ER pump function was validated by showing that ionomycin did not induce significant store release from S2 cells pretreated with dsRNA against Ca-P60A, consistent with a previous report. The elevation in resting $[Ca^{2+}]_i$ and rapidly changing $Ca^{2+}$ transients during changes in external $Ca^{2+}$ before addition of TG indicates a low level of constitutive CRAC channel activity induced by store depletion. In addition, SERCA knockdown inhibited CRAC channel activity after passive store depletion in whole-cell patch recordings. These results are consistent with the SERCA pump being required for normal activity of CRAC channels but do not rule out indirect inhibition of CRAC current as a consequence of residual high resting $[Ca^{2+}]_i$ or store depletion.

Among the hits, several are believed to be involved in protein trafficking. The gene products of both Syx5 and Syx1A are t-SNARE proteins involved in vesicle fusion in many cell types. The RNAi effects of Syx5 was verified at the single-cell level and demonstrated strong suppression of CRAC channel activity as well as the SOC influx. tsr regulates SOC influx indirectly by controlling cell metabolism because RNAi of tsr did not significantly influence CRAC current density in whole-cell patch-clamp experiments. Membrane trafficking previously has been demonstrated to play a role in SOC channel activity in *Xenopus* oocytes, based on inhibition by botulinum toxin or by a dominant-negative SNAP-25 construct, and our results further support a requirement for syntaxins and SNARE-complex formation, possibly to mediate translocation of Stim to the plasma membrane. The screen also revealed three other groups of hits that influence calcium dynamics.

Thus, by co-expressing STIM and Orai polypeptides in the same cell, a agent inhibiting either the STIM or Orai polypeptides, or both, affects a larger inhibitory effect on intracellular calcium levels or calcium influx, then by the presence of the STIM or Orai polypeptide alone. As discussed, the STIM protein, a single-pass transmembrane protein localized in the endoplasmic reticulum, functions as a sensor of luminal $Ca^{2+}$ store content through an EF hand motif. Upon decrease of intracellular calcium levels, STIM migrates to the plasma membrane to interact with the Orai polypeptide, triggering CRAC channel activity. The synergistic activity of the combination of STIM and Orai reflects the physiological role that both STIM and Orai in concert play in forming the CRAC channel, and along with the SERCA pump and the trafficking protein Syntaxin 5, mediate and control the level of intracellular calcium. As such, assays that identify agents that disrupt the synergistic activity of STIM and Orai would be useful in the regulation of intracellular calcium, and subsequent downstream events, including immunological responses. Accordingly, included herein are compositions that comprise a labeled STIM polypeptide and a labeled Orai polypeptide, wherein the labeled STIM and Orai polypeptide when in proximity of each other emit a second energy frequency (e.g. FRET activation), indicating the migration of the STIM polypeptide to the Orai polypeptide. Also included are methods to identify agents that disrupt STIM and Orai interaction by identifying agents that modulate the interaction between STIM and Orai. In some embodiments, the STIM polypeptide and the Orai polypeptide are mammalian. In other embodiments the STIM polypeptide is STIM1 or STIM2. In yet other embodiments, the Orai polypeptide is Orai 1. In still other embodiments, nucleotides encoding the STIM and Orai polypeptides are transiently transfected. In yet other embodiments, nucleotides encoding the polypeptides are stably transfected. In another embodiment, nucleotides encoding the polypeptides are overexpressed. In other embodiments, the label is fluorescent or radioactive.

Also disclosed herein are compositions that comprise a STIM polypeptide and Orai polypeptide, and the synergistic activity of both polypeptides in regulating SOC and calcium influx into a cell. In some embodiments, the STIM polypeptide and the Orai polypeptide are mammalian. In other embodiments the STIM polypeptide is STIM1 or STIM2. In yet other embodiments, the Orai polypeptide is Orai1. In still other embodiments, nucleotides encoding the STIM and Orai polypeptides are transiently transfected. In yet other embodiments, nucleotides encoding the polypeptides are stably transfected. In another embodiment, nucleotides encoding the polypeptides are overexpressed.

In yet other embodiments, disclosed are uses of the compositions described herein to identify agents that affect intracellular calcium levels. By way of example only, intracellular calcium levels are monitored via ion flux analysis (e.g. patch clamp analysis), or by monitoring the influx of radioactive or fluorescent calcium tracers into the cell in response to the depletion of calcium stores in the cell. In some embodiments, thapsigargin treatment depletes the calcium stores. Thus, treatment with thapsigargin depletes intracellular calcium stores, which triggers the STIM $Ca^{2+}$ sensor and subsequent activation of the STIM/Orai CRAC channel. Accordingly, disclosed herein are methods of identifying agents that affect intracellular calcium levels by treating test cells comprising a STIM polypeptide and an Orai polypeptide, and monitoring intracellular calcium levels as a result of treatment of the test cells with said agent.

Additionally, disclosed herein are compounds that inhibit the STIM/Orai CRAC-channel mediated calcium influx. The compounds are optionally used, for example, to modulate cytokine levels by the modulation of the intracellular calcium stores in immunological cells, e.g. T-cells.

Certain Terminology

Unless defined otherwise, all technical and scientific terms used herein have the same meaning as is commonly understood in the field to which the claimed subject matter belongs. In the event that there is a plurality of definitions for terms herein, those in this section prevail. Where reference is made to a URL or other such identifier or address, it is understood that such identifiers generally change and particular information on the internet comes and goes, but equivalent information is found by searching the internet. Reference thereto evidences the availability and public dissemination of such information.

It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a," "an" and "the" include plural referents unless the context clearly dictates otherwise. In this application, the use of "or" means "and/or" unless stated otherwise. Furthermore, use of the term "including" as well as other forms, such as "include", "includes," and "included," is not limiting.

The section headings used herein are for organizational purposes only and are not to be construed as limiting the subject matter described.

Definition of standard chemistry and molecular biology terms are found in reference works, including but not limited to, Carey and Sundberg "ADVANCED ORGANIC CHEMISTRY 4$^{TH}$ ED." Vols. A (2000) and B (2001), Plenum Press, New York, and "MOLECULAR BIOLOGY OF THE CELL 5$^{TH}$ ED." (2007), Garland Science, New York. Unless otherwise indicated, conventional methods of mass spectroscopy, NMR, HPLC, protein chemistry, biochemistry, recombinant DNA techniques and pharmacology, are contemplated within the scope of the embodiments disclosed herein.

Unless specific definitions are provided, the nomenclature employed in connection with, and the laboratory procedures and techniques of, analytical chemistry, and medicinal and pharmaceutical chemistry described herein are those generally used. In some embodiments, standard techniques are used for chemical analyses, pharmaceutical preparation, formulation, and delivery, and treatment of patients. In other embodiments, standard techniques are used for recombinant DNA, oligonucleotide synthesis, and tissue culture and transformation (e.g., electroporation, lipofection). In finer embodiments, reactions and purification techniques are performed e.g., using kits of manufacturer's specifications or as described herein. The foregoing techniques and procedures are generally performed of conventional methods and as described in various general and more specific references that are cited and discussed throughout the present specification.

It is to be understood that the methods and compositions described herein are not limited to the particular methodology, protocols, cell lines, constructs, and reagents described herein. It is also to be understood that the terminology used herein is for the purpose of describing particular embodiments only, and is not intended to limit the scope of the methods, compounds, compositions described herein.

The terms "kit" and "article of manufacture" are used as synonyms.

As used herein, an "Orai protein" includes Orai1 (SEQ ID NO: 1 as described in WO 07/081,804), Orai2 (SEQ ID NO: 2 as described in WO 07/081,804), or Orai3 (SEQ ID NO: 3 as described in WO 07/081,804). Orai1 nucleic acid sequence corresponds to GenBank accession number NM_032790 (SEQ ID NO: 21), Orai2 nucleic acid sequence corresponds to GenBank accession number BC069270 (SEQ ID NO: 22) and Orai3 nucleic acid sequence corresponds to GenBank accession number NM_152288 (SEQ ID NO: 23). As used herein, Orai refers to any one of the Orai genes, e.g., Orai1, Orai2, Orai3 (see Table I of WO 07/081,804). As described herein, such proteins have been identified as being involved in, participating in and/or providing for store-operated calcium entry or modulation thereof, cytoplasmic calcium buffering and/or modulation of calcium levels in or movement of calcium into, within or out of intracellular calcium stores (e.g., endoplasmic reticulum). In alternative embodiments, an Orai protein may be labeled with a tag molecule, by way of example only, is an enzyme fragment, a protein (e.g. c-myc or other tag protein or fragment thereof), an enzyme tag, a fluorescent tag, a fluorophore tag, a chromophore tag, a Raman-activated tag, a chemiluminescent tag, a quantum dot marker, an antibody, a radioactive tag, or combinations thereof.

The terms "treat," "treating" or "treatment," as used herein, include alleviating, abating or ameliorating a disease, disorder or condition symptoms, preventing additional symptoms, ameliorating or preventing the underlying causes of symptoms, inhibiting the disease, disorder or condition, e.g., arresting the development of the disease, disorder or condition, relieving the disease, disorder or condition, causing regression of the disease, disorder or condition, relieving a condition caused by the disease, disorder or condition, or stopping the symptoms of the disease, disorder or condition either prophylactically and/or therapeutically.

As used herein, the term "target protein" refers to a protein or a portion of a protein capable of being bound by, or interacting with a compound described herein, such as a compound capable of modulating a STIM protein and/or an Orai protein. In certain embodiments, a target protein is a STIM protein. In other embodiments, a target protein is an Orai protein, and in yet other embodiments, the compound targets both STIM and Orai proteins.

As used herein, "STIM protein" includes but is not limited to, mammalian STIM-1, such as human and rodent (e.g., mouse) STIM-1, *Drosophila melanogaster* D-STIM, *C. elegans* C-STIM, *Anopheles gambiae* STIM and mammalian STIM-2, such as human and rodent (e.g., mouse) STIM-2. As described herein, such proteins have been identified as being involved in, participating in and/or providing for store-operated calcium entry or modulation thereof, cytoplasmic calcium buffering and/or modulation of calcium levels in or movement of calcium into, within or out of intracellular calcium stores (e.g., endoplasmic reticulum).

As used herein, an "Orai protein" includes Orai1 (SEQ ID NO: 1 as described in WO 07/081,804), Orai2 (SEQ ID NO: 2 as described in WO 07/081,804), or Orai3 (SEQ ID NO: 3 as described in WO 07/081,804). Orai1 nucleic acid sequence corresponds to GenBank accession number NM_032790, Orai2 nucleic acid sequence corresponds to GenBank accession number BC069270 and Orai3 nucleic acid sequence corresponds to GenBank accession number NM_152288. As used herein, Orai refers to any one of the Orai genes, e.g., Orai1, Orai2, Orai3 (see Table I of WO 07/081,804). As described herein, such proteins have been identified as being involved in, participating in and/or providing for store-operated calcium entry or modulation thereof, cytoplasmic calcium buffering and/or modulation of calcium levels in or movement of calcium into, within or out of intracellular calcium stores (e.g., endoplasmic reticulum). In alternative embodiments, an Orai protein may be labeled with a tag molecule, by way of example only, is an enzyme fragment, a protein (e.g. c-myc or other tag protein or fragment thereof), an enzyme tag, a fluorescent tag, a fluorophore tag, a chromophore tag, a Raman-activated tag, a chemiluminescent tag, a quantum dot marker, an antibody, a radioactive tag, or combinations thereof.

The term "fragment" or "derivative" when referring to a protein (e.g. STIM, Orai) means proteins or polypeptides which retain essentially the same biological function or activity in at least one assay as the native protein(s). For example, the fragments or derivatives of the referenced protein maintains at least about 50% of the activity of the native proteins, at least 75%, at least about 95% of the activity of the native proteins, as determined e.g. by a calcium influx assay.

As used herein, amelioration of the symptoms of a particular disease, disorder or condition by administration of a particular compound or pharmaceutical composition refers to any lessening of severity, delay in onset, slowing of progression, or shortening of duration, whether permanent or temporary, lasting or transient that are attributed to or associated with administration of the compound or composition.

The term "modulate," as used herein, means to interact with a target protein either directly or indirectly so as to alter the activity of the target protein, including, by way of example only, to inhibit the activity of the target, or to limit or reduce the activity of the target.

As used herein, the term "modulator" refers to a compound that alters an activity of a target. For example, in some embodiments, a modulator causes an increase or decrease in the magnitude of a certain activity of a target compared to the magnitude of the activity in the absence of the modulator. In certain embodiments, a modulator is an inhibitor, which decreases the magnitude of one or more activities of a target. In certain embodiments, an inhibitor completely prevents one or more activities of a target.

As used herein, "modulation" with reference to intracellular calcium refers to any alteration or adjustment in intracellular calcium including but not limited to alteration of calcium concentration in the cytoplasm and/or intracellular calcium storage organelles, e.g., endoplasmic reticulum, and alteration of the kinetics of calcium fluxes into, out of and within cells. In aspect, modulation refers to reduction.

The terms "inhibits", "inhibiting", or "inhibitor" of SOC channel activity or CRAC channel activity, as used herein, refer to inhibition of store operated calcium channel activity or calcium release activated calcium channel activity.

The term "acceptable" with respect to a formulation, composition or ingredient, as used herein, means having no persistent detrimental effect on the general health of the subject being treated.

By "pharmaceutically acceptable," as used herein, refers a material, such as a carrier or diluent, which does not abrogate the biological activity or properties of the compound, and is relatively nontoxic, i.e., the material is administered to an individual without causing undesirable biological effects or interacting in a deleterious manner with any of the components of the composition in which it is contained.

The term "pharmaceutical composition" refers to a mixture of a compound capable of modulating a STIM protein and/or an Orai protein as described herein with other chemical components, such as carriers, stabilizers, diluents, dispersing agents, suspending agents, thickening agents, and/or excipients. The pharmaceutical composition facilitates administration of the compound to an organism. Multiple techniques of administering a compound exist including, but not limited to: intravenous, oral, aerosol, parenteral, ophthalmic, pulmonary and topical administration.

The terms "effective amount" or "therapeutically effective amount," as used herein, refer to a sufficient amount of an agent or a compound being administered which will relieve to some extent one or more of the symptoms of the disease or condition being treated. The result is reduction and/or alleviation of the signs, symptoms, or causes of a disease, or any other desired alteration of a biological system. For example, an "effective amount" for therapeutic uses is the amount of the composition that includes a compound of capable of modulating a STIM protein and/or an Orai protein as described herein required to provide a clinically significant decrease in disease symptoms. In some embodiments, an appropriate "effective" amount in any individual case is determined using techniques, such as a dose escalation study.

The terms "enhance" or "enhancing," as used herein, means to increase or prolong either in potency or duration a desired effect. Thus, in regard to enhancing the effect of therapeutic agents, the term "enhancing" refers to the ability to increase or prolong, either in potency or duration, the effect of other therapeutic agents on a system. An "enhancing-effective amount," as used herein, refers to an amount adequate to enhance the effect of another therapeutic agent in a desired system.

The term "carrier," as used herein, refers to relatively non-toxic chemical compounds or agents that facilitate the incorporation of a compound into cells or tissues.

The term "diluent" refers to chemical compounds that are used to dilute the compound of interest prior to delivery. In some embodiments, diluents are used to stabilize compounds because they provide a more stable environment. Salts dissolved in buffered solutions (which also provide pH control or maintenance) are utilized as diluents, including, but not limited to a phosphate buffered saline solution.

A "metabolite" of a compound disclosed herein is a derivative of that compound that is formed when the compound is metabolized.

"Bioavailability" refers to the percentage of the weight of the compound disclosed herein (e.g. compound capable of modulating intracellular calcium that is delivered into the general circulation of the animal or human being studied). The total exposure (AUC(0-∞)) of a drug when administered intravenously is usually defined as 100% bioavailable (F %). "Oral bioavailability" refers to the extent to which a compound disclosed herein, is absorbed into the general circulation when the pharmaceutical composition is taken orally as compared to intravenous injection.

"Blood plasma concentration" refers to the concentration of a compound capable of modulating a STIM protein and/or an Orai protein as disclosed herein, in the plasma component of blood of a subject. It is understood that the plasma concentration of compounds described herein likely varies significantly between subjects, due to variability with respect to metabolism and/or possible interactions with other therapeutic agents. In accordance with one embodiment disclosed herein, the blood plasma concentration of the compounds disclosed herein varies from subject to subject. Likewise, in some embodiments, values such as maximum plasma concentration ($C_{max}$) or time to reach maximum plasma concentration ($T_{max}$), or total area under the plasma concentration time curve (AUC(0-∞)) varies from subject to subject. Due to this variability, the amount necessary to constitute "a therapeutically effective amount" of a compound will vary from subject to subject.

As used herein, "calcium homeostasis" refers to the maintenance of an overall balance in intracellular calcium levels and movements, including calcium signaling, within a cell.

As used herein, "intracellular calcium" refers to calcium located in a cell without specification of a particular cellular location. In contrast, "cytosolic" or "cytoplasmic" with reference to calcium refers to calcium located in the cell cytoplasm.

As used herein, an effect on intracellular calcium is any alteration of any aspect of intracellular calcium, including but not limited to, an alteration in intracellular calcium levels and location and movement of calcium into, out of or within a cell or intracellular calcium store or organelle. For example, in some embodiments, an effect on intracellular calcium is an alteration of the properties, such as, for example, the kinetics, sensitivities, rate, amplitude, and electrophysiological characteristics, of calcium flux or movement that occurs in a cell or portion thereof. In some embodiments, an effect on intracellular calcium is an alteration in any intracellular calcium-modulating process, including, store-operated calcium entry, cytosolic calcium buffering, and calcium levels in or movement of calcium into, out of or within an intracellular calcium store. Any of these aspects are assessed in a variety of ways including, but not limited to, evaluation of calcium or other ion (particularly cation) levels, movement of calcium or other ion (particularly cation), fluctuations in calcium or other ion (particularly cation) levels, kinetics of calcium or other ion (particularly cation) fluxes and/or transport of calcium or other ion (particularly cation) through a membrane. An alteration is any such change that is statistically significant. Thus, for example, in some embodiments, if intracellular calcium in a test cell and a control cell is said to differ, such differences are a statistically significant difference.

As used herein, "involved in", with respect to the relationship between a protein and an aspect of intracellular calcium or intracellular calcium regulation means that when expression or activity of the protein in a cell is reduced, altered or eliminated, there is a concomitant or associated reduction, alteration or elimination of one or more aspects of intracellular calcium or intracellular calcium regulation. Such an alteration or reduction in expression or activity occurs by virtue of an alteration of expression of a gene encoding the protein or by altering the levels of the protein. A protein involved in an aspect of intracellular calcium, such as, for example, store-operated calcium entry, thus, are one that provides for or participates in an aspect of intracellular calcium or intracellular calcium regulation. For example, a protein that provides for store-operated calcium entry are a STIM protein and/or an Orai protein.

As used herein, a protein that is a component of a calcium channel is a protein that participates in multi-protein complex that forms the channel.

As used herein, "cation entry" or "calcium entry" into a cell refers to entry of cations, such as calcium, into an intracellular location, such as the cytoplasm of a cell or into the lumen of an intracellular organelle or storage site. Thus, in some embodiments, cation entry is, for example, the movement of cations into the cell cytoplasm from the extracellular medium or from an intracellular organelle or storage site, or the movement of cations into an intracellular organelle or storage site from the cytoplasm or extracellular medium. Movement of calcium into the cytoplasm from an intracellular organelle or storage site is also referred to as "calcium release" from the organelle or storage site.

As used herein, "protein that modulates intracellular calcium" refers to any cellular protein that is involved in regulating, controlling and/or altering intracellular calcium. For example, in some embodiments, such a protein is involved in altering or adjusting intracellular calcium in a number of ways, including, but not limited to, through the maintenance of resting or basal cytoplasmic calcium levels, or through involvement in a cellular response to a signal that is transmitted in a cell through a mechanism that includes a deviation in intracellular calcium from resting or basal states. In the context of a "protein that modulates intracellular calcium," a "cellular" protein is one that is associated with a cell, such as, for example, a cytoplasmic protein, a plasma membrane-associated protein or an intracellular membrane protein. Proteins that modulate intracellular calcium include, but are not limited to, ion transport proteins, calcium-binding proteins and regulatory proteins that regulate ion transport proteins.

As used herein, "amelioration" refers to an improvement in a disease or condition or at least a partial relief of symptoms associated with a disease or condition.

As used herein, "cell response" refers to any cellular response that results from ion movement into or out of a cell or within a cell. In some embodiments, the cell response is associated with any cellular activity that is dependent, at least in part, on ions such as, for example, calcium. Such activities optionally include, for example, cellular activation, gene expression, endocytosis, exocytosis, cellular trafficking and apoptotic cell death.

As used herein, "immune cells" include cells of the immune system and cells that perform a function or activity in an immune response, such as, but not limited to, T-cells, B-cells, lymphocytes, macrophages, dendritic cells, neutrophils, eosinophils, basophils, mast cells, plasma cells, white blood cells, antigen presenting cells and natural killer cells.

As used herein, "cytokine" refers to small soluble proteins secreted by cells that in some embodiments, alter the behavior or properties of the secreting cell or another cell. Cytokines bind to cytokine receptors and trigger a behavior or property within the cell, for example, cell proliferation, death or differentiation. Exemplary cytokines include, but are not limited to, interleukins (e.g., IL-2, IL-3, IL-4, IL-5, IL-6, IL-7, IL-8, IL-9, IL-10, IL-11, IL-12, IL-13, IL-15, IL-16, IL-17, IL-18, IL-1α, IL-1β, and IL-1 RA), granulocyte colony stimulating factor (G-CSF), granulocyte-macrophage colony stimulating factor (GM-CSF), oncostatin M, erythropoietin, leukemia inhibitory factor (LIF), interferons, B7.1 (also known as CD80), B7.2 (also known as B70, CD86), TNF family members (TNF-α, TNF-β, LT-β, CD40 ligand, Fas ligand, CD27 ligand, CD30 ligand, 4-1BBL, Trail), and MIF.

"Store operated calcium entry" or "SOCE" refers to the mechanism by which release of calcium ions from intracellular stores is coordinated with ion influx across the plasma membrane.

"Selective inhibitor of SOC channel activity" means that the inhibitor is selective for SOC channels and does not substantially affect the activity of other types of ion channels.

"Selective inhibitor of CRAC channel activity" means that the inhibitor is selective for CRAC channels and does not substantially affect the activity of other types of ion channels and/or other SOC channels.

Cellular calcium homeostasis is a result of the summation of regulatory systems involved in the control of intracellular calcium levels and movements. Cellular calcium homeostasis is achieved, at least in part, by calcium binding and by movement of calcium into and out of the cell across the plasma membrane and within the cell by movement of calcium across membranes of intracellular organelles including, for example, the endoplasmic reticulum, sarcoplasmic reticulum, mitochondria and endocytic organelles including endosomes and lysosomes.

Movement of calcium across cellular membranes is carried out by specialized proteins. For example, calcium from the extracellular space enters the cell through various calcium channels and a sodium/calcium exchanger and is actively extruded from the cell by calcium pumps and sodium/calcium exchangers. Calcium is also released from internal stores through inositol trisphosphate or ryanodine receptors and is likely taken up by these organelles by means of calcium pumps.

Calcium enters cells by any of several general classes of channels, including but not limited to, voltage-operated calcium (VOC) channels, store-operated calcium (SOC) channels, and sodium/calcium exchangers operating in reverse mode. VOC channels are activated by membrane depolarization and are found in excitable cells like nerve and muscle and are for the most part not found in nonexcitable cells. Under some conditions, $Ca^{2+}$ also enters cells via $Na^+$—$Ca^{2+}$ exchangers operating in reverse mode.

Endocytosis provides another process by which cells take up calcium from the extracellular medium through endosomes. In addition, some cells, e.g., exocrine cells, release calcium via exocytosis.

Cytosolic calcium concentration is tightly regulated with resting levels usually estimated at approximately 0.1 µM in mammalian cells, whereas the extracellular calcium concentration is typically about 2 mM. This tight regulation facilitates transduction of signals into and within cells through transient calcium flux across the plasma membrane and membranes of intracellular organelles. There is a multiplicity of intracellular calcium transport and buffer systems in cells that serve to shape intracellular calcium signals and maintain the low resting cytoplasmic calcium concentration. In cells at rest, the principal components involved in maintaining basal calcium levels are calcium pumps and leaks in the endoplasmic reticulum and plasma membrane. Disturbance of resting cytosolic calcium levels effects transmission of such signals and give rise to defects in a number of cellular processes. For example, cell proliferation involves a prolonged calcium signaling sequence. Other cellular processes include, but are not limited to, secretion, signaling, and fertilization, involve calcium signaling.

Cell-surface receptors that activate phospholipase C(PLC) create cytosolic $Ca^{2+}$ signals from intra- and extra-cellular sources. An initial transient rise of $[Ca^{2+}]_i$ (intracellular calcium concentration) results from the release of $Ca^{2+}$ from the endoplasmic reticulum (ER), which is triggered by the PLC product, inositol-1,4,5-trisphosphate ($P_3$), opening $IP_3$ receptors in the ER (Streb et al. Nature, 306, 67-69, 1983). A subsequent phase of sustained $Ca^{2+}$ entry across the plasma membrane then ensues, through specialized store operated calcium (SOC) channels (in the case of immune cells the SOC channels are calcium release-activated calcium (CRAC) channels) in the plasma membrane. Store-operated $Ca^{2+}$ entry (SOCE) is the process in which the emptying of $Ca^{2+}$ stores itself activates $Ca^{2+}$ channels in the plasma membrane to help refill the stores (Putney, Cell Calcium, 7, 1-12, 1986; Parekh et al, Physiol. Rev. 757-810; 2005). SOCE does more than simply provide $Ca^{2+}$ for refilling stores, but itself generates sustained $Ca^{2+}$ signals that control such essential functions as gene expression, cell metabolism and exocytosis (Parekh and Putney, Physiol. Rev. 85, 757-810 (2005).

In lymphocytes and mast cells, activation of antigen or Fc receptors causes the release of $Ca^{2+}$ from intracellular stores, which in turn leads to $Ca^{2+}$ influx through CRAC channels in the plasma membrane. The subsequent rise in intracellular $Ca^{2+}$ activates calcineurin, a phosphatase that regulates the transcription factor NFAT. In resting cells, NFAT is phosphorylated and resides in the cytoplasm, but when dephosphorylated by calcineurin, NFAT translocates to the nucleus and activates different genetic programmes depending on stimulation conditions and cell type. In response to infections and during transplant rejection, NFAT partners with the transcription factor AP-1 (Fos-Jun) in the nucleus of "effector" T cells, thereby transactivating cytokine genes, genes that regulate T cell proliferation and other genes that orchestrate an active immune response (Rao et al., Annu Rev Immunol, 1997; 15:707-47). In contrast, in T cells recognizing self antigens, NFAT is activated in the absence of AP-1, and activates a transcriptional programme otherwise known as "anergy" that suppresses autoimmune responses (Macian et al., Transcriptional mechanisms underlying lymphocyte tolerance. Cell. 2002 Jun. 14; 109(6):719-31). In a subclass of T cells, known as regulatory T cells which suppress autoimmunity mediated by self-reactive effector T cells, NFAT partners with the transcription factor FOXP3 to activate genes responsible for suppressor function (Wu et al., Cell, 2006 Jul. 28; 126(2):375-87; Rudensky A Y, Gavin M, Zheng Y. Cell. 2006 Jul. 28; 126(2): 253-256).

The endoplasmic reticulum (ER) carries out a variety processes. The ER has a role as both an agonist-sensitive $Ca^{2+}$ store and sink, protein folding/processing takes place within its lumen. Here, numerous $Ca^{2+}$-dependent chaperone proteins ensure that newly synthesized proteins are folded correctly and sent off to the appropriate destination. The ER is also involved in vesicle trafficking, release of stress signals, regulation of cholesterol metabolism, and apoptosis. Many of these processes require intraluminal $Ca^{2+}$, and protein misfolding, ER stress responses, and apoptosis are all likely induced by depleting the ER of Ca2+ for prolonged periods of time. Because of its role as a source of $Ca^{2+}$, it is clear that ER $Ca^{2+}$ content must fall after stimulation. However, to preserve the functional integrity of the ER, it is vital that the $Ca^{2+}$ content does not fall too low or is maintained at a low level. Replenishment of the ER with $Ca^{2+}$ is therefore a central process to all eukaryotic cells. Because a fall in ER $Ca^{2+}$ content activates store-operated $Ca^{2+}$ channels in the plasma membrane, a major function of this $Ca^{2+}$ entry pathway is believed to be maintenance of ER $Ca^{2+}$ levels that are necessary for proper protein synthesis and folding. However, store-operated $Ca^{2+}$ channels have other important roles.

The understanding of store operated calcium entry was provided by electrophysiological studies which established that the process of emptying the stores activated a $Ca^{2+}$ current in mast cells called $Ca^{2+}$ release-activated $Ca^{2+}$ current or $I_{CRAC}$. $I_{CRAC}$ is non-voltage activated, inwardly rectifying, and remarkably selective for $Ca^{2+}$. It is found in several cell types mainly of hemopoietic origin. $I_{CRAC}$ is not the only store-operated current, and it is now apparent that store-operated influx encompasses a family of $Ca^{2+}$-permeable channels, with different properties in different cell types. $I_{CRAC}$ was the first store-operated $Ca^{2+}$ current to be described and remains a popular model for studying store-operated influx.

Store-operated calcium channels are likely activated by any procedure that empties the stores; it does not seem to matter how the stores are emptied, the net effect is activation of store-operated $Ca^{2+}$ entry. Physiologically, store emptying is evoked by an increase in the levels of $IP_3$ or other $Ca^{2+}$-releasing signals followed by $Ca^{2+}$ release from the stores.

But there are several other methods for emptying stores. These methods include the following:
1) elevation of $IP_3$ in the cytosol (following receptor stimulation or, dialyzing the cytosol with $IP_3$ itself or related congeners like the nonmetabolizable analog $Ins(2,4,5)P_3$);
2) application of the $Ca^{2+}$ ionophore ionomycin to permeabilize the ER membrane;
3) dialyzing the cytoplasm with high concentrations of the $Ca^{2+}$ chelators EGTA or BAPTA, which chelate $Ca^{2+}$ that leaks from the stores and hence prevent store refilling;
4) exposure to the sarcoplasmic/endoplasmic reticulum $Ca^{2+}$-ATPase (SERCA) inhibitors like thapsigargin, cyclopiazonic acid, and di-tert-butylhydroquinone which prevent the P-type ATPases from refilling the stores;
5) sensitizing the $IP_3$ receptors to resting levels of $InsP_3$ with agents like thimerosal; and
6) loading membrane-permeable metal $Ca^{2+}$ chelators like N,N,N',N'-tetrakis(2-pyridylmethyl)ethylene diamine (TPEN) directly into the stores.

Through mass action, TPEN lowers free intraluminal $Ca^{2+}$ concentration without changing total store $Ca^{2+}$ such that the store depletion-dependent signal is generated.

These methods of emptying stores are not devoid of potential problems. The key feature of store-operated $Ca^{2+}$ entry is that it is the fall in $Ca^{2+}$ content within the stores and not the subsequent rise in cytoplasmic $Ca^{2+}$ concentration that activates the channels. However, ionomycin and SERCA pump blockers generally cause a rise in cytoplasmic $Ca^{2+}$ concentration as a consequence of store depletion, and such a rise in $Ca^{2+}$ could open $Ca^{2+}$-activated cation channels permeable to $Ca^{2+}$. One way to avoid such problems is to use agents under conditions where cytoplasmic $Ca^{2+}$ has been strongly buffered with high concentrations of $Ca^{2+}$ chelator such as EGTA or BAPTA.

Store-Operated Calcium Entry

The calcium influx mechanism has been referred to as store-operated calcium entry (SOCE). Stromal interaction molecule (STIM) proteins are an essential component of SOC channel function, serving as the sensors for detecting the depletion of calcium from internal stores and for activating SOC channels. As single pass transmembrane protein, however, STIM proteins were unlikely to be responsible by themselves for mediating of $Ca^{2+}$ entry into cells.

Reduced calcium concentration in intracellular calcium stores such as the endoplasmic reticulum resulting from release of calcium therefrom provides a signal for influx of calcium from the extracellular medium into the cell. This influx of calcium, which produces a sustained "plateau" elevation of cytosolic calcium concentration, generally does not rely on voltage-gated plasma membrane channels and does not involve activation of calcium channels by calcium. This calcium influx mechanism is referred to as capacitative calcium entry (CCE), calcium release-activated, store-operated or depletion-operated calcium entry. Store-operated calcium entry is optionally recorded as an ionic current with distinctive properties. This current is referred to as Isoc (store-operated current) or $I_{CRAC}$ (calcium release-activated current).

Electrophysiological analysis of store-operated or calcium release-activated currents reveals distinct biophysical properties of these currents. For example, the current is activated by depletion of intracellular calcium stores (e.g., by non-physiological activators such as thapsigargin, CPA, ionomycin and BAPTA, and physiological activators such as $IP_3$) and are likely selective for divalent cations, such as calcium, over monovalent ions in physiological solutions or conditions, are influenced by changes in cytosolic calcium levels, and generally shows altered selectivity and conductivity in the presence of low extracellular concentrations of divalent cations. The current is also blocked or enhanced by 2-APB (depending on concentration) and blocked by SKF96365 and $Gd^{3+}$ and generally are described as a calcium current that is not strictly voltage-gated.

Patch-clamp studies in mast cells and Jurkat leukaemic T cells have established the CRAC entry mechanism as an ion channel with distinctive biophysical characteristics, including a high selectivity for $Ca^{2+}$ paired with an exceedingly low conductance. Furthermore, the CRAC channel was shown to fulfill the rigorous criteria for being store-operated, which is the activation solely by the reduction of $Ca^{2+}$ in the ER rather than by cytosolic $Ca^{2+}$ or other messengers generated by PLC.

Regulation of Store-Operated Calcium Entry by Intracellular Calcium Stores

Store-operated calcium entry is regulated by the level of calcium within an intracellular calcium store. Intracellular calcium stores are characterized by sensitivity to agents, which are physiological or pharmacological, which activate release of calcium from the stores or inhibit uptake of calcium into the stores. Different cells have been studied in characterization of intracellular calcium stores, and stores have been characterized as sensitive to various agents, including, but not limited to, $IP_3$ and compounds that effect the $IP_3$ receptor, thapsigargin, ionomycin and/or cyclic ADP-ribose (cADPR).

Accumulation of calcium within endoplasmic reticulum and sarcoplasmic reticulum (SR; a specialized version of the endoplasmic reticulum in striated muscle) storage organelles is achieved through sarcoplasmic-endoplasmic reticulum calcium ATPases (SERCAs), commonly referred to as calcium pumps. During signaling (i.e., when endoplasmic reticulum channels are activated to provide for calcium release from the endoplasmic reticulum into the cytoplasm), endoplasmic reticulum calcium is replenished by the SERCA pump with cytoplasmic calcium that has entered the cell from the extracellular medium.

Calcium release channels associated with $IP_3$ and ryanodine receptors provide for controlled release of calcium from endoplasmic and sarcoplasmic reticulum into the cytoplasm resulting in transient increases in cytoplasmic calcium concentration. $IP_3$ receptor-mediated calcium release is triggered by $IP_3$ formed in the break down of plasma membrane phosphoinositides through the action of phospholipase C activated by binding of an agonist to a plasma membrane G protein-coupled receptor. Ryanodine receptor-mediated calcium release is triggered by an increase in cytoplasmic calcium and is referred to as calcium-induced calcium release (CICR). The activity of ryanodine receptors (which have affinity for ryanodine and caffeine) are also be regulated by cyclic ADP-ribose.

Thus, the calcium levels in the stores, and in the cytoplasm, fluctuate. For example, ER free calcium generally decrease from a range of about 60-400 µM to about 1-50 µM when HeLa cells are treated with histamine, an agonist of PLC-linked histamine receptors (Miyawaki et al. (1997) Nature 388:882-887). Store-operated calcium entry is activated as the free calcium concentration of the intracellular stores is reduced. Depletion of store calcium, as well as a concomitant increase in cytosolic calcium concentration, likely thus regulate store-operated calcium entry into cells.

Cytoplasmic Calcium Buffering

Agonist activation of signaling processes in cells generally involve dramatic increases in the calcium permeability of the endoplasmic reticulum, for example, through opening of $IP_3$ receptor channels, and the plasma membrane through store-operated calcium entry. These increases in calcium permeability are associated with an increase in cytosolic calcium concentration that are separated into two components: a "spike" of calcium release from the endoplasmic reticulum during activation of the $IP_3$ receptor and a plateau phase which is a sustained elevation of calcium levels resulting from entry of calcium into the cytoplasm from the extracellular medium. Upon stimulation, the resting intracellular free calcium concentration of about 100 nM generally rise globally to greater than 1 μM. The cell modulates these calcium signals with endogenous calcium buffers, including physiological buffering by organelles such as mitochondria, endoplasmic reticulum and Golgi. Mitochondrial uptake of calcium through a uniporter in the inner membrane is driven by the large negative mitochondrial membrane potential, and the accumulated calcium is released slowly through sodium-dependent and -independent exchangers, and, under some circumstances, the permeability transition pore (PTP). Thus, mitochondria generally act as calcium buffers by taking up calcium during periods of activation and slowly releasing it later. Uptake of calcium into the endoplasmic reticulum is regulated by the sarcoplasmic and endoplasmic reticulum calcium ATPase (SERCA). Uptake of calcium into the Golgi is mediated by a P-type calcium transport ATPase (PMR1/ATP2C1). Additionally, there is evidence that a significant amount of the calcium released upon $IP_3$ receptor activation is extruded from the cell through the action of the plasma membrane calcium ATPase. For example, plasma membrane calcium ATPases provide the dominant mechanism for calcium clearance in human T cells and Jurkat cells, although sodium/calcium exchange also contributes to calcium clearance in human T cells. Within calcium-storing organelles, calcium ions are bound to specialized calcium-buffering proteins, such as, for example, calsequestrins, calreticulins and calnexins. Additionally, there are calcium-buffering proteins in the cytosol that modulate calcium spikes and assist in redistribution of calcium ions. Thus, proteins and other molecules that participate in any of these and other mechanisms through which cytosolic calcium levels are reduced are proteins that are involved in, participate in and/or provide for cytoplasmic calcium buffering. Thus, cytoplasmic calcium buffering allows for sustained calcium influx through SOC channels. Large increases in cytoplasmic $Ca^{2+}$ or store refilling deactivate SOCE.

Downstream Calcium Entry-Mediated Events

In addition to intracellular changes in calcium stores, store-operated calcium entry affects a multitude of events that are consequent to or in addition to the store-operated changes. For example $Ca^{2+}$ influx results in the activation of a large number of calmodulin-dependent enzymes including the serine phosphatase calcineurin. Activation of calcineurin by an increase in intracellular calcium results in acute secretory processes such as mast cell degranulation. Activated mast cells release preformed granules containing histamine, heparin, TNFα and enzymes such as β-hexosaminidase. Some cellular events, such as B and T cell proliferation, require sustained calcineurin signaling, which requires a sustained increase in intracellular calcium. A number of transcription factors are regulated by calcineurin, including NFAT (nuclear factor of activated T cells), MEF2 and NFκB. NFAT transcription factors play important roles in many cell types, including immune cells. In immune cells NFAT mediates transcription of a large number of molecules, including cytokines, chemokines and cell surface receptors. Transcriptional elements for NFAT have been found within the promoters of cytokines such as IL-2, IL-3, IL-4, IL-5, IL-8, IL-13, as well as tumor necrosis factor alpha (TNFα), granulocyte colony-stimulating factor (G-CSF), and gamma-interferon (γ-IFN).

The activity of NFAT proteins is regulated by their phosphorylation level, which in turn is regulated by both calcineurin and NFAT kinases. Activation of calcineurin by an increase in intracellular calcium levels results in dephosphorylation of NFAT and entry into the nucleus. Rephosphorylation of NFAT masks the nuclear localization sequence of NFAT and prevents its entry into the nucleus. Because of its strong dependence on calcineurin-mediated dephosphorylation for localization and activity, NEAT is a sensitive indicator of intracellular calcium levels.

Store Operated Calcium Channels

Clinical studies demonstrate that the CRAC channel, a type of SOC channel, is required for the activation of genes underlying the T cell response to antigen (Partiseti et al., *J. Biol. Chem.*, 269, 32327-32335, 1994; Feske et al, *Curr. Biol.* 15, 1235-1241, 2005). In some embodiments, SOCE contributes directly to the elevation of cytosolic $Ca^{2+}$ levels ($[Ca^{2+}]_i$), as in T lymphocytes where CRAC channels generate the sustained $Ca^{2+}$ signals needed to drive gene expression underlying T cell activation by antigen. Sustained calcium entry is needed for lymphocyte activation and adaptive immune response. Calcium entry into lymphocytes occurs primarily through the CRAC channels. Increased calcium levels lead to NFAT activation and expression of cytokines required for immune response.

The CRAC channel has a distinctive biophysical fingerprint, quantifiable store-dependence, and essential function in T cells. Studies have shown that CRAC channels are formed from two component proteins, which interact to form CRAC channels. The CRAC channel is assembled by two functional components, STIM1 and Orai1. STIM1 (stromal interaction molecule 1) was identified as the mammalian ER $Ca^{24}$ sensor. Orai1/CRACM1 was identified as a component of the mammalian CRAC channel.

STIM1 is the sensor of $Ca^{2+}$ within ER $Ca^{2+}$ stores, moving in response to store depletion into ER puncta close to the plasma membrane. Orai1 is a pore forming CRAC channel subunit in the plasma membrane. The two membrane proteins STIM1 and Orai1 have each been shown to be essential for the activation of CRAC channels.

Expression of both STIM1 and Grail in human embryonic kidney 293 cells (HEK293 cells) reconstitute functional CRAC channels. Expression of Orai1 alone strongly reduces store-operated $Ca^{2+}$ entry in HEK293 cells and the $Ca^{2+}$ release-activated $Ca^{2+}$ current ($I_{CRAC}$) in rat basophilic leukemia cells. However, expressed along with the store-sensing STIM1 protein, Orai1 causes a massive increase in SOCE, enhancing the rate of $Ca^{2+}$ entry by up to 103-fold. This entry is entirely store dependent since the same coexpression causes no measurable store-independent Ca2+ entry. The entry is completely blocked by the store operated channel blocker, 2-aminoethoxydiphenylborate. STIM proteins are thought to mediate $Ca^{2+}$ store-sensing and endoplasmic reticulum-plasma membrane coupling with no intrinsic channel properties. Orai1 contributes the plasma membrane channel component responsible for $Ca^{2+}$ entry. The suppression of CRAC channel function by Orai1 overexpression reflects a required stoichiometry between STIM1 and Orai1.

Stromal Interacting Molecule (STIM) Proteins

In RNAi screen in *Drosophila* S2 cells using thapsigargin-activated $Ca^{2+}$ entry as a marker for store-operated channels, one gene gave a substantially reduced $Ca^{2+}$ entry, coding for the protein stromal interaction molecule (Stim). There are two homologues of Stim in mammalian cells, STIM1 and STIM2, both of which appear to be distributed ubiquitously. STIM1 is the ER Ca$^{2+}$ sensor for store-operated Ca$^{2+}$ entry. STIM1 is a 77 kDa type I membrane protein with multiple predicted protein interaction or signaling domains and is located predominantly in the ER, but also to a limited extent in the plasma membrane.

Knockdown of STIM1 by RNAi substantially reduced I$_{CRAC}$ in Jurkat T cells, and store-operated Ca$^{2+}$ entry in HEK293 epithelial cells and SH-SY5Y neuroblastoma cells. However, knockdown of the closely related STIM2 had no effect. These results indicate an essential role of STIM (Drosophila) and STIM1 (mammals) in the mechanism of activation of store-operated channels. It is unlikely that STIM1 is the store-operated channel itself. It has no channel-like sequence, and overexpression of the protein only modestly enhances Ca$^{2+}$ entry. STIM1 is located both on the plasma and intracellular membranes, such as the ER. Protein sequence analysis lend support that STIM1 spans the membrane once, with its NH$_2$ terminus oriented toward the lumen of the ER or the extracellular space. The NH$_2$ terminus contains an EF-hand domain, and functions as the Ca$^{2+}$ sensor in the ER. The protein also contains protein-protein interaction domains, notably coiled-coiled domains in the cytoplasm and a sterile motif (SAM) in the ER (or extracellular space), both near the predicted transmembrane domain. STIM1 oligomerizes and thus the protein in the ER and plasma membrane could interact bridging the two.

Total internal reflection fluorescence (TIRF) and confocal microscopy reveal that STIM1 is distributed throughout the ER when Ca$^{2+}$ stores are full, but redistributes into discrete puncta near the plasma membrane on store depletion. Although the redistribution of STIM1 into junctional ER regions is slow, it does precede the opening of CRAC channels by several and is therefore rapid enough to be an essential step in the activation of CRAC channels.

Store depletion, e.g. by treatment with thapsigargin, causes the insertion of STIM1 into the plasma membrane where STIM controls store operated calcium entry through the CRAC channels. Further evidence for STIM1 as the Ca$^{2+}$ sensor for SOCE is that mutation of predicted Ca$^{2+}$-binding residues of the EF hand structural motif, expected to reduce its affinity for Ca$^{2+}$ and hence mimic the store-depleted state, causes STIM1 to redistribute spontaneously into puncta and trigger constitutive Ca$^{2+}$ influx through SOCs even when stores are full.

Orai Proteins

Orai1 (also known as CRACM1) is a widely expressed, 33 kDa plasma membrane protein with 4 transmembrane domains and a lack of significant sequence homology to other ion channels.

Studies of T cells from human patients with a severe combined immunodeficiency (SCID) syndrome, in which T cell receptor engagement or store depletion failed to activate Ca$^{2+}$ entry, was shown to be due to a single point mutation in Orai1.

Other mammalian Orai homologues exist, e.g. Orai2 and Orai3, however their function is not clearly defined. Orai2 and Orai3 generally exhibits SOC channel activity when overexpressed with STIM1 in HEK cells.

Evidence that Orai1 contributes to the CRAC channel pore was obtained by Orai1 mutagenesis studies. Selectivity of the CRAC channel for Ca$^{2+}$ ions was shown by mutations at either Glu 106 or Glu 190, which weaken the ability of Ca$^{2+}$ binding in order block permeation of monovalent cations (similar to mechanisms described for voltage-gated Ca$^{2+}$ channels).

Neutralizing the charge on a pair of aspartates in the I-II loop (Asp 110 and Asp 112) reduces block by Gd$^{3+}$ and block of outward current by extracellular Ca$^{2+}$, indicating that these negatively charged sites promote accumulation of polyvalent cations near the mouth of the pore.

Currents observed through overexpression of Orai1 closely resemble I$_{CRAC}$, and the fact that Orai1 generally form multimers, it is likely that the native CRAC channel is either a multimer of Orai1 alone or in combination with the closely related subunits Orai2 and/or Orai3.

Functional Store Operated Calcium Channels

The characterization of SOC channels has been largely obtained by one type of SOC channel, the CRAC channel. CRAC channel activity is triggered by the loss of Ca$^{2+}$ from the ER lumen, which is coupled to the opening of CRAC channels in the plasma membrane through the actions of STIM1 and Orai1. Depletion of Ca$^{2+}$ is sensed by STIM1, causing it to accumulate in junctional ER adjacent to the plasma membrane. In a TIRF-based Ca$^{2+}$-imaging study to map the locations of open CRAC channels, [Ca$^{2+}$]$_i$ elevations were seen to co-localize with STIM1 puncta, showing directly that CRAC channels open only in extreme proximity to these sites.

In cells co-expressing both STIM1 and Orai1, store depletion causes Orai1 itself to move from a dispersed distribution to accumulate in the plasma membrane directly opposite STIM1, enabling STIM1 to activate the channel. Thus, CRAC channels are formed by apposed clusters of STIM1 in the ER and Orai1 in the plasma membrane, separated by a narrow gap of cytosol. The junctional gap (about 10-25 nm) is likely small enough to permit protein-protein interactions. This is supported by the fact that overexpressed STIM1 and Orai1 have been co-immunoprecipitated.

Thus, STIM1 and Orai1 interact either directly or as members of a multiprotein complex. Support for this was observed when the expression of the cytosolic portion of STIM1 by itself was sufficient to activate CRAC channels in one study, and the effects of deleting the ERM/coiled-coil and other C-terminal domains point to roles in STIM1 clustering and SOC channel activation. On the luminal side of STIM1, the isolated EF-SAM region forms dimers and higher-order multimers on removal of Ca$^{2+}$ in vitro, indicating that STIM1 oligomerization is likely an early step in store operated calcium activation.

Compounds disclosed herein that are capable of modulating a STIM protein and/or an Orai protein such as, inhibition or reduction of SOCE and/or I$_{CRAC}$. In some embodiments, the modulation by compounds disclosed herein that are capable of modulating intracellular calcium levels result from a variety of effects, such as, but not limited to, binding to a protein, interaction with a protein, or modulation of interactions, activities, levels or any physical, structural or other property of a protein involved in modulating intracellular calcium (e.g. a STIM protein and/or Orai protein).

For example, methods for assessing binding or interaction of a test agent with a protein involved in modulating a STIM protein and/or an Orai protein include NMR, mass spectroscopy, fluorescence spectroscopy, scintillation proximity assays, surface plasmon resonance assays and others. Examples of methods for assessing modulation of interactions, activities, levels or any physical, structural or other property of a protein involved in modulating a STIM protein and/or an Orai protein include, but are not limited to, FRET assays to assess effects on protein interactions, NMR, X-ray crystallography and circular dichroism to assess effects on protein interactions and on physical and structural properties of a protein, and activity assays suitable for assessing a particular activity of a protein.

Monitoring or Assessing Effects on Intracellular Calcium

In some embodiments, monitoring or assessing the effect of compounds or agents on intracellular calcium in any of the screening/identification methods described herein, a direct or indirect evaluation or measurement of cellular (including cytosolic and intracellular organelle or compartment) calcium and/or movement of ions into, within or out of a cell, organelle, calcium store or portions thereof (e.g., a membrane) are conducted. A variety of methods are described herein for evaluating calcium levels and ion movements or flux. The particular method used and the conditions employed depend on whether a particular aspect of intracellular calcium is being monitored or assessed. For example, in some embodiments described herein, reagents and conditions are used for specifically evaluating store-operated calcium entry, resting cytosolic calcium levels, calcium buffering and calcium levels and uptake by or release from intracellular organelles and calcium stores. In other embodiments, the effect of a compound or agent on intracellular calcium is monitored or assessed using, for example, a cell, an intracellular organelle or calcium storage compartment, a membrane (including, e.g., a detached membrane patch or a lipid bilayer) or a cell-free assay system (e.g., outside-out membrane vesicle). Generally, some aspect of intracellular calcium is monitored or assessed in the presence of test agent and compared to a control, e.g., intracellular calcium in the absence of test agent.

Methods of Modulating Intracellular Calcium

In some embodiments, modulation of intracellular calcium is any alteration or adjustment in intracellular calcium including but not limited to alteration of calcium concentration or level in the cytoplasm and/or intracellular calcium storage organelles, e.g., endoplasmic reticulum, alteration in the movement of calcium into, out of and within a cell or intracellular calcium store or organelle, alteration in the location of calcium within a cell, and alteration of the kinetics, or other properties, of calcium fluxes into, out of and within cells. In some embodiments, intracellular calcium modulation involves alteration or adjustment, e.g. reduction or inhibition, of store-operated calcium entry, cytosolic calcium buffering, calcium levels in or movement of calcium into, out of or within an intracellular calcium store or organelle, and/or basal or resting cytosolic calcium levels. In some embodiments, modulation of intracellular calcium involves an alteration or adjustment in receptor-mediated ion (e.g., calcium) movement, second messenger-operated ion (e.g., calcium) movement, calcium influx into or efflux out of a cell, and/or ion (e.g., calcium) uptake into or release from intracellular compartments, including, for example, endosomes and lysosomes.

In one aspect, compounds described herein modulate intracellular calcium, such as but not limited to, modulation (e.g. reduction or inhibition) of SOC channel activity, such as inhibition of CRAC channel activity (e.g. inhibition of $I_{CRAC}$, inhibition of SOCE), in an immune system cell (e.g., a lymphocyte, white blood cell, T cell, B cell), a fibroblast (or a cell derived from a fibroblast), or an epidermal, dermal or skin cell (e.g., a keratinocyte). In some embodiments, the step of modulating one or more proteins involved in modulating intracellular calcium (e.g. a STIM protein and/or Orai protein) involves, for example, reducing the level, expression of, an activity of, function of and/or molecular interactions of a protein. For instance, if a cell exhibits an increase in calcium levels or lack of regulation of an aspect of intracellular calcium modulation, e.g., store-operated calcium entry, then in other embodiments, modulating involves reducing the level of, expression of, an activity or function of, or a molecular interaction of a protein, e.g. a STIM protein and/or Orai protein.

Compounds

Compounds described herein modulate intracellular calcium and are used in the treatment of diseases, disorders or conditions where modulation of intracellular calcium has a beneficial effect. In one embodiment, compounds described herein inhibit store operated calcium entry. In one embodiment, compounds capable of modulating intracellular calcium levels interrupt the assembly of SOCE units. In another embodiment, compounds capable of modulating intracellular calcium levels alter the functional interactions of proteins that form store operated calcium channel complexes. In one embodiment, compounds capable of modulating intracellular calcium levels alter the functional interactions of STIM1 with Orai1. In other embodiments, compounds capable of modulating intracellular calcium levels are SOC channel pore blockers. In other embodiments, compounds capable of modulating intracellular calcium levels are CRAC channel pore blockers.

In one aspect, compounds capable of modulating intracellular calcium levels inhibit the electrophysiological current ($I_{SOC}$) directly associated with activated SOC channels. In one aspect, compounds capable of modulating intracellular calcium levels inhibit the electrophysiological current ($I_{CRAC}$) directly associated with activated CRAC channels.

In other embodiments, the diseases, conditions or disorders that benefit from modulation of intracellular calcium include, but are not limited to, an immune system-related disease (e.g., an autoimmune disease), a disease or disorder involving inflammation (e.g., asthma, chronic obstructive pulmonary disease, rheumatoid arthritis, inflammatory bowel disease, glomerulonephritis, neuroinflammatory diseases, multiple sclerosis, and disorders of the immune system), cancer or other proliferative disease, kidney disease and liver disease. In one embodiment, compounds described herein are used as immunosuppressants to prevent transplant graft rejections, allogeneic or xenogeneic transplantation rejection (organ, bone marrow, stem cells, other cells and tissues), graft-versus-host disease. In other embodiments, transplant graft rejections result from tissue or organ transplants. In further embodiments, graft-versus-host disease results from bone marrow or stem cell transplantation.

Compounds described herein modulate an activity of, modulate an interaction of, or binds to, or interacts with at least one portion of a protein in the store operated calcium channel complex. In one embodiment, compounds described herein modulate an activity of, modulate an interaction of, or binds to, or interacts with at least one portion of a protein in the calcium release activated calcium channel complex. In one embodiment, compounds described herein reduce the level of functional store operated calcium channel complexes. In one embodiment, compounds described herein reduce the level of activated store operated calcium channel complexes. In one embodiment, store operated calcium channel complexes are calcium release activated calcium channel complexes.

Compounds capable of modulating intracellular calcium levels for treatment of a disease or disorder, when administered to a subject having a disease or disorder effectively reduces, ameliorates or eliminates a symptom or manifestation of the disease, condition or disorder. In other embodiments, compounds described herein also are administered to a subject predisposed to a disease, condition or disorder that does not yet manifest a symptom of the disease, condition or disorder, prevents or delays development of the symptoms. In further embodiments, the agent has such effects alone or in combination with other agents, or functions to enhance a therapeutic effect of another agent.

Diseases, Disorders or Conditions

Clinical studies demonstrate that the CRAC channel is absolutely required for the activation of genes underlying the T cell response to antigen. Sustained calcium entry is needed for lymphocyte activation and adaptive immune response. Calcium entry into lymphocytes occurs primarily through the CRAC channels. Increased calcium leads to NFAT activation and expression of cytokines required for immune response. Inhibiting the store operated calcium entry is an efficient way to prevent T cell activation.

Inhibition of CRAC channel activity with the compounds that modulate intracellular calcium levels provide a means for providing immunosuppressive therapy as demonstrated by the elimiation of store-operated calcium entry noted in patients with severe-combined immunodeficiency (SCID). T cells, fibroblasts, and in some cases B cells, from patients with T cell immunodeficiency or SCID having a principal defect in T cell activation show a strong defect in store-operated calcium entry. SCID patients lack adaptive immune response, but without any impairment or toxicity in major organs. The SCID patient phenotype indicates that inhibition of CRAC channels is an effective strategy for immunosuppression.

Diseases/Disorders Involving Inflammation and Diseases/Disorders Related to the Immune System In some embodiments, diseases, disorders or conditions that are treated or prevented using compounds disclosed herein that are capable of modulating intracellular calcium levels, compositions thereof, and methods provided herein to identify compounds capable of modulating intracellular calcium levels, include diseases, conditions or disorders involving inflammation and/or that are related to the immune system. These diseases include but are not limited to asthma, chronic obstructive pulmonary disease, rheumatoid arthritis, inflammatory bowel disease, glomerulonephritis, neuroinflammatory diseases such as multiple sclerosis, and disorders of the immune system.

The activation of neutrophils (PMN) by inflammatory mediators is partly achieved by increasing cytosolic calcium concentration. Store-operated calcium influx in particular is thought to play an important role in PMN activation. It has been shown that trauma increases PMN store-operated calcium influx and that prolonged elevations of cytosolic calcium concentration due to enhanced store-operated calcium influx likely alters stimulus-response coupling to chemotaxins and contribute to PMN dysfunction after injury. Modulation of PMN cytosolic calcium concentration through store-operated calcium channels might therefore be useful in regulating PMN-mediated inflammation and spare cardiovascular function after injury, shock or sepsis.

Calcium plays a critical role in lymphocyte activation. Activation of lymphocytes, e.g., by antigen stimulation, results in rapid increases in intracellular free calcium concentrations and activation of transcription factors, including nuclear factor of activated T cells (NFAT), NF-κB, JNK1, MEF2 and CREB. NFAT is a key transcriptional regulator of the IL-2 (and other cytokine) genes. A sustained elevation of intracellular calcium level is required to keep NFAT in a transcriptionally active state, and is dependent on store-operated calcium entry. Reduction or blocking of store-operated calcium entry in lymphocytes blocks calcium-dependent lymphocyte activation. Thus, in some embodiments, modulation of a STIM protein and/or an Orai protein, and particularly store-operated calcium entry (e.g., reduction in, elimination of store-operated calcium entry), in lymphocytes is a method for treating immune and immune-related disorders, including, for example, chronic immune diseases/disorders, acute immune diseases/disorders, autoimmune and immunodeficiency diseases/disorders, diseases/disorders involving inflammation, organ transplant graft rejections and graft-versus-host disease and altered (e.g., hyperactive) immune responses. For example, in some embodiments treatment of an automimmune disease/disorder involves reducing, blocking or eliminating store-operated calcium entry in lymphocytes.

Examples of immune disorders include psoriasis, rheumatoid arthritis, vasculitis, inflammatory bowel disease, dermatitis, osteoarthritis, asthma, inflammatory muscle disease, allergic rhinitis, vaginitis, interstitial cystitis, scleroderma, osteoporosis, eczema, allogeneic or xenogeneic transplantation (organ, bone marrow, stem cells and other cells and tissues) graft rejection, graft-versus-host disease, lupus erythematosus, inflammatory disease, type I diabetes, pulmonary fibrosis, dermatomyositis, Sjogren's syndrome, thyroiditis (e.g., Hashimoto's and autoimmune thyroiditis), myasthenia gravis, autoinmuune hemolytic anemia, multiple sclerosis, cystic fibrosis, chronic relapsing hepatitis, primary biliary cirrhosis, allergic conjunctivitis and atopic dermatitis.

Cancer and Other Proliferative Diseases

In other embodiments, compounds disclosed herein that are capable of modulating intracellular calcium levels, compositions thereof, and methods provided herein to identify compounds capable of modulating intracellular calcium levels, are used in connection with treatment of malignancies, including, but not limited to, malignancies of lymphoreticular origin, bladder cancer, breast cancer, colon cancer, endometrial cancer, head and neck cancer, lung cancer, melanoma, ovarian cancer, prostate cancer and rectal cancer. Store-operated calcium entry is thought to play an important role in cell proliferation in cancer cells.

Inhibition of SOCE is sufficient to prevent tumor cell proliferation. The pyrazole derivative BTP-2, a direct $I_{CRAC}$ blocker inhibits SOCE and proliferation in Jurkat cells and in colon cancer cells. Moreover, sustained SOCE requires mitochondrial $Ca^{2+}$ uptake and that prevention of mitochondrial $Ca^{2+}$ uptake leads to SOCE inhibition. Stimulation of Jurkat cells induces sustained SOCE and activation of the $Ca^{2+}$-dependent phosphatase calcineurin that dephosphorylates NFAT, promoting expression of interleukin-2 and proliferation. In other embodiments, compounds capable of modulating intracellular calcium levels inhibit SOCE and are used in the treatment of cancer or other proliferative diseases or conditions.

Liver Diseases and Disorders

In some embodiments, diseases, disorders or conditions that are treated or prevented using compounds disclosed herein that are capable of modulating intracellular calcium levels, compositions thereof, and methods provided herein to identify compounds capable of modulating intracellular calcium levels, include hepatic or liver diseases and disorders. These diseases, conditions or disorders include but are not limited to liver injury, for example, due to transplantation, hepatitis and cirrhosis.

Store-operated calcium entry has been implicated in chronic liver disease as well as transplantation injury after cold preservation-warm deoxygenation.

Kidney Diseases and Disorders

In some embodiments, diseases, conditions or disorders that are treated or prevented using the compounds disclosed herein that are capable of modulating intracellular calcium levels, compositions thereof, and methods provided herein to identify compounds capable of modulating intracellular calcium levels, include kidney or renal diseases and disorders. Mesangial cell hyperplasia is often a key feature of such diseases and disorders. In other embodiments, such diseases and disorders are caused by immunological or other mechanisms of injury, including IgAN, membranoproliferative glomerulonephritis or lupus nephritis. Imbalances in the control of mesangial cell replication also appear to play a key role in the pathogenesis of progressive renal failure.

The turnover of mesangial cells in normal adult kidney is very low with a renewal rate of less than 1%. A prominent feature of glomerular/kidney diseases is mesangial hyperplasia due to elevated proliferation rate or reduced cell loss of mesangial cells. When mesangial cell proliferation is induced without cell loss, for example due to mitogenic stimulation, mesangioproliferative glomerulonephritis does result. Data have indicated that regulators of mesangial cell growth, particularly growth factors, are thought to act by regulating store-operated calcium channels. In yet other embodiments, modulators of store-operated calcium influx aids in the treatment of glomerular diseases by inhibiting mesangial cell proliferation.

Examples of Pharmaceutical Compositions and Methods of Administration

Pharmaceutical compositions are formulated in a conventional manner using one or more physiologically acceptable carriers including excipients and auxiliaries which facilitate processing of the active compounds into preparations which are used pharmaceutically. Proper formulation is dependent upon the route of administration chosen. In some embodiments, a summary of pharmaceutical compositions described herein are found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999).

A pharmaceutical composition, as used herein, refers to a mixture of a compound capable of modulating intracellular calcium levels as described herein, with other chemical components, such as carriers, stabilizers, diluents, dispersing agents, suspending agents, thickening agents, and/or excipients. The pharmaceutical composition facilitates administration of the compound to an organism. In practicing the methods of treatment or use provided herein, therapeutically effective amounts of compounds described herein are administered in a pharmaceutical composition to a mammal having a disease, disorder, or condition to be treated. In some embodiments, the mammal is a human. In some embodiments, a therapeutically effective amount varies widely depending on the severity of the disease, the age and relative health of the subject, the potency of the compound used and other factors. In some embodiments, the compounds capable of modulating intracellular calcium levels are used singly or in combination with one or more therapeutic agents as components of mixtures (as in combination therapy).

In further embodiments, the pharmaceutical formulations described herein are administered to a subject by multiple administration routes, including but not limited to, oral, parenteral (e.g., intravenous, subcutaneous, intramuscular), intranasal, buccal, topical, rectal, or transdermal administration routes. Moreover, in some embodiments, the pharmaceutical compositions described herein, which include a compound capable of modulating intracellular calcium levels described herein, are formulated into any suitable dosage form, including but not limited to, aqueous oral dispersions, liquids, gels, syrups, elixirs, slurries, suspensions, aerosols, controlled release formulations, fast melt formulations, effervescent formulations, lyophilized formulations, tablets, powders, pills, dragees, capsules, delayed release formulations, extended release formulations, pulsatile release formulations, multiparticulate formulations, and mixed immediate release and controlled release formulations.

In some embodiments, the compounds and/or compositions are administered in a local rather than systemic manner, for example, via injection of the compound directly into an organ or tissue, often in a depot preparation or sustained release formulation. In other embodiments, such long acting formulations are administered by implantation (for example subcutaneously or intramuscularly) or by intramuscular injection. Furthermore, in some embodiments, the drug is administered in a targeted drug delivery system, for example, in a liposome coated with organ-specific antibody. The liposomes will be targeted to and taken up selectively by the organ. In some embodiments, the drug is provided in the form of a rapid release formulation, in the form of an extended release formulation, or in the form of an intermediate release formulation.

In some embodiments, pharmaceutical compositions including a compound described herein is manufactured in a conventional manner, such as, by way of example only, by means of conventional mixing, dissolving, granulating, dragee-making, levigating, emulsifying, encapsulating, entrapping or compression processes.

The pharmaceutical compositions will include at least one compound capable of modulating intracellular calcium levels described herein, as an active ingredient in free-acid or free-base form, or in a pharmaceutically acceptable salt form. In addition, the methods and pharmaceutical compositions described herein include the use of crystalline forms (also known as polymorphs), as well as active metabolites of these compounds having the same type of activity.

In certain embodiments, compositions provided herein also include one or more preservatives to inhibit microbial activity. Suitable preservatives include quaternary ammonium compounds such as benzalkonium chloride, cetyltrimethylammonium bromide and cetylpyridinium chloride.

In some embodiments, pharmaceutical preparations for oral use are obtained by mixing one or more solid excipient with one or more of the compounds described herein, optionally grinding the resulting mixture, and processing the mixture of granules, after adding suitable auxiliaries, if desired, to obtain tablets, pills, or capsules. Suitable excipients include, for example, fillers such as sugars, including lactose, sucrose, mannitol, or sorbitol; cellulose preparations such as, for example, maize starch, wheat starch, rice starch, potato starch, gelatin, gum tragacanth, methylcellulose, microcrystalline cellulose, hydroxypropylmethylcellulose, sodium carboxymethylcellulose; or others such as: polyvinylpyrrolidone (PVP or povidone) or calcium phosphate. In other embodiments, disintegrating agents are added, such as the cross-linked croscarmellose sodium, polyvinylpyrrolidone, agar, or alginic acid or a salt thereof such as sodium alginate.

Dragee cores are provided with suitable coatings. For this purpose, in some embodiments, concentrated sugar solutions are used, which optionally contain gum arabic, talc, polyvinylpyrrolidone, carbopol gel, polyethylene glycol, and/or titanium dioxide, lacquer solutions, and suitable organic solvents or solvent mixtures. In some embodiments, dyestuffs or pigments are added to the tablets or dragee coatings for identification or to characterize different combinations of active compound doses.

In further embodiments, pharmaceutical preparations that are used orally include push-fit capsules made of gelatin, as well as soft, sealed capsules made of gelatin and a plasticizer, such as glycerol or sorbitol. In some embodiments, the push-fit capsules contain the active ingredients in admixture with filler such as lactose, binders such as starches, and/or lubricants such as talc or magnesium stearate and, optionally, stabilizers. In some embodiments, are soft capsules, wherein the active compounds are dissolved or suspended in suitable liquids, such as fatty oils, liquid paraffin, or liquid polyethylene glycols. In some embodiments, stabilizers are added.

In some embodiments, the solid dosage forms disclosed herein are in the form of a tablet, (including a suspension tablet, a fast-melt tablet, a bite-disintegration tablet, a rapid-disintegration tablet, an effervescent tablet, or a caplet), a pill a powder (including a sterile packaged powder, a dispensable powder, or an effervescent powder), a capsule (including both soft or hard capsules, e.g., capsules made from animal-derived gelatin or plant-derived HPMC, or "sprinkle capsules"), solid dispersion, solid solution, bioerodible dosage form, controlled release formulations, pulsatile release dosage forms, multiparticulate dosage forms, pellets, granules, or an aerosol. In other embodiments, the pharmaceutical formulation is in the form of a powder. In still other embodiments, the pharmaceutical formulation is in the form of a tablet, including but not limited to, a fast-melt tablet. Additionally, pharmaceutical formulations of the compounds described herein are administered as a single capsule or in multiple capsule dosage form. In some embodiments, the pharmaceutical formulation is administered in two, or three, or four, capsules or tablets.

In some embodiments, solid dosage forms, e.g., tablets, effervescent tablets, and capsules, are prepared by mixing particles of a compound capable of modulating intracellular calcium levels described herein, with one or more pharmaceutical excipients to form a bulk blend composition. When referring to these bulk blend compositions as homogeneous, it is meant that the particles of the compound capable of modulating intracellular calcium levels described herein, are dispersed evenly throughout the composition so that the composition are readily subdivided into equally effective unit dosage forms, such as tablets, pills, and capsules. In some embodiments, the individual unit dosages also include film coatings, which disintegrate upon oral ingestion or upon contact with diluent. In further embodiments, these formulations are manufactured by conventional pharmacological techniques.

In some embodiments, the pharmaceutical solid dosage forms described herein include a compound capable of modulating intracellular calcium levels described herein, and one or more pharmaceutically acceptable additives such as a compatible carrier, binder, filling agent, suspending agent flavoring agent, sweetening agent, disintegrating agent, dispersing agent, surfactant, lubricant, colorant, diluent, solubilizer, moistening agent, plasticizer, stabilizer, penetration enhancer, wetting agent, anti-foaming agent, antioxidant, preservative, or one or more combination thereof. In still other embodiments, using standard coating procedures, such as those described in Remington's Pharmaceutical Sciences, 20th Edition (2000), a film coating is provided around the formulation of the compound described herein. In one embodiment, some or all of the particles of the compound described herein are coated. In another embodiment, some or all of the particles of the compound described herein are microencapsulated. In still another embodiment, the particles of the compound described herein are not microencapsulated and are uncoated.

Suitable carriers for use in the solid dosage forms described herein include, but are not limited to, acacia, gelatin, colloidal silicon dioxide, calcium glycerophosphate, calcium lactate, maltodextrin, glycerine, magnesium silicate, sodium caseinate, soy lecithin, sodium chloride, tricalcium phosphate, dipotassium phosphate, sodium stearoyl lactylate, carrageenan, monoglyceride, diglyceride, pregelatinized starch, hydroxypropylmethylcellulose, hydroxypropylmethylcellulose acetate stearate, sucrose, microcrystalline cellulose, lactose, mannitol and the like.

Suitable filling agents for use in the solid dosage forms described herein include, but are not limited to, lactose, calcium carbonate, calcium phosphate, dibasic calcium phosphate, calcium sulfate, microcrystalline cellulose, cellulose powder, dextrose, dextrates, dextran, starches, pregelatinized starch, hydroxypropylmethycellulose (HPMC), hydroxypropylmethycellulose phthalate, hydroxypropylmethylcellulose acetate stearate (HPMCAS), sucrose, xylitol, lactitol, mannitol, sorbitol, sodium chloride, polyethylene glycol, and the like.

In order to release compounds capable of modulating intracellular calcium levels as described herein, from a solid dosage form matrix as efficiently as possible, disintegrants are often used in the formulation, especially when the dosage forms are compressed with binder. Disintegrants help rupturing the dosage form matrix by swelling or capillary action when moisture is absorbed into the dosage form. Suitable disintegrants for use in the solid dosage forms described herein include, but are not limited to, natural starch such as corn starch or potato starch, a pregelatinized starch such as National 1551 or Amijel®, or sodium starch glycolate such as Promogel® or Explotab®, a cellulose such as a wood product, methylcrystalline cellulose, e.g., Avicel®, Avicel® PH101, Avicel® PH102, Avicel® PH105, Elcema® P100, Emcocel®, Vivacel®, Ming Tia®, and Solka-Floc®, methylcellulose, croscarmellose, or a cross-linked cellulose, such as cross-linked sodium carboxymethylcellulose (Ac-Di-Sol®), cross-linked caboxymethylcellulose, or cross-linked croscarmellose, a cross-linked starch such as sodium starch glycolate, a cross-linked polymer such as crospovidone, a cross-linked polyvinylpyrrolidone, alginate such as alginic acid or a salt of alginic acid such as sodium alginate, a clay such as Veegum® HV (magnesium aluminum silicate), a gum such as agar, guar, locust bean, Karaya, pectin, or tragacanth, sodium starch glycolate, bentonite, a natural sponge, a surfactant, a resin such as a cation-exchange resin, citrus pulp, sodium lauryl sulfate, sodium lauryl sulfate in combination starch, and the like.

Binders impart cohesiveness to solid oral dosage form formulations: for powder filled capsule formulation, they aid in plug formation that in some embodiments, are filled into soft or hard shell capsules and for tablet formulation, they ensure the tablet remaining intact after compression and help assure blend uniformity prior to a compression or fill step. Materials suitable for use as binders in the solid dosage forms described herein include, but are not limited to, carboxymethylcellulose, methylcellulose (e.g., Methocel®), hydroxypropylmethylcellulose (e.g. Hypromellose USP Pharmacoat-603, hydroxypropylmethylcellulose acetate stearate (Aqoate HS-LF and HS), hydroxyethylcellulose, hydroxypropylcellulose (e.g., Klucel®), ethylcellulose (e.g., Ethocel®), and microcrystalline cellulose (e.g., Avicel®), microcrystalline dextrose, amylose, magnesium aluminum silicate, polysaccharide acids, bentonites, gelatin, polyvinylpyrrolidone/vinyl acetate copolymer, crospovidone, povidone, starch, pregelatinized starch, tragacanth, dextrin, a sugar, such as sucrose (e.g., Dipac®), glucose, dextrose, molasses, mannitol, sorbitol, xylitol (e.g., Xylitab®), lactose, a natural or synthetic gum such as acacia, tragacanth, ghatti gum, mucilage of isapol husks, starch, polyvinylpyrrolidone (e.g., Povidone® CL, Kollidon® CL, Polyplasdone® XL-10, and Povidone® K-12), larch arabogalactan, Veegum®, polyethylene glycol, waxes, sodium alginate, and the like.

In general, binder levels of about 20 to about 70% are used in powder-filled gelatin capsule formulations. In some embodiments, binder usage level in tablet formulations varies whether direct compression, wet granulation, roller compaction, or usage of other excipients such as fillers which itself act as moderate binder. In some embodiments, are tablet formulations comprising binder usage levels of up to about 70%.

Suitable lubricants or glidants for use in the solid dosage forms described herein include, but are not limited to, stearic acid, calcium hydroxide, talc, corn starch, sodium stearyl fumerate, alkali-metal and alkaline earth metal salts, such as aluminum, calcium, magnesium, zinc, stearic acid, sodium stearates, magnesium stearate, zinc stearate, waxes, Stearowet®, boric acid, sodium benzoate, sodium acetate, sodium chloride, leucine, a polyethylene glycol or a methoxypolyethylene glycol such as Carbowax®, PEG 4000, PEG 5000, PEG 6000, propylene glycol, sodium oleate, glyceryl behenate, glyceryl palmitostearate, glyceryl benzoate, magnesium or sodium lauryl sulfate, and the like.

Suitable diluents for use in the solid dosage forms described herein include, but are not limited to, sugars (including lactose, sucrose, and dextrose), polysaccharides (including dextrates and maltodextrin), polyols (including mannitol, xylitol, and sorbitol), cyclodextrins and the like.

Suitable wetting agents for use in the solid dosage forms described herein include, for example, oleic acid, glyceryl monostearate, sorbitan monooleate, sorbitan monolaurate, triethanolamine oleate, polyoxyethylene sorbitan monooleate, polyoxyethylene sorbitan monolaurate, quaternary ammonium compounds (e.g., Polyquat 10®), sodium oleate, sodium lauryl sulfate, magnesium stearate, sodium docusate, triacetin, vitamin E TPGS and the like.

Suitable surfactants for use in the solid dosage forms described herein include, for example, sodium lauryl sulfate, sorbitan monooleate, polyoxyethylene sorbitan monooleate, polysorbates, polaxomers, bile salts, glyceryl monostearate, copolymers of ethylene oxide and propylene oxide, e.g., Pluronic® (BASF), and the like.

Suitable suspending agents for use in the solid dosage forms described here include, but are not limited to, polyvinylpyrrolidone, e.g., polyvinylpyrrolidone K12, polyvinylpyrrolidone K17, polyvinylpyrrolidone K25, or polyvinylpyrrolidone K30, polyethylene glycol, e.g., in some embodiments, the polyethylene glycol has a molecular weight of about 300 to about 6000, or about 3350 to about 4000, or about 5400 to about 7000, vinyl pyrrolidone/vinyl acetate copolymer (S630), sodium carboxymethylcellulose, methylcellulose, hydroxy-propylmethylcellulose, polysorbate-80, hydroxyethylcellulose, sodium alginate, gums, such as, e.g., gum tragacanth and gum acacia, guar gum, xanthans, including xanthan gum, sugars, cellulosics, such as, e.g., sodium carboxymethylcellulose, methylcellulose, sodium carboxymethylcellulose, hydroxypropylmethylcellulose, hydroxyethylcellulose, polysorbate-80, sodium alginate, polyethoxylated sorbitan monolaurate, polyethoxylated sorbitan monolaurate, povidone and the like.

Suitable antioxidants for use in the solid dosage forms described herein include, for example, e.g., butylated hydroxytoluene (BHT), sodium ascorbate, and tocopherol.

It should be appreciated that there is considerable overlap between additives used in the solid dosage forms described herein. Thus, the above-listed additives should be taken as merely exemplary, and not limiting, of the types of additives that are included in solid dosage forms of the pharmaceutical compositions described herein.

In other embodiments, one or more layers of the pharmaceutical formulation are plasticized. Illustratively, a plasticizer is generally a high boiling point solid or liquid. In some embodiments, suitable plasticizers are added from about 0.01% to about 50% by weight (w/w) of the coating composition. Plasticizers include, but are not limited to, diethyl phthalate, citrate esters, polyethylene glycol, glycerol, acetylated glycerides, triacetin, polypropylene glycol, polyethylene glycol, triethyl citrate, dibutyl sebacate, stearic acid, steatol, stearate, and castor oil.

Compressed tablets are solid dosage forms prepared by compacting the bulk blend of the formulations described above. In various embodiments, compressed tablets which are designed to dissolve in the mouth will include one or more flavoring agents. In other embodiments, the compressed tablets will include a film surrounding the final compressed tablet. In some embodiments, the film coating provides a delayed release of the compounds capable of modulating intracellular calcium levels described herein from the formulation. In other embodiments, the film coating aids in patient compliance (e.g., Opadry® coatings or sugar coating). Film coatings including Opadry® typically range from about 1% to about 3% of the tablet weight. In other embodiments, the compressed tablets include one or more excipients.

In some embodiments, a capsule is prepared, for example, by placing the bulk blend of the formulation of the compound described above, inside of a capsule. In some embodiments, the formulations (non-aqueous suspensions and solutions) are placed in a soft gelatin capsule. In other embodiments, the formulations are placed in standard gelatin capsules or non-gelatin capsules such as capsules comprising HPMC. In other embodiments, the formulation is placed in a sprinkle capsule, wherein the capsule is swallowed whole or the capsule is opened and the contents sprinkled on food prior to eating. In some embodiments, the therapeutic dose is split into multiple (e.g., two, three, or four) capsules. In some embodiments, the entire dose of the formulation is delivered in a capsule form.

In various embodiments, the particles of the compounds capable of modulating intracellular calcium levels described herein and one or more excipients are dry blended and compressed into a mass, such as a tablet, having a hardness sufficient to provide a pharmaceutical composition that substantially disintegrates within less than about 30 minutes, less than about 35 minutes, less than about 40 minutes, less than about 45 minutes, less than about 50 minutes, less than about 55 minutes, or less than about 60 minutes, after oral administration, thereby releasing the formulation into the gastrointestinal fluid.

In another formulation, dosage forms include microencapsulated formulations. In some embodiments, one or more other compatible materials are present in the microencapsulation material. Exemplary materials include, but are not limited to, pH modifiers, erosion facilitators, anti-foaming agents, antioxidants, flavoring agents, and carrier materials such as binders, suspending agents, disintegration agents, filling agents, surfactants, solubilizers, stabilizers, lubricants, wetting agents, and diluents.

Materials useful for the microencapsulation described herein include materials compatible with compounds described herein, which sufficiently isolate the compound from other non-compatible excipients. Materials compatible with compounds capable of modulating intracellular calcium levels described herein are those that delay the release of the compounds capable of modulating intracellular calcium levels in vivo.

Exemplary microencapsulation materials useful for delaying the release of the formulations including compounds described herein, include, but are not limited to, hydroxypropyl cellulose ethers (HPC) such as Klucel® or Nisso HPC, low-substituted hydroxypropyl cellulose ethers (L-HPC), hydroxypropyl methyl cellulose ethers (HPMC) such as Seppifilm-LC, Pharmacoat®, Metolose SR, Methocel®-E, Opadry YS, PrimaFlo, Benecel MP824, and Benecel MP843, methylcellulose polymers such as Methocele-A, hydroxypropylmethylcellulose acetate stearate Aqoat (HF-LS, HF-LG, HF-MS) and Metolose®, Ethylcelluloses (EC) and mixtures thereof such as E461, Ethocel®, Aqualon®-EC, Surelease®, Polyvinyl alcohol (PVA) such as Opadry AMB, hydroxyethylcelluloses such as Natrosol®, carboxymethylcelluloses and salts of carboxymethylcelluloses (CMC) such as Aqualon®-CMC, polyvinyl alcohol and polyethylene glycol co-polymers such as Kollicoat IR®, monoglycerides (Myverol), triglycerides (KLX), polyethylene glycols, modified food starch, acrylic polymers and mixtures of acrylic polymers with cellulose ethers such as Eudragit® EPO, Eudragit® L30D-55, Eudragit® FS 30D Eudragit® L100-55, Eudragit® L100, Eudragit® S100, Eudragit® RD100, Eudragit® E100, Eudragit® L12.5, Eudragit® S12.5, Eudragit® NE30D, and Eudragit® NE 40D, cellulose acetate phthalate, sepifilms such as mixtures of HPMC and stearic acid, cyclodextrins, and mixtures of these materials.

In still other embodiments, plasticizers such as polyethylene glycols, e.g., PEG 300, PEG 400, PEG 600, PEG 1450, PEG 3350, and PEG 800, stearic acid, propylene glycol, oleic acid, and triacetin are incorporated into the microencapsulation material. In other embodiments, the microencapsulating material useful for delaying the release of the pharmaceutical compositions is from the USP or the National Formulary (NF). In yet other embodiments, the microencapsulation material is Klucel. In still other embodiments, the microencapsulation material is methocel.

Microencapsulated compounds capable of modulating intracellular calcium levels described herein are formulated by methods which in some embodiments, include, e.g., spray drying processes, spinning disk-solvent processes, hot melt processes, spray chilling methods, fluidized bed, electrostatic deposition, centrifugal extrusion, rotational suspension separation, polymerization at liquid-gas or solid-gas interface, pressure extrusion, or spraying solvent extraction bath. In addition to these, in some other embodiments, several chemical techniques, e.g., complex coacervation, solvent evaporation, polymer-polymer incompatibility, interfacial polymerization in liquid media, in situ polymerization, in-liquid drying, and desolvation in liquid media are used. Furthermore, in other embodiments, other methods such as roller compaction, extrusion/spheronization, coacervation, or nanoparticle coating also are used.

In still other embodiments, effervescent powders are also prepared in accordance with the present disclosure. Effervescent salts have been used to disperse medicines in water for oral administration. Effervescent salts are granules or coarse powders containing a medicinal agent in a dry mixture, usually composed of sodium bicarbonate, citric acid and/or tartaric acid. When such salts are added to water, the acids and the base react to liberate carbon dioxide gas, thereby causing "effervescence." Examples of effervescent salts include, e.g., the following ingredients: sodium bicarbonate or a mixture of sodium bicarbonate and sodium carbonate, citric acid and/or tartaric acid. Any acid-base combination that results in the liberation of carbon dioxide are used in place of the combination of sodium bicarbonate and citric and tartric acids, as long as the ingredients were suitable for pharmaceutical use and result in a pH of about 6.0 or higher.

In other embodiments, the formulations described herein, which include a compound described herein, are solid dispersions. In still other embodiments, the formulations described herein are solid solutions. Solid solutions incorporate a substance together with the active agent and other excipients such that heating the mixture results in dissolution of the drug and the resulting composition is then cooled to provide a solid blend which is further formulated or directly added to a capsule or compressed into a tablet.

The pharmaceutical solid oral dosage forms including formulations described herein, which include a compound capable of modulating intracellular calcium levels described herein, are further formulated to provide a controlled release such compounds. Controlled release refers to the release of the compounds capable of modulating intracellular calcium levels described herein from a dosage form in which it is incorporated according to a desired profile over an extended period of time. Controlled release profiles include, for example, sustained release, prolonged release, pulsatile release, and delayed release profiles. In contrast to immediate release compositions, controlled release compositions allow delivery of an agent to a subject over an extended period of time according to a predetermined profile. In some embodiments, such release rates provide therapeutically effective levels of agent for an extended period of time and thereby provide a longer period of pharmacologic response while minimizing side effects as compared to conventional rapid release dosage forms. Such longer periods of response provide for many inherent benefits that are not achieved with the corresponding short acting, immediate release preparations.

In some embodiments, the solid dosage forms described herein are formulated as enteric coated delayed release oral dosage forms, i.e., as an oral dosage form of a pharmaceutical composition as described herein which utilizes an enteric coating to affect release in the small intestine of the gastrointestinal tract. In further embodiments, the enteric coated dosage form is a compressed or molded or extruded tablet/mold (coated or uncoated) containing granules, powder, pellets, beads or particles of the active ingredient and/or other composition components, which are themselves coated or uncoated. In other embodiments, the enteric coated oral dosage form is also a capsule (coated or uncoated) containing pellets, beads or granules of the solid carrier or the composition, which are themselves coated or uncoated.

The term "delayed release" as used herein refers to the delivery so that the release is accomplished at some generally predictable location in the intestinal tract more distal to that which would have been accomplished if there had been no delayed release alterations. In some embodiments the method for delay of release is a coating. Any coatings should be applied to a sufficient thickness such that the entire coating does not dissolve in the gastrointestinal fluids at pH below about 5, but does dissolve at pH about 5 and above. In some embodiments, coatings are made from:

Acrylic polymers. In some embodiments, the performance of acrylic polymers (primarily their solubility in biological fluids) vary based on the degree and type of substitution. Examples of suitable acrylic polymers include methacrylic acid copolymers and ammonium methacrylate copolymers. The Eudragit series E, L, S, RL, RS and NE (Rohm Pharma) are available as solubilized in organic solvent, aqueous dispersion, or dry powders. The Eudragit series RL, NE, and RS are insoluble in the gastrointestinal tract but are permeable and are used primarily for colonic targeting. The Eudragit series E dissolve in the stomach. The Eudragit series L, L-30D and S are insoluble in stomach and dissolve in the intestine;

Cellulose Derivatives. Examples of suitable cellulose derivatives are: ethyl cellulose; reaction mixtures of partial acetate esters of cellulose with phthalic anhydride. In other embodiments, the performance varies based on the degree and type of substitution. Cellulose acetate phthalate (CAP) dissolves in pH>about 6. Aquateric (FMC) is an aqueous based system and is a spray dried CAP psuedolatex with particles <1 μm. In other embodiments, other components in Aquateric include pluronics, Tweens, and acetylated monoglycerides. Other suitable cellulose derivatives include: cellulose acetate trimellitate (Eastman); methylcellulose (Pharmacoat, Methocel); hydroxypropylmethyl cellulose phthalate (HPMCP); hydroxypropylmethyl cellulose succinate (HPMCS); and hydroxypropylmethylcellulose acetate succinate (e.g., AQOAT (Shin Etsu)). In further embodiments, the performance varies based on the degree and type of substitution. For example, HPMCP such as, HP-50, HP-55, HP-55S, BP-55F grades are suitable. In other embodiments, the performance varies based on the degree and type of substitution. For example, suitable grades of hydroxypropylmethylcellulose acetate succinate include, but are not limited to, AS-LG (LF), which dissolves at pH about 5, AS-MG (MF), which dissolves at pH about 5.5, and AS-HO(HF), which dissolves at higher pH. These polymers are offered as granules, or as fine powders for aqueous dispersions;

Poly Vinyl Acetate Phthalate (PVAP). PVAP dissolves in pH>about 5, and it is much less permeable to water vapor and gastric fluids.

In some embodiments, the coating contains a plasticizer and possibly other coating excipients such as colorants, talc, and/or magnesium stearate. Suitable plasticizers include triethyl citrate (Citroflex 2), triacetin (glyceryl triacetate), acetyl triethyl citrate (Citroflec A2), Carbowax 400 (polyethylene glycol 400), diethyl phthalate, tributyl citrate, acetylated monoglycerides, glycerol, fatty acid esters, propylene glycol, and dibutyl phthalate. In some embodiments, anionic carboxylic acrylic polymers contain about 10 to about 25% by weight of a plasticizer, especially dibutyl phthalate, polyethylene glycol, triethyl citrate and triacetin. Conventional coating techniques such as spray or pan coating are employed to apply coatings. The coating thickness must be sufficient to ensure that the oral dosage form remains intact until the desired site of topical delivery in the intestinal tract is reached.

In some embodiments, colorants, detackifiers, surfactants, antifoaming agents, lubricants (e.g., carnuba wax or PEG) are added to the coatings besides plasticizers to solubilize or disperse the coating material, and to improve coating performance and the coated product.

In other embodiments, the formulations described herein are delivered using a pulsatile dosage form. A pulsatile dosage form is capable of providing one or more immediate release pulses at predetermined time points after a controlled lag time or at specific sites. In further embodiments, pulsatile dosage forms are administered using a variety of pulsatile formulations.

Examples of such delivery systems include, e.g., polymer-based systems, such as polylactic and polyglycolic acid, polyanhydrides and polycaprolactone; porous matrices, nonpolymer-based systems that are lipids, including sterols, such as cholesterol, cholesterol esters and fatty acids, or neutral fats, such as mono-, di- and triglycerides; hydrogel release systems; silastic systems; peptide-based systems; wax coatings, bioerodible dosage forms, compressed tablets using conventional binders and the like.

In some embodiments, pharmaceutical formulations are provided that include particles of the compounds described herein and at least one dispersing agent or suspending agent for oral administration to a subject. In some embodiments, the formulations are a powder and/or granules for suspension, and upon admixture with water, a substantially uniform suspension is obtained.

In some embodiments, liquid formulation dosage forms for oral administration are aqueous suspensions selected from the group including, but not limited to, pharmaceutically acceptable aqueous oral dispersions, emulsions, solutions, elixirs, gels, and syrups.

In other embodiments, the aqueous suspensions and dispersions described herein remain in a homogenous state, as defined in The USP Pharmacists' Pharmacopeia (2005 edition, chapter 905), for at least 4 hours. The homogeneity should be determined by a sampling method consistent with regard to determining homogeneity of the entire composition. In one embodiment, an aqueous suspension is re-suspended into a homogenous suspension by physical agitation lasting less than about 1 minute. In another embodiment, an aqueous suspension is re-suspended into a homogenous suspension by physical agitation lasting less than about 45 seconds. In yet another embodiment, an aqueous suspension is re-suspended into a homogenous suspension by physical agitation lasting less than about 30 seconds. In still another embodiment, no agitation is necessary to maintain a homogeneous aqueous dispersion.

In some embodiments, the pharmaceutical formulations described herein are self-emulsifying drug delivery systems (SEDDS). Emulsions are dispersions of one immiscible phase in another, usually in the form of droplets. Generally, emulsions are created by vigorous mechanical dispersion. SEDDS, as opposed to emulsions or microemulsions, spontaneously form emulsions when added to an excess of water without any external mechanical dispersion or agitation. An advantage of SEDDS is that only gentle mixing is required to distribute the droplets throughout the solution. Additionally, in other embodiments, water or the aqueous phase is added just prior to administration, which ensures stability of an unstable or hydrophobic active ingredient. Thus, the SEDDS provides an effective delivery system for oral and parenteral delivery of hydrophobic active ingredients. In further embodiments, SEDDS provides improvements in the bioavailability of hydrophobic active ingredients.

It is to be appreciated that there is overlap between the above-listed additives used in the aqueous dispersions or suspensions described herein, since a given additive is often classified differently by different practitioners in the field, or is commonly used for any of several different functions. Thus, in other embodiments, the above-listed additives are taken as merely exemplary, and not limiting, of the types of additives that are included in formulations described herein.

In some embodiments, formulations that include a compound described herein, are prepared according to these and other techniques are prepared as solutions in saline, employing benzyl alcohol or other suitable preservatives, fluorocarbons, and/or other solubilizing or dispersing agents. In other embodiments, are compositions and formulations prepared with suitable nontoxic pharmaceutically acceptable ingredients. In further embodiments, these ingredients are found in REMINGTON: THE SCIENCE AND PRACTICE OF PHARMACY, 21st edition, 2005. The choice of suitable carriers is highly dependent upon the exact nature of the nasal dosage form desired, e.g., solutions, suspensions, ointments, or gels. Nasal dosage forms generally contain large amounts of water in addition to the active ingredient. Minor amounts of other ingredients such as pH adjusters, emulsifiers or dispersing agents, preservatives, surfactants, gelling agents, or buffering and other stabilizing and solubilizing agents are optionally present. In other embodiments, the nasal dosage form is isotonic with nasal secretions.

In some embodiments, for administration by inhalation, the compounds described herein are in a form as an aerosol, a mist or a powder. Pharmaceutical compositions described herein are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In further embodiments, are pressurized aerosols, wherein the dosage unit is determined by providing a valve to deliver a metered amount. Capsules and cartridges of, such as, by way of example only, gelatin for use in an inhaler or insufflator are formulated containing a powder mix of the compound described herein and a suitable powder base such as lactose or starch.

In other embodiments, are buccal formulations that include compounds described herein are administered using a variety of formulations. In some embodiments, the buccal dosage forms described herein further include a bioerodible hydrolysable) polymeric carrier that also serves to adhere the dosage form to the buccal mucosa. The buccal dosage form is fabricated so as to erode gradually over a predetermined time period, wherein the delivery of the compound is provided essentially throughout. Buccal drug delivery, avoids the disadvantages encountered with oral drug administration, e.g., slow absorption, degradation of the active agent by fluids present in the gastrointestinal tract and/or first-pass inactivation in the liver. With regard to the bioerodible (hydrolysable) polymeric carrier, it will be appreciated that virtually any such carrier is used, so long as the desired drug release profile is not compromised, and the carrier is compatible with the compounds capable of modulating intracellular calcium levels described herein, and any other components that are present in the buccal dosage unit. Generally, the polymeric carrier comprises hydrophilic (water-soluble and water-swellable) polymers that adhere to the wet surface of the buccal mucosa. Examples of polymeric carriers useful herein include acrylic acid polymers and co, e.g., "carbomers" (Carbopol®, which are obtained from B.F. Goodrich, is one such polymer). In further embodiments are components incorporated into the buccal dosage forms described herein include, but are not limited to, disintegrants, diluents, binders, lubricants, flavoring, colorants, preservatives, and the like. In yet further embodiments, are buccal or sublingual administration, wherein the compositions take the form of tablets, lozenges, or gels formulated in a conventional manner.

In further embodiments, are transdermal formulations described herein administered using a variety of devices.

In other embodiments the transdermal dosage forms described herein incorporate certain pharmaceutically acceptable excipients. In one embodiment, the transdermal formulations described herein include at least three components: (1) a formulation of a compound capable of modulating intracellular calcium levels; (2) a penetration enhancer; and (3) an aqueous adjuvant. In addition, transdermal formulations include additional components such as, but not limited to, gelling agents, creams and ointment bases, and the like. In some embodiments, the transdermal formulation further includes a woven or non-woven backing material to enhance absorption and prevent the removal of the transdermal formulation from the skin. In other embodiments, the transdermal formulations described herein maintains a saturated or supersaturated state to promote diffusion into the skin.

In other embodiments, formulations suitable for transdermal administration of compounds described herein employ transdermal delivery devices and transdermal delivery patches and are lipophilic emulsions or buffered, aqueous solutions, dissolved and/or dispersed in a polymer or an adhesive. Such patches are constructed for continuous, pulsatile, or on demand delivery of pharmaceutical agents. Still further, in some embodiments, transdermal delivery of the compounds described herein are accomplished by means of iontophoretic patches and the like. Additionally, in other embodiments, transdermal patches provide controlled delivery of the compound capable of modulating intracellular calcium levels described herein. In further embodiments, the rate of absorption is slowed by using rate-controlling membranes or by trapping the compound within a polymer matrix or gel. Conversely, in yet further embodiments, absorption enhancers are used to increase absorption. An absorption enhancer or carrier includes absorbable pharmaceutically acceptable solvents to assist passage through the skin. For example, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin.

In further embodiments, formulations suitable for intramuscular, subcutaneous, or intravenous injection include physiologically acceptable sterile aqueous or non-aqueous solutions, dispersions, suspensions or emulsions, and sterile powders for reconstitution into sterile injectable solutions or dispersions. Examples of suitable aqueous and non-aqueous carriers, diluents, solvents, or vehicles including water, ethanol, polyols (propyleneglycol, polyethylene-glycol, glycerol, cremophor and the like), suitable mixtures thereof, vegetable oils (such as olive oil) and injectable organic esters such as ethyl oleate. In some embodiments, proper fluidity is maintained, for example, by the use of a coating such as lecithin, by the maintenance of the required particle size in the case of dispersions, and by the use of surfactants. In further embodiments, formulations suitable for subcutaneous injection also contain additives such as preserving, wetting, emulsifying, and dispensing agents. Prevention of the growth of microorganisms is ensured by various antibacterial and antifungal agents, such as parabens, chlorobutanol, phenol, sorbic acid, and the like. An additional embodiment includes isotonic agents, such as sugars, sodium chloride, and the like. Prolonged absorption of the injectable pharmaceutical form are brought about by the use of agents delaying absorption, such as aluminum monostearate and gelatin.

In some embodiments, are intravenous injections, compounds formulated in aqueous solutions; in some embodiments, in physiologically compatible buffers such as Hank's solution, Ringer's solution, or physiological saline buffer. For transmucosal administration, penetrants appropriate to the barrier to be permeated are used in the formulation For other parenteral injections, appropriate formulations optionally includes aqueous or nonaqueous solutions; in other embodiments, with physiologically compatible buffers or excipients.

In some embodiments, parenteral injections involve bolus injection or continuous infusion. In other embodiments, formulations for injection are presented in unit dosage form, e.g., in ampoules or in multi-dose containers, with an added preservative. In some embodiments, the pharmaceutical compositions described herein are in a form suitable for parenteral injection as a sterile suspensions, solutions or emulsions in oily or aqueous vehicles, and contain formulatory agents such as suspending, stabilizing and/or dispersing agents. Pharmaceutical formulations for parenteral administration include aqueous solutions of the active compounds in water-soluble form. Additionally, in other embodiments, suspensions of the active compounds are prepared as appropriate oily injection suspensions. Suitable lipophilic solvents or vehicles include fatty oils such as sesame oil, or synthetic fatty acid esters, such as ethyl oleate or triglycerides, or liposomes. In further embodiments, aqueous injection suspensions contain substances which increase the viscosity of the suspension, such as sodium carboxymethyl cellulose, sorbitol, or dextran. In some embodiments, the suspension also contains suitable stabilizers or agents which increase the solubility of the compounds to allow for the preparation of highly concentrated solutions. In other embodiments, the active ingredient is in powder form for constitution with a suitable vehicle, e.g., sterile pyrogen-free water, before use.

In certain embodiments, delivery systems for pharmaceutical compounds are employed, such as, for example, liposomes and emulsions. In certain embodiments, compositions provided herein optionally also include an mucoadhesive polymer, selected from among, for example, carboxymethylcellulose, carbomer (acrylic acid polymer), poly(methylmethacrylate), polyacrylamide, polycarbophil, acrylic acid/butyl acrylate copolymer, sodium alginate and dextran.

In some embodiments, the compounds described herein are administered topically and are formulated into a variety of topically administrable compositions, such as solutions, suspensions, lotions, gels, pastes, medicated sticks, balms, creams or ointments. Such pharmaceutical compounds contain for example, solubilizers, stabilizers, tonicity enhancing agents, buffers and preservatives.

In some embodiments, the compounds described herein are also formulated in rectal compositions such as enemas, rectal gels, rectal foams, rectal aerosols, suppositories, jelly suppositories, or retention enemas, containing conventional suppository bases such as cocoa butter or other glycerides, as well as synthetic polymers such as polyvinylpyrrolidone, PEG, and the like. In suppository forms of the compositions, a low-melting wax such as, but not limited to, a mixture of fatty acid glycerides, optionally in combination with cocoa butter is first melted.

Generally, an agent, such as a compound capable of modulating intracellular calcium levels, is administered in an amount effective for amelioration of, or prevention of the development of symptoms of, the disease, condition or disorder (i.e., a therapeutically effective amount). Thus, in some embodiments, a therapeutically effective amount is an amount that is capable of at least partially preventing or reversing a disease, condition or disorder. In other embodiments, the dose required to obtain an effective amount varies depending on the agent, formulation, disease, condition or disorder, and individual to whom the agent is administered.

In other embodiments, determination of effective amounts also involves in vitro assays in which varying doses of agent are administered to cells in culture and the concentration of agent effective for ameliorating some or all symptoms is determined in order to calculate the concentration required in vivo. Effective amounts are also based on in vivo animal studies.

In other embodiments, an agent is administered prior to, concurrently with and subsequent to the appearance of symptoms of a disease, condition or disorder. In some embodiments, an agent is administered to a subject with a family history of the disease, condition or disorder, or who has a phenotype that indicates a predisposition to a disease, condition or disorder, or who has a genotype which predisposes the subject to the disease, condition or disorder.

In some embodiments, the particular delivery system used depends on a number of factors, including, for example, the intended target and the route of administration, e.g., local or systemic. Targets for delivery are specific cells which are causing or contributing to a disease, condition or disorder, including, for example, cells that have altered intracellular calcium or calcium dysregulation or dyshomeostasis, and cells that do not have altered intracellular calcium but that in some embodiments, have some alteration, defect or deficiency that is, at least in part, compensated, counteracted, reversed or alleviated or eliminated by altering intracellular calcium of the cell. Particular cells include, for example, immune cells (e.g., lymphocytes, T cells, B cells, white blood cells), fibroblasts (or cells derived from a fibroblast), epidermal, dermal or skin cells (e.g., a keratinocytes), blood cells, kidney or renal cells (e.g., mesangial cells), muscle cells (e.g., a smooth muscle cell such as an airway (tracheal or bronchial) smooth muscle cell) and exocrine or secretory (e.g., salivary, including parotid acinar and submandibular gland) cells. For example, in some embodiments, a target cell is a resident or infiltrating cells in the lungs or airways that contribute to an asthmatic illness or disease, resident or infiltrating cells in the nervous system contributing to a neurological, neurodegenerative or demyelinating disease, condition or disorder, resident or infiltrating cells involved in rejection of a kidney graft, grafted cells that when activated lead to graft-versus-host disease, resident or infiltrating cells involved in rejection of a kidney graft, resident or infiltrating cells, activation of which contributes to inflammation, e.g., in arthritis, resident or infiltrating cells in the kidney or renal system (e.g., mesangial cells) involved in neuropathy and glomerulonephritis and resident or infiltrating cells in exocrine glands (e.g., salivary and lacrimal glands) involved in autoimmune disorders (e.g., Sjogren's disease). In some embodiments, an agent is coupled to an antibody, ligand to a cell surface receptor or a toxin, or is contained in a particle that is selectively internalized into cells, e.g., liposomes or a virus in which the viral receptor binds specifically to a certain cell type, or a viral particle lacking the viral nucleic acid, or are administered locally.

Examples of Methods of Dosing and Treatment Regimens

In some embodiments, the compounds described herein are used in the preparation of medicaments for the modulation of a STIM protein and/or an Orai protein, or for the treatment of diseases, disorders or conditions that would benefit, at least in part, from modulation of a STIM protein and/or an Orai protein. In addition, a method for treating any of the diseases, disorders or conditions described herein in a subject in need of such treatment, involves administration of pharmaceutical compositions containing at least one compound described herein, or a pharmaceutically acceptable salt, pharmaceutically acceptable prodrug, or pharmaceutically acceptable solvate thereof, in therapeutically effective amounts to said subject.

In other embodiments, the compositions containing the compound(s) described herein are administered for prophylactic and/or therapeutic treatments. In therapeutic applications, the compositions are administered to a patient already suffering from a disease, disorder or condition, in an amount sufficient to cure or at least partially arrest the symptoms of the disease, disorder or condition. Amounts effective for this use will depend on the severity and course of the disease, disorder or condition, previous therapy, the patient's health status, weight, and response to the drugs, and the judgment of the treating physician.

In prophylactic applications, compositions containing the compounds described herein are administered to a patient susceptible to or otherwise at risk of a particular disease, disorder or condition. Such an amount is defined to be a "prophylactically effective amount or dose." In this use, the precise amounts also depend on the patient's state of health, weight, and the like. When used in a patient, effective amounts for this use will depend on the severity and course of the disease, disorder or condition, previous therapy, the patient's health status and response to the drugs, and the judgment of the treating physician.

In some embodiments wherein the patient's condition does not improve, upon the doctor's discretion the administration of the compounds is administered chronically, that is, for an extended period of time, including throughout the duration of the patient's life in order to ameliorate or otherwise control or limit the symptoms of the patient's disease or condition.

In other embodiments, wherein the patient's status does improve, upon the doctor's discretion the administration of the compounds are given continuously; alternatively, the dose of drug being administered is temporarily reduced or temporarily suspended for a certain length of time (i.e., a "drug holiday"). In other embodiments, the length of the drug holiday varies between about 2 days and about 1 year, including by way of example only, about 2 days, about 3 days, about 4 days, about 5 days, about 6 days, about 7 days, about 10 days, about 12 days, about 15 days, about 20 days, about 28 days, about 35 days, about 50 days, about 70 days, about 100 days, about 120 days, about 150 days, about 180 days, about 200 days, about 250 days, about 280 days, about 300 days, about 320 days, about 350 days, or about 365 days. In some embodiments, the dose reduction during a drug holiday is from about 10% to about 100%, including, by way of example only, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%.

Once improvement of the patients conditions has occurred, a maintenance dose is administered if necessary. Subsequently, in other embodiments, the dosage or the frequency of administration, or both, is reduced, as a function of the symptoms, to a level at which the improved disease, disorder or condition is retained. In other embodiments, patients, however, require intermittent treatment on a long-term basis upon any recurrence of symptoms.

In other embodiments, the amount of a given agent varies depending upon factors such as the particular compound, disease, disorder or condition and its severity, the identity (e.g., weight) of the subject or host in need of treatment, but is nevertheless determined in a manner according to the particular circumstances surrounding the case, including, e.g., the specific agent being administered, the route of administration, the condition being treated, and the subject or host being treated. In some embodiments, doses employed for adult human treatment are typically in the range of about 0.02 to about 5000 mg per day, in other embodiments, about 1 to about 1500 mg per day. In further embodiments, the desired dose is conveniently presented in a single dose or as divided doses administered simultaneously (or over a short period of time) or at appropriate intervals, for example as two, three, four or more sub-doses per day.

In other embodiments, the pharmaceutical composition described herein is in unit dosage forms suitable for single administration of precise dosages. In unit dosage form, the formulation is divided into unit doses containing appropriate quantities of one or more compound. In firter embodiments, the unit dosage is in the form of a package containing discrete quantities of the formulation. Non-limiting examples are packaged tablets or capsules, and powders in vials or ampoules. In other embodiments, aqueous suspension compositions are packaged in single-dose non-reclosable containers. In farther embodiments, multiple-dose reclosable containers are used, in which case it is typical to include a preservative in the composition. By way of example only, formulations for parenteral injection are presented in unit dosage form, which include, but are not limited to ampoules, or in multi-dose containers, with an added preservative.

The daily dosages appropriate for the compounds described herein described herein are from about 0.01 mg/kg to about 20 mg/kg. In one embodiment, the daily dosages are from about 0.1 mg/kg to about 10 mg/kg. An indicated daily dosage in the larger mammal, including, but not limited to, humans, is in the range from about 0.5 mg to about 1000 mg, conveniently administered in a single dose or in divided doses, including, but not limited to, up to four times a day or in extended release form. Suitable unit dosage forms for oral administration include from about 1 to about 500 mg active ingredient. In one embodiment, the unit dosage is about 1 mg, about 5 mg, about, 10 mg, about 20 mg, about 50 mg, about 100 mg, about 200 mg, about 250 mg, about 400 mg, or about 500 mg. The foregoing ranges are exemplary, as the number of variables in regard to an individual treatment regime is large, and considerable excursions from these recommended values are not uncommon. In some embodiments, such dosages are altered depending on a number of variables, not limited to the activity of the compound used, the disease, disorder or condition to be treated, the mode of administration, the requirements of the individual subject, the severity of the disease, disorder or condition being treated, and the judgment of the practitioner.

In further embodiments, toxicity and therapeutic efficacy of such therapeutic regimens are determined by standard pharmaceutical procedures in cell cultures or experimental animals, including, but not limited to, the determination of the $LD_{50}$ (the dose lethal to 50% of the population) and the $ED_{50}$ (the dose therapeutically effective in 50% of the population). The dose ratio between the toxic and therapeutic effects is the therapeutic index and it are expressed as the ratio between $LD_{50}$ and $ED_{50}$. In other embodiments, are compounds exhibiting high therapeutic indices. In other embodiments, the data obtained from cell culture assays and animal studies are used in formulating a range of dosage for use in human. In some other embodiments, the dosage of such compounds lies within a range of circulating concentrations that include the $ED_{50}$ with minimal toxicity. In further embodiments, the dosage varies within this range depending upon the dosage form employed and the route of administration utilized.

Kits/Articles of Manufacture

For use in the therapeutic applications described herein, kits and articles of manufacture are also described herein. In some embodiments, such kits include a carrier, package, or container that is compartmentalized to receive one or more containers such as vials, tubes, and the like, each of the container(s) including one of the separate elements to be used in a method described herein. Suitable containers include, for example, bottles, vials, syringes, and test tubes. In other embodiments, the containers are formed from a variety of materials such as glass or plastic.

The articles of manufacture provided herein contain packaging materials. Examples of pharmaceutical packaging materials include, but are not limited to, blister packs, bottles, tubes, inhalers, pumps, bags, vials, containers, syringes, bottles, and any packaging material suitable for a selected formulation and intended mode of administration and treatment. A wide array of formulations of the compounds and compositions provided herein are contemplated as are a variety of treatments for any disease, disorder, or condition that would benefit by inhibition of CRAC channel activity.

For example, in some embodiments, the container(s) includes one or more compounds described herein, optionally in a composition or in combination with another agent as disclosed herein. The container(s) optionally have a sterile access port (for example the container is an intravenous solution bag or a vial having a stopper pierceable by a hypodermic injection needle). Such kits optionally comprising a compound with an identifying description or label or instructions relating to its use in the methods described herein.

In some other embodiments, a kit includes one or more additional containers, each with one or more of various materials (such as reagents, optionally in concentrated form, and/ or devices) desirable from a commercial and user standpoint for use of a compound described herein. Non-limiting examples of such materials include, but not limited to, buffers, diluents, filters, needles, syringes; carrier, package, container, vial and/or tube labels listing contents and/or instructions for use, and package inserts with instructions for use. In other embodiments, a set of instructions is also included.

In further embodiments, is a label on or associated with the container. In other embodiments, the label is on a container when letters, numbers or other characters forming the label are attached, molded or etched into the container itself; a label is associated with a container when it is present within a receptacle or carrier that also holds the container, e.g., as a package insert. In some embodiments, a label is used to indicate that the contents are to be used for a specific therapeutic application. In yet other embodiments, the label also indicates directions for use of the contents, such as in the methods described herein.

In certain embodiments, the pharmaceutical compositions are presented in a pack or dispenser device which contains one or more unit dosage forms containing a compound provided herein. In other embodiments, the pack contains metal or plastic foil, such as a blister pack. In other embodiments, the pack or dispenser device is accompanied by instructions for administration. In still other embodiments, the pack or dispenser also accompanied with a notice associated with the container in form prescribed by a governmental agency regulating the manufacture, use, or sale of pharmaceuticals, which notice is reflective of approval by the agency of the form of the drug for human or veterinary administration. Such notice, for example, is the labeling approved by the U.S. Food and Drug Administration for prescription drugs, or the approved product insert. Compositions containing a compound provided herein formulated in a compatible pharmaceutical carrier are also prepared, placed in an appropriate container, and labeled for treatment of an indicated condition.

Assays

In some embodiments, several techniques are used to evaluate store operated calcium entry and calcium signaling in cells. Such techniques include, but are not limited to, patch clamp electrophysiology (measurement of calcium ions or other ions across cell membranes, such as plasma membranes), capacitance measurements (allows exocytosis to be followed at the level of single cells), calcium imaging using fluorescent dyes allows patterns of calcium movement within the cytoplasm to be tracked, fluorescence resonance energy transfer (FRET) enables protein-protein interactions to be evaluated, and molecular biology methods allow for the manipulation of the levels of expression of proteins of interest.

In other embodiments, a wide variety of assay methods are used to examine the modulation of a STIM protein and/or an Orai protein by compounds capable of modulating intracellular calcium levels. Such assays include in vitro cell based assays as well as in vivo animal models. In some embodiments, are assays that detect, monitor or measure an effect on intracellular calcium, including calcium entry-mediated events. Such assays include, but are not limited to, assays monitoring, measuring and/or detecting intracellular calcium levels, modulation of calcium levels, and movement of calcium into, out of or within cells and intracellular organelles. In other embodiments are assays which also include monitoring, measuring and/or detecting calcium entry-mediated events and molecules involved in calcium entry-mediated events such as, but not limited to, signal transduction molecules, transcription factors, secreted molecules and other molecules that are affected by changes in calcium homeostasis. Assays include, but are not limited to, those described herein and those described in US patent publication no. 2007/ 0031814 and WO 07/081,804, herein incorporated by reference.

Cells and Cell Models

For in vitro testing of the modulation of a STIM protein and/or an Orai protein by compounds capable of modulating intracellular calcium levels, a wide variety of cell types for such assays are available. In one embodiment, the cell is one in which store-operated calcium entry occurs or that is manipulated such that store-operated calcium entry occurs in the cell. In other embodiments, the cell contains one or more proteins involved in modulating intracellular calcium (and, in particular, is involved in, participates in and/or provides for store-operated calcium entry, movement of calcium into, out of or within an intracellular organelle or calcium store, modulation of calcium levels in an intracellular organelle or calcium store (e.g., endoplasmic reticulum) and/or calcium buffering), such as those provided herein. In further embodiments, the protein(s) include a STIM proteins (including STIM1, STIM2, DSTIM and CSTIM protein) and/or Orai proteins (Orai1, Orai2, Orai3). The cell optionally endogenously expresses the protein(s) or recombinantly express the protein(s).

In some embodiments, cells for use in the methods are of any species. In one embodiment, the cells are eukaryotic cells. In one embodiment, the cells are yeast, insect (e.g., *Drosophila* or *Anopheles*), or mammalian cells. Mammalian cells include, but are not limited to, rodent (e.g., mouse, rat and hamster), primate, monkey, dog, bovine, rabbit and human cells. A variety of cell types are used in the methods, including, for example, neuronal, nervous system, brain, immune system cells, e.g., T lymphocytes and B cells, primary cells, blood and hematopoietic cells, stromal cells, myeloid cells, lymphoid cells, and a variety of tumor and cancer cells. Particular cells include *Drosophila* Schneider 2 or S2 cells, human embryonic kidney (HEK293) cells, rat basophilic leukemia (RBL-2H3) cells, Jurkat cells, epithelial cells, rhabdomyosarcoma cells, rhabdoid cells, retinoblastoma cells, neuroepithelioma cells, neuroblastoma cells, osteosarcoma cells, fibroblasts, bone marrow stroma cells, erythroleukemia cells and lymphoblast cells. Other cell lines include HEK 293 and 293T, CHO (including CHO-K1), LTK-, N2A, H6, and HGB. Many such cells and cell lines are available through cell depositories such as, for example, the American Type Culture Collection (ATCC, Manassas, Va.). In further embodiments, primary cells are obtained by isolation from tissue sources.

In other embodiments, cells from an established cell line are used, such as neuroblastoma SH-SY5Y cells, pheochromocytoma PC12 cells, neuroblastoma SK-N-BE(2)C or SK-N-SH cells, human SK-N-MC neuroepithelioma cells, SMS-KCNR cells, human LAN-5 neuroblastoma cells, human GI-CA-N neuroblastoma cells, human GOTO neuroblastoma cells, mouse Neuro 2a (N2A) neuroblastoma cells and/or human IMR 32 neuroblastoma cells, chronic myeloid leukemia cells (e.g., human K562 cells), promyelocytic leukemia cells (e.g., HL60 cells) and histiocytic lymphoma cells (e.g., U937 cells), Burkitt's lymphoma cells (e.g., CA46 cells), B-cells (e.g., NALM6), acute lymphoblastic leukemia cells (e.g., MOLT4 cells), T cells (e.g. Jurkat cells) and early T-ALL (e.g., DU528) cells.

The choice of a cell for use in an in vitro assay to test the modulation of intracellular calcium by compounds capable of modulating intracellular calcium levels involve several considerations, including, for example, a particular protein that is being used in the method and a particular aspect or activity of intracellular calcium modulation that is being monitored or assessed in the method.

In one embodiment, the modulation of intracellular calcium by compounds capable of modulating intracellular calcium levels is examined by monitoring or assessing the effect on store-operated calcium entry. Cells typically used in such methods exhibit store-operated calcium entry either naturally or through manipulation of the cells. In other embodiments, cells that endogenously exhibit store-operated calcium entry include some excitable cells and most non-excitable cells and are identified using methods described herein.

In one embodiment, it is desirable to utilize a cell that contains components of signaling and messenger systems that effects release of calcium from intracellular stores. For example, cells containing components of receptor-mediated phospholipase C(PLC) activation systems are used for physiological activation (via generation of $IP_3$) of store depletion to facilitate monitoring of store-operated calcium entry. Receptor-mediated PLC activation occurs through distinct coupling mechanisms: PLC-β activation by G protein-coupled receptors (GPCRs) and PLC-γ activation by tyrosine kinase receptors and nonreceptor tyrosine kinases. Thus, cells containing a receptor-mediated PLC-activation system are monitored or assessed for store-operated calcium entry upon agonist activation of one or more receptors that participates in the system.

In another embodiment, an assessment of intracellular calcium after treatment with compounds capable of modulating intracellular calcium levels is made under a variety of conditions. Conditions are selected to evaluate the effect of test agent on a specific aspect of intracellular calcium. For example, in some embodiments reagents and conditions are used for specifically evaluating store-operated calcium entry, resting cytosolic calcium levels, calcium buffering, and calcium levels of and calcium uptake by or release from intracellular organelles, in further embodiments, resting cytosolic calcium levels, intracellular organelle calcium levels and cation movement are assessed using any of the methods described herein. Such methods of assessing modulation in intracellular calcium include, but are not limited to, calcium-sensitive indicator-based measurements, such as fluo-3, mag-fura 2 and ER-targeted aequorin, labeled calcium (such as $^{45}Ca^{2+}$)-based measurements, and electrophysiological measurements. Particular aspects of ion flux that are assessed include, but are not limited to, a reduction (including elimination) in the amount of ion flux, altered biophysical properties of the ion current, and altered sensitivities of the flux to activators or inhibitors of calcium flux processes, such as, for example, store-operated calcium entry. Reagents and conditions for use in specifically evaluating receptor-mediated calcium movement and second messenger-operated calcium movement are also available.

Evaluation of STIM/Orai Interaction Upon Treatment with Test Compounds or Agents In one aspect, compounds are added to cells to determine if they are capable of modulating STIM/Orai interaction at the plasma membrane. For example, in one embodiment, cells are transfected with a STIM nucleic acid and an Orai nucleic acid that are expressed, or alternatively, over-expressed in the test cell. In some embodiments, the STIM nucleic acid is labeled with a tag molecule upon expression in the cell. In other embodiments, the Orai nucleic acid is labeled with a tag molecule upon expression in the cell. In yet other embodiments, the STIM and Oral expressed proteins in the cell are unlabeled. In some embodiments, STIM and Orai protein expression levels are monitored in the cell after transfection, for example, using Western blot analysis, ELISA quantitative and/or qualitative assays, 2-D gel analysis or protein/reporter gene conjugates (e.g. green fluorescent protein (GFP) quantitation), or a combination thereof.

In another embodiment, cells are transfected with a STIM nucleic acid and an Orai nucleic acid that, upon expression, are both, or singly, labeled with a tag molecule. The tag molecule is an enzyme fragment (see, e.g. US Patent Application No. 2007/0105160, incorporated by reference herein in its entirety), a protein (e.g. c-myc or other tag protein or fragment thereof), an enzyme tag, a fluorescent tag, a fluorophore tag, a chromophore tag, a Raman-activated tag, a chemiluminescent tag, a quantum dot marker, an antibody, a radioactive tag, or combinations thereof. In another embodiment, a STIM polypeptide and an Orai polypeptide labeled tag molecule are introduced into cells for incorporation into the plasma and endoplasmic reticulum membrane. In still other embodiments, the cells are recombinant cells with stably incorporate tagged STIM and Orai nucleic acids. In some aspects, the tag marker activity level is changed when a STIM polypeptide migrates and comes within close proximity of the Orai polypeptide, for example, with FRET energy transfer.

In some aspects, enzyme activity is monitored before and after treatment to determine if enzyme activity is modulated by treatment with test compounds or agents. In other aspects, fluorescent activity is monitored before and treatment to determine if marker levels, for example, FRET-induced fluorescent levels, are modulated by treatment with test compounds or agents. In all aspects, the marker activity is monitored to determine if the test agent of compound is capable of modulating the marker activity level with treatment.

Evaluation of Store-Operated Calcium Entry

In another aspect, compounds capable of modulating intracellular calcium levels are added to cells under conditions that permit store-operated calcium entry to occur in order to assess the effects of compounds capable of modulating intracellular calcium levels on store-operated calcium entry.

For example, in one method cells are treated to reduce the calcium levels of intracellular calcium stores and then analyzed for evidence of ion (e.g., calcium) influx in response thereto in the presence of a compound capable of modulating intracellular calcium levels. Techniques for reducing calcium levels of intracellular stores and for analyzing cells for evidence of ion (e.g., calcium) influx are described herein.

In other methods, electrophysiological analysis of currents across a cell-detached plasma membrane patch or an outside-out membrane vesicle are used to detect or monitor store-operated channel currents (e.g., $I_{SOC}$, $I_{CRAC}$) in the presence of a compound capable of modulating intracellular calcium levels.

Evaluation of Calcium Entry-Mediated Events

A number of molecules involved in calcium-regulated pathways have been identified. Evaluation of molecules involved in calcium-entry mediated events are used to monitor intracellular calcium, by way of example only, in screening assays described herein to monitor the effects of compounds capable of modulating intracellular calcium levels. Examples of assays include but are not limited to assays which detect, or determine the presence, levels, alteration of levels, production, modification (such as phosphorylation and dephosphorylation), translocation, degradation and activity of molecules involved in calcium-entry mediated events (see for example, Trevillyan et al. (2001) J. Biol. Chem. 276:48118-26). In some embodiments, the assays described herein are used with cells that have been treated with or contacted with compounds capable of modulating intracellular calcium levels, or that express an altered amount of a test molecule (such as a protein involved in calcium regulation, including a STIM protein, Orai protein), or with control cells. In other embodiments, the assays are also conducted in cells that have been stimulated with a physiological or non-physiological activator, or in unstimulated cells. The following are representative assays for molecules involved in calcium-entry mediated events and are meant to be exemplary only. Other assays for these molecules and assays for other molecules involved in calcium-entry mediated events are also employed in any of the screening and/or modulation methods described herein.

β-Hexosaminidase Release

In mast cells, $Ca^{2+}$ influx results in degranulation and release of inflammatory mediators such as heparin, histamine and enzymes such as β-hexosaminidase. In further embodiments, detecting and/or measuring release of such molecules is used to monitor intracellular calcium. For example, in other embodiments, media from mast cells are collected. In further embodiments, suitable substrate for β-hexosaminidase (e.g. p-nitrophenyl-acetyl-glucosamide) is then added and the absorbance of the resulting mixture assessed to measure the relative amount of β-hexosaminidase activity in the samples.

Calcium/Calmodulin-Dependent CaN Phosphatase Activity

The phosphatase calcineurin (CaN) dephosphorylates various proteins, affecting their activity and localization. In other embodiments, CaN activity is assessed by incubating purified CaN and a CaN substrate, for example a radiolabeled peptide corresponding to a sequence in the RII subunit of cAMP-dependent kinase, either with or without compounds capable of modulating intracellular calcium levels (see, Trevillyan et al. (2001) J. Biol. Chem. 276:48118-26). In further embodiments, the level of radiolabeled peptide and/or the amount of free inorganic phosphate released is measured to assess CaN dephosphorylation activity.

NFAT Transcriptional Activity

The NFAT (nuclear factor of activated T cells) transcription factor regulates a number of genes in response to intracellular calcium levels. For example, NEAT proteins regulate the transcription of cytokine genes involved in the immune response. In other embodiments, promoters from NFAT-regulated genes, and/or regulatory regions and elements from these genes, are used to monitor NFAT regulated expression and thereby monitor intracellular calcium. In further embodiments, reporter gene fusions are constructed with NFAT regulated promoters or NFAT-regulated elements operably linked to a reporter gene such as luciferase, β-galactosidase, green fluorescent protein (GFP) or any other established reporter system (see for example, Published U.S. Application no. 2002-0034728). The amount of reporter protein or activity is a measure of NFAT activity.

NFAT Phosphorylation

NFAT activation is regulated primarily through its phosphorylation, which in turn regulates its subcellular localization. In unstimulated cells, NFAT is a hyperphosphorylated cytosolic protein. An elevation in intracellular $Ca^{2+}$, induced by a variety of mechanisms, increases the activity of the $Ca^{2+}$-calmodulin-dependent phosphatase, calcineurin. Activated calcineurin dephosphorylates multiple serine residues within the regulatory region of the NFAT molecule. NFAT is rephosphorylated in response to decreases in $Ca^{2+}$ levels or CaN inhibition.

The phosphorylation state of NFAT is monitored for example, by expressing, a detectably tagged NFAT protein in cells, such as a His6 tagged-NFAT (His6 disclosed as SEQ ID NO: 1). Tagged NFAT is purified from cells using $Ni^{2+}$ chromatography and subjected to gel electrophoresis and staining or western blotting. More highly phosphorylated forms of NFAT are distinguished by their slower migration. In further embodiments, the state of phosphorylated NFAT is used as a measure of NFAT activation (see, Trevillyan et al. (2001) J. Biol. Chem 276:48118-26).

NFAT Nuclear Localization

NEAT localization between the cytoplasm and nucleus is regulated by the phosphorylation state of NFAT. Phosphorylation of NFAT prevents nuclear localization by masking the nuclear localization sequence. NFAT nuclear localization are monitored, for example, by expressing fluorescently tagged NFAT, for example, GFP-NFAT, in cells. In further embodiments, confocal microscopy is used to monitor nuclear localization of the tagged NFAT (see, Trevillyan et al. (2001) J. Bol. Chem. 276:48118-26).

Cytokine Secretion

In some embodiments, cytokine secretion, such as IL-2 secretion, is monitored using protein detection assays. For example, supernatant is collected from immune cells. In other embodiments, an ELISA assay or other suitable format with IL-2 antibodies is used to detect and/or measure the amount of IL-2 secreted as compared to control cells. Secretion of other cytokines, for example, TNF-α, is also detected in similar assays.

Cytokine Expression

Expression of cytokines, such as, but not limited to IL-2, are assessed either directly or indirectly in cells. For example, in indirect methods, an IL-2 promoter are operably linked to a reporter gene such as luciferase or β-galactosidase, and the reporter construct introduced into cells. In further embodiments, reporter gene expression is monitored and compared to gene expression in control cells (see, Trevillyan et al (2001) J. Biol. Chem. 276:48118-26). In other embodiments, expression of endogenous or recombinant IL-2 mRNA or protein is assessed.

T Cell Proliferation

Cytokines such as IL-2 are necessary for T-cell proliferation in response to mitogen or alloantigen stimulation, and thus T-cell proliferation is altered by changes in cytokine expression or secretion. In some embodiments, T cells are induced, such as with concanavalin A or alloreactive lymphocytes and T cell proliferation measured, for example, by subjecting cells to a pulse of $^3$H-thymidine and measuring $^3$H-thymidine incorporation (see, Trevillyan et al. (2001) J. Biol. Chem. 276:48118-26).

In further embodiments, the modulation (e.g. inhibition or reduction) of SOCE by compounds capable of modulating intracellular calcium levels is determined by evaluation of any of the following criteria:

a. there is direct inhibition of increased $[Ca^{2+}]_i$ as measured by a calcium indicator;

b. there is a direct inhibition of $I_{SOC}$ or $I_{CRAC}$ as measured by patch clamp;
c. there is inhibition of downstream signaling functions such as calcineurin activity, NFAT subcellular localization, NFAT phosphorylation, and/or cytokine, e.g., IL-2, production; or
d. there are modifications in activation-induced cell proliferation, differentiation and/or apoptotic signaling pathways.

Animal Models

Animal models that are used in embodiments of the methods further include animals, such as, but not limited to non-human animals, which have, in at least some of their cells, an alteration or defect in, or aberrant functioning of, a cellular process which relies on or is regulated by intracellular calcium. Cellular processes that rely on or are regulated by intracellular calcium include, for example, cellular activation, gene expression, cellular trafficking, and apoptosis. In some embodiments, are diseases/disorders that involve defects that are at least partially compensated for by modulation of intracellular calcium include, but are not limited to: autoimmune disorders, including rheumatoid arthritis, inflammatory bowel disease, Sjogren's syndrome (cytokines associated with lymphocyte invasion of salivary epithelial cells generally reduce calcium mobilization in parotid cells; also, T-cell activation, including activation of transcription factors, cytokine gene expression and cell proliferation, depends on sustained elevation of intracellular calcium level provided by store-operated calcium influx), asthma (store-operated calcium entry also plays an important role in mediating bronchial chonstriction and bronchial smooth muscle cell proliferation), glomerulonephritis and glomerular inflammation (changes in intracellular calcium, such as by store-operated calcium entry, signal monocyte adhesion in a co-culture model of glomerular inflammation).

Types of animal models include, but are not limited to, non-human animals, such as non-human invertebrates and vertebrates and non-human mammals, rodents (e.g., mice, rat and hamster), cows, chickens, pigs, goats, dogs, sheep, insects, *Drosophila*, nematodes, worms, *C. elegans*, monkeys, gorillas, and other primates.

Animal models include transgenic and non-transgenic animals. One example of such an animal model that are used in particular embodiments of the methods is a rodent model of airway hyperresponsiveness (AHR), a characteristic of asthma. This model are generated, for example, by sensitization through immunization with ovalbumin followed by exposure to aerosolized ovalbumin and challenge by cholinergic stimulation (e.g., via administration of methacholine or acetylcholine) (see, e.g., Xu et al. (2002) *J. Appl, Physiol.* 93:1833-1840; Humbles et al (2002) *Proc, Natl. Acad. Sci.* 99:1479-1484). Airway hyperresponsiveness (which in some embodiments are evaluated using methods such as, for e.g., using barometric plethysmography to record respiratory pressure curves and through measurement of pulmonary parameters such as pulmonary conductance and pulmonary compliance) are assessed and compared in animals treated and not treated with compounds capable of modulating intracellular calcium levels. A further example of an animal model that is used in embodiments of the methods is a rodent model of mesangial proliferative glomerulonephritis, which is generated, for example, by administration of anti-Thy1.1 antibody (see, e.g., Jefferson and Johnson (1999) *J. Nephrol.* 12:297-307). Any number of parameters indicative of glomerulonephritis or renal dysfunction (e.g., mesangial cell proliferation, blood pressure, urinary protein excretion, creatinine clearance, glomerulosclerosis index and other parameters) are in some embodiments, evaluated and compared in animals treated with and not treated with test agent. The non-obese diabetic (NOD) mouse, an inbred mouse strain that spontaneously develops an autoimmune diabetes that shares many Immunogenetics features with Type 1 diabetes mellitus, is another example of an animal model that is used in one embodiment of the methods. These mice also manifest many characteristics of autoimmune exocrinopathy (such as Sjorgen's syndrome) including declining exocrine tissue secretory function (see, e.g., Humphreys-Beher and Peck (1999) *Arch. Oral Biol.* 44 Suppl 1:S21-25 and Brayer et al. (2000) *J. Rheumatol.* 27:1896-1904). Characteristics relevant to Sjorgen's syndrome (e.g., lymphocytic infiltrates in exocrine glands (e.g., salivary and lacrimal glands), presence of dendritic cells and macrophages in submandibular glands, integrity of the lacrimal gland by measurement of basal and stimulated tear secretion, saliva flow rates and amylase activity) are evaluated and compared in animals treated with and not treated with compounds capable of modulating intracellular calcium levels. In further embodiments, an animal (e.g., rodent) model of autoimmune disease is also used in particular embodiments of the methods. Such animals include rat models available through the National Institutes of Health (NIH) Autoimmune Rat Model Repository and Development Center (Bethesda, Md.; accessible at www.ors.od.nih.gov/dirs/vrp/ratcenter). One rat model of rheumatoid arthritis (RA) and related chronic/inflammatory autoimmune diseases is the collagen-induced arthritis (CIA) model (see, e.g., Griffiths and Renimers (2001) *Immunol. Rev.* 184:172-183). Characteristic phenotypes of autoimmune disease (e.g. altered levels of immune reactivity to self-antigens, chronic inflammation of autoantigen-expressing target organs, and activation and participation of invading mononuclear cells and tissue fibroblasts in organ damage) are in some embodiments, evaluated and compared in animals treated with and not treated with compounds capable of modulating intracellular calcium levels. In other embodiments, an animal (e.g., rodent) model of neuropathic or inflammatory pain is also used in one embodiment of the methods. For example, one rat model of neuropathic pain involves development of tactile allodynia (exaggerated response to otherwise innocuous stimuli) after ligation of lumbar spinal nerves (see, e.g., Chaptan et al (1994) *J. Neurosci. Methods* 53:55-63 and Luo et al. (2001) *J. Neurosci.* 21:1868-1875). Tactile allodynia, one characteristic feature of neuropathic pain, are evaluated (e.g., by evaluating paw withdrawal threshold in response to application of pressure) and compared in animals treated and not treated with compounds capable of modulating intracellular calcium levels.

EXAMPLES

Example 1

Identification of Protein Components of the CRAC Channels: Synergistic Action of Stim and Orai Transfected Proteins in *Drosophila* Cells Molecular Cloning. A cDNA clone, pAc5.1/olf186-F, encoding full-length Drosophila olf186-F-RB, was generated for transfection into S2 cells. Briefly, a 1.1-kb fragment was isolated from total mRNA of Drosophila S2 cells by RT-PCR and subcloned between the XhoI and NotI sites of pAc5.1N5-His B expression vector. Primers were designed based on the deposited flybase sequence of olf186-F(CG11430RB). Resulting clones were sequenced (GenBank accession no. DQ503470 (SEQ ID NO: 24)). Generation of pAc5.1/EGFP and pAc5.1/D-STIM have been described.

TABLE 1

Solutions for $Ca^{2+}$ imaging and whole-cell recording

| Name | $Na^+$ | $K^+$ | $Ca^{2+}$ | $Mg^{2+}$ | CT | HEPES | pH | Osmolality |
|---|---|---|---|---|---|---|---|---|
| S2 Ringer (Ca2) | 150 | 5 | 2 | 4 | 167 | 10 | 7.2 | 328 |
| $Ca^{2+}$-free S2 Ringer (Ca0) | 150 | 5 | — | 6 | 167 | 10 | 7.2 | 332 |
| S2 external (Ca2) | 160 | — | 2 | — | 164 | 10 | 6.6 | 325 |
| High-$Ca^{2+}$ S2 external (Ca20) | 124 | — | 20 | — | 164 | 10 | 6.6 | 324 |
| Divalent free $Na^+$ (Na) | 152 | — | — | — | 152 | 10 | 6.6 | 328 |
| Divalent free $Cs^+$ (Cs) | 160 | — | — | — | 164 | 10 | 6.6 | 324 |

| Name | $Cs^+$ aspartate | CsCl | $Mg^{2+}$ gluconate | HEPES | pH | Osmolality |
|---|---|---|---|---|---|---|
| S2 internal | 133 | 2 | 8 | 15 | 7.2 | 320 |

Ringer solutions were used for $[Ca^{2+}]_i$ imaging; external solutions were used in patch-clamp experiments. Concentrations are in mM, and osmolality is in mOsm/kg. S2 Ringer solutions contained 2.5 mM probenecid. $Ca^2$-free Ringer and external solutions contained 1 mM EGTA. All Ringer and external solutions contained 10 mM d-glucose. High-$Ca^{2+}$ external solution contained 10 mM sucrose. Internal solutions contained 12 mM BAPTA. pH was adjusted with the appropriate hydroxide.

A scatter plot showed reasonable agreement for the replicate assays for most amplicons, particularly for hits with reduced $Ca^{2+}$ influx reflected in lower CCE/basal values. Because most amplicons did not influence the dynamics of $Ca^{2+}$ signaling, the average for a given plate was very close to that of nontreated wells. Therefore, z-scores of basal/EF and CCE/basal equal to the value of the well minus the average of the plate divided by the standard deviation for the plate were calculated for each well. The averaged z-scores represent variations in the distribution of CCE/basal measurements for each amplicon. Hits in the screen, defined by values of >3 standard deviations from the mean (z-score <-3 or >3) fell into four categories: (t) decreased resting $[Ca^{2+}]_i$; (ii) increased resting $[Ca^{2+}]_i$; (iii) decreased CCE (Table 2); and (iv) increased CCE. To eliminate false-positive outcomes, putative hits with a z-score of $F_{max} < -2$, or with more than five off-targets, were generally filtered out from the lists. Overlapping hits between groups i and iv and groups ii and iii were removed from group iv and iii, respectively.

Cell Culture and Transfection. *Drosophila* S2 cells (Invitrogen) used in the RNAi screen, single cell imaging, and patch-clamp experiments were propagated in Schneider's medium (Invitrogen) supplemented with 10% FBS (Invitrogen) at 24° C. Cells were seeded at a density of $10^6$ cells per ml and passaged when the cells achieved a density of $6 \times 10^6$ cells per ml. S2 cells were transfected (see clones described later) using a Nucleofector (Amaxa, Gaithersburg, Md.) following the manufacturer's protocol. Forty-eight hours after transfection, cells were used for patch-lamp experiments or processed for RT-PCR analysis.

Molecular Cloning. A cDNA clone, pAc5.1/olf186-F, encoding full-length *Drosophila* olf186-F-RB, was generated for transfection into S2 cells. Briefly, a 1.1-kb fragment was isolated from total mRNA of *Drosophila* S2 cells by RT-PCR and subcloned between the XhoI and NotI sites of pAc5.1/V5-His B expression vector. Primers were designed based on the deposited flybase sequence of olf186-F (CG11430RB). Resulting clones were sequenced (GenBank accession no. DQ503470). Generation of pAc5.1/EGFP and pAc5.1/D-STIM have been described.

Preparation of dsRNA for Validation at Single-Cell Level. PCR templates for dsRNA synthesis were either from the *Drosophila* RNAi Screening Center (DRSC) stock or were analyzed by RT-PCR from cultured S2 cells (olf186-F). Primers were designed based on the original amplicon sequences to produce ≈500-bp fragments with T7 polymerase binding sites on both sense and antisense strands. For PCR primer pairs, see Table 2. The MEGAscript RNAi kits (Ambion, Austin, Tex.) were used to synthesize the dsRNA according to manufacturer's protocol. The concentration of dsRNA was determined by optical density at 260 nm.

TABLE 2

Primers

| Gene | Primer | Primer sequence 5' to 3' |
|---|---|---|
| *Drosophila* dsRNA primers (T7 sequence underlined) | | |
| olf186-F | olf186-F-RNAi F1 | GAATTAATACGACTCACTATAGGGAGAATACGAATGTACCACCGGG (SEQ ID NO: 2) |
| | olf186-F-RNAi R1 | GAATTAATACGACTCACTATAGGGAGACCAAGTGATGCTAGACAATGT (SEQ ID NO: 3) |
| Cloning primers | | |
| olf186-F | olf186-F-clone F1 | CTGAACATGAAGCGGCCGCATCATGTCTGTGTGGACCAC (SEQ ID NO: 4) |
| | olf186-F-clone R1 | GCTGAACTCGAGCTAGACAATGTCCCCGGATG (SEQ ID NO: 5) |

TABLE 2-continued

Primers

| Gene | Primer | Primer sequence 5' to 3' |
|---|---|---|
| RT-PCR primers | | |
| olf136-F | olf186-F-RT F1 | GAATTAATACGACTCACTATAGGGAGAATACGAATGTACCACCGGG (SEQ ID NO: 2) |
| | olf186-F-RT R1 | GAAAGAGTATGAGTCCCAGC (SEQ ID NO: 6) |
| | olf186-F-RT F2 | CCAACAATTCGGGCCTAGAGAC (SEQ ID NO: 7) |
| | olf186-F-RT R2 | GTAGGTGGGCGAGTGGAGATC (SEQ ID NO: 8) |
| Stim | Stim-RT F1 | CAGTGGAAGTGTTCAGGATCGC (SEQ ID NO: 9) |
| | Stim-RT R1 | CCACATCCATTGCCTTCAATGAG (SEQ ID NO: 10) |
| CG11059 | CG11059-RT F1 | CTCGCCTAGACTTATGTGAC (SEQ ID NO: 11) |
| | CG11059-RT R1 | CCAGTAGACCCATCAAAGTG (SEQ ID NO: 12) |
| Presenilin (Psn) | PSN-RT F1 | CTACGGAGGCGAACGAACG (SEQ ID NO: 13) |
| | PSN-RT R1 | GGCGATTGTTCATGGAAAGG (SEQ ID NO: 14) |
| Ca-P60A | CaP60A-RT F1 | CGATATCCGTATCACCCACA (SEQ ID NO: 15) |
| | CaP60A-RT R1 | CTCACCGAACTCGTCCAGTT (SEQ ID NO: 16) |
| Syntaxin 5 (Syx5) | Syx5-RT F1 | CGCTTCCATTCCGACTAGTT (SEQ ID NO: 17) |
| | Syx5-RT R1 | GCTTCTCCAGTTTTGCGTAG (SEQ ID NO: 18) |
| tsr | Tsr-RT F1 | GAAATGCGGACCTGGAGAGT (SEQ ID NO: 19) |
| | Tsr-RT R1 | CGACTTCTTGAGAGCATCGA (SEQ ID NO: 20) |

RNAi in *Drosophila* S2 Cells. RNAi experiments were adapted from the protocols described by Worby et al. *Drosophila* S2 cells ($0.5 \times 10^6$) were seeded in T-25 flasks in 2 ml of complete S2 medium. The next day, medium was removed and replaced with 2 ml of serum-free S2 medium. Twenty micrograms of dsRNA was added, and cells were incubated at room temperature for 45 min with gentle rocking. Four milliliters of S2 medium was added, and cells were incubated for 5 days at 24° C. Cells then were harvested and either plated for single-cell $Ca^{2+}$ imaging and patch-clamp experiments or processed for RT-PCR analysis.

RNA Isolation and RT-PCR. RNA was isolated using TRIzol (Invitrogen) following the manufacturer's protocols. The total RNA yield was calculated from the $OD_{260}$ of the RNA preparation. RNA quality was determined from the absorbance ratio $OD_{260}/OD_{290}$ (>1.8). In each sample, total RNA (3 μg) was reverse-transcribed using the Superscript Preamplification System (Invitrogen). The sense and antisense primers were specifically designed from the coding regions of our targeted genes (Table 4). The fidelity and specificity of the sense and antisense oligonucleotides were examined using the BLAST program. PCR reactions were performed by DNA thermal cycler (Bio-Rad) using Platinum PCR Supermix High Fidelity (Invitrogen). The first-strand cDNA reaction mixture (1 μm) was used in a 50-μl PCR reaction consisting of 0.2 μM paired primers. The cDNA samples were amplified under the following conditions: the mixture was denatured at 94° C. (30 s), annealed at 55° C. (30 s), and extended at 68° C. (30 s) for 25-27 cycles, followed by a final extension at 72° C. (10 min) to ensure complete product extension. The PCR products were electrophoresed through a 1.5% agarose gel, and amplified cDNA bands were visualized by GelStar (Cambrex, East Rutherford, N.J.) staining.

Single-Cell $[Ca^{2+}]_i$ imaging. Ratiometric $[Ca^{2+}]_i$ Imaging was performed as described in ref. 3, using solution recipes described in Table 3. Transfected cells were recognized by coexpressed enhanced GFP (EGFP), using filters to avoid contamination of Fura-2 fluorescence by bleedthrough of GFP fluorescence. Data were analyzed with METAFLUOR software (Universal Imaging, Downington, Pa.) and ORIGINPRO 7.5 software (OriginLab, Northampton, Mass.) and are expressed as means ±SEM.

Whole-Cell Recording. Patch-clamp experiments were performed at room temperature in the standard whole-cell recording configuration, using a holding potential of −10 mV. The recipes of external and internal solutions are indicated in Table 3. The membrane capacitance (a measure of cell surface area) of S2 cells selected for recording was 9.15±0.27 pF (mean±SEM, n=287 cells, 22 experiments). To calculate current densities, peak current amplitudes were divided by membrane capacitance for each cell. Liquid junction potentials were re-evaluated, resulting in a corrected $P_{Cs}/P_{Na}$ of 0.17, instead of 0.08, for both native CRAC current and current induced by coexpression of olf186-F and Stim.

Bioinformatics. The PHI-BLAST server at the National Center for Biotechnology Information was used to look for homologous proteins of the *Drosophila* olf186-F gene product. The criteria used were: E value $<1\times10^{-20}$, and the length of homology regions must be at least ⅔ of the full proteins. The sequences of all family members identified were clustered using CLUSTALW, and a phylogenetic tree (phylogram) was generated according to the mutual similarity among the members.

Figure 2:
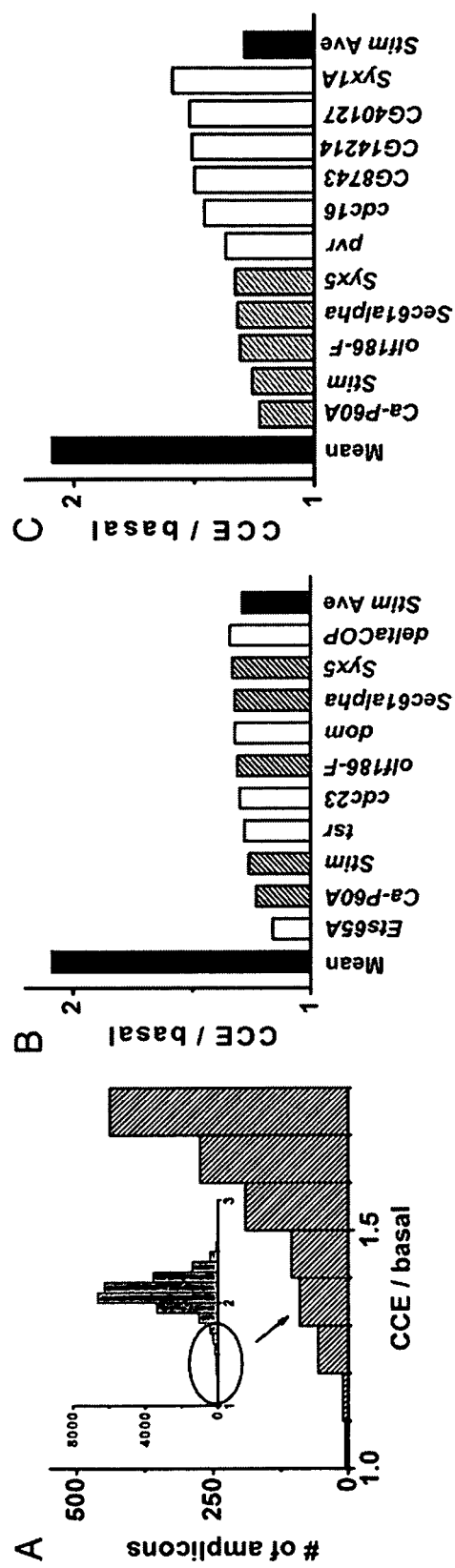
FIG. 2 describes the identification of genes involved in store-operated calcium entry. (A) The effect of individual gene silencing on TG-evoked $Ca^{2+}$ entry (CCE) relative to basal $Ca^{2+}$, displayed as a histogram. (inset) The distribution of averaged CCE/basal values for each well. Low values of CCE/basal are enlarged to show the tail of the distribution, representing amplicons that dramatically suppressed TG-evoked calcium entry. (B) The top 10 hits with strongest effect on TG-evoked $Ca^{2+}$ influx. Averaged values of CCE/basal are shown for all 48,384 wells tested in the assay ("mean"), for the top 10 hits from the screen, and for the positive control well that contained Slim dsRNA in each assay plate ("Stim Ave"). Striped bars represent hits with transmembrane regions. (C) Transmembrane (TM) protein hits.

Results and Analysis—Genome-Wide Screen for SOC Influx. Each well of 63 separate 384-well plates contained an individual dsRNA amplicon. $Ca^{2+}$-indicator fluorescence measurements were made in each well to monitor cytosolic $Ca^{2+}$ ($[Ca^{2+}]_i$) before (basal) and after [capacitive calcium entry (CCE)] addition of TG. TG inhibits SERCA pump-mediated reuptake of $Ca^{2+}$ into cellular stores, depleting them and triggering CCE in S2 cells, as well as in mammalian cells. Hits in the screen were defined by significantly reduced CCE/basal values, and illustrated by a tail in the histogram shown in FIG. 2A. The "top 10 hits," with strong suppressive effects comparable with the average value of the Stim positive control (CCE/basal≈1.3), were selected for further evaluation (FIG. 2B; see also Table 3).

TABLE 3

Top 10 hits involved in store-operated $Ca^{2+}$ entry

| DRSC amplicon | Target gene | CCE/basal | basal/$F_{max}$ | Z of $F_{max}$ | Predicted TM segments | Putative function | Potential off-targets |
|---|---|---|---|---|---|---|---|
| DRSC11164 | Ets65A | 1.16 | 0.23 | −0.35 | 0 | Transcription factor | 0 |
| DRSC04600 | Ca-P60A | 1.23 | 0.37 | 0.43 | 8 | SERCA pump | 0 |
| DRSC20158 | Stim | 1.26 | 0.28 | −1.03 | 1 | Putative ER $Ca^{2+}$ sensor for SOC activation | 0 |
| DRSC04718 | tsr | 1.28 | 0.37 | 0.56 | 0 | Actin binding protein | 0 |
| DRSC02708 | cdc23 | 1.30 | 0.35 | −1.69 | 0 | Component of anaphase-promoting complex for mitotic anaphase | 1 |
| DRSC22061 | olf186-F | 1.31 | 0.29 | −1.11 | 4 | *Drosophila* CRAC candidate | 0 |
| DRSC04558 | Dom | 1.32 | 0.35 | 0.38 | 0 | Component of chromatin remodeling complex for DNA recombination | 0 |
| DRSC03256 | Sec61alpha | 1.32 | 0.41 | 1.40 | 10 | Component of translocon complex for protein trafficking | 0 |
| DRSC03432 | Syx5* | 1.33 | 0.33 | −2.21 | 1 | t-SNARE protein for vesicle fusion | 0 |
| DRSC18760 | deltaCOP | 1.34 | 0.32 | −1.39 | 0 | Component of COPI complex for protein trafficking | 0 |

DRSC, *Drosophila* RNAi Screening Center at Harvard University.

Among the 75 filtered hits with z-scores of CCE/basal<−3 (see Table 4), only 11 contained transmembrane segments, as shown in FIG. 2C. Among these hits, the five strongest are annotated in Flybase (www.flybase.org) as Ca-P60A, Stim, olf186-F, sec61alpha, and Syx5.

TABLE 4

Group 3 hits, decreased CCE

| DRSC amplicon | Target gene | CCE/basal | Basal/$F_{max}$ | Z of $F_{max}$ | Potential off-targets |
|---|---|---|---|---|---|
| DRSC00777 | Rab5 | 1.41 | 0.40 | 2.98 | 1 |
| DRSC02278 | CG13773 | 1.45 | 0.40 | −1.48 | 0 |
| DRSC03611 | smt3 | 1.36 | 0.37 | −1.69 | 0 |
| DRSC03342 | Hel25E | 1.40 | 0.30 | −1.08 | 0 |
| DRSC03574 | mts | 1.36 | 0.28 | 0.43 | 0 |
| DRSC03080 | Pvr | 1.37 | 0.39 | −1.58 | 0 |
| DRSC03256 | Sec61alpha | 1.32 | 0.41 | 1.40 | 0 |
| DRSC02179 | CG12750 | 1.35 | 0.31 | −1.91 | 0 |
| DRSC02708 | cdc23 | 1.30 | 0.35 | −1.69 | 1 |
| DRSC04600 | Ca-P60A | 1.23 | 0.37 | 0.43 | 0 |
| DRSC04558 | dom | 1.32 | 0.35 | 0.38 | 0 |
| DRSC08370 | CG13900 | 1.47 | 0.29 | −1.74 | 0 |
| DRSC07000 | Bap55 | 1.54 | 0.28 | 2.89 | 0 |
| DRSC07659 | pAbp | 1.38 | 0.34 | −1.75 | 0 |
| DRSC06044 | DMAP1 | 1.54 | 0.31 | 1.42 | 0 |
| DRSC11164 | Ets65A | 1.16 | 0.23 | −0.35 | 0 |
| DRSC11032 | CG8743 | 1.50 | 0.34 | 2.95 | 0 |
| DRSC11257 | Prosbeta2 | 1.52 | 0.33 | −1.55 | 0 |
| DRSC11124 | CycT | 1.47 | 0.33 | −1.66 | 4 |
| DRSC12536 | CG1249 | 1.54 | 0.27 | −1.65 | 0 |
| DRSC15625 | CG4699 | 1.55 | 0.32 | −0.17 | 0 |
| DRSC15948 | CG6015 | 1.55 | 0.30 | −1.53 | 0 |
| DRSC15166 | CG16941 | 1.53 | 0.28 | −1.67 | 0 |
| DRSC16034 | Dis3 | 1.42 | 0.30 | −1.52 | 0 |
| DRSC16839 | Rpn2 | 1.41 | 0.33 | −1.87 | 0 |
| DRSC18760 | deltaCOP | 1.34 | 0.32 | −1.39 | 0 |
| DRSC18360 | APC4 | 1.54 | 0.36 | −0.27 | 0 |
| DRSC20158 | Stim | 1.26 | 0.28 | −1.03 | 0 |

TABLE 4-continued

Group 3 hits, decreased CCE

| DRSC amplicon | Target gene | CCE/ basal | Basal/$F_{max}$ | Z of $F_{max}$ | Potential off-targets |
|---|---|---|---|---|---|
| DRSC00782 | RpL40 | 1.58 | 0.31 | −1.28 | 0 |
| DRSC03261 | CG9548 | 1.58 | 0.30 | −1.55 | 0 |
| DRSC02680 | CG18591 | 1.61 | 0.28 | −1.78 | 0 |
| DRSC02721 | Vha68-2 | 1.64 | 0.32 | 0.31 | 0 |
| DRSC02868 | Pect | 1.65 | 0.28 | 1.74 | 0 |
| DRSC04718 | tsr | 1.28 | 0.37 | 0.56 | 0 |
| DRSC04884 | Nipped-A | 1.54 | 0.36 | −1.17 | 0 |
| DRSC04838 | Bub1 | 1.59 | 0.36 | −1.38 | 0 |
| DRSC06417 | MrgBP | 1.56 | 0.34 | −1.42 | 0 |
| DRSC06421 | CG30349 | 1.59 | 0.32 | −1.73 | 0 |
| DRSC07501 | Pabp2 | 1.42 | 0.31 | −1.50 | 0 |
| DRSC07408 | E(Pc) | 1.48 | 0.34 | 2.04 | 0 |
| DRSC07575 | RacGAP50C | 1.62 | 0.26 | 2.70 | 0 |
| DRSC07583 | betaTub56D | 1.55 | 0.34 | −1.91 | 2 |
| DRSC07502 | hrg | 1.53 | 0.36 | 0.77 | 0 |
| DRSC08730 | pav | 1.55 | 0.34 | 1.31 | 1 |
| DRSC10696 | CG6694 | 1.58 | 0.31 | −1.59 | 0 |
| DRSC09740 | sti | 1.50 | 0.27 | 0.48 | 0 |
| DRSC11079 | CG9598 | 1.69 | 0.34 | 1.36 | 0 |
| DRSC11330 | brm | 1.54 | 0.33 | −1.38 | 0 |
| DRSC11663 | CG11451 | 1.52 | 0.34 | −1.10 | 0 |
| DRSC12351 | Gnf1 | 1.57 | 0.35 | −1.49 | 0 |
| DRSC12623 | alphaTub84D | 1.45 | 0.35 | −1.52 | 2 |
| DRSC14371 | CG31258 | 1.53 | 0.32 | −1.50 | 0 |
| DRSC16555 | bel | 1.56 | 0.30 | 3.39 | 3 |
| DRSC16899 | alphaTub85E | 1.39 | 0.37 | −0.46 | 3 |
| DRSC16940 | eff | 1.41 | 0.33 | −1.60 | 0 |
| DRSC16808 | Rab1 | 1.40 | 0.34 | −1.50 | 0 |
| DRSC16938 | eIF-3p66 | 1.41 | 0.36 | −1.65 | 0 |
| DRSC16704 | Hmgcr | 1.44 | 0.36 | −1.26 | 0 |
| DRSC16920 | cdc16 | 1.46 | 0.38 | −0.89 | 0 |
| DRSC18483 | Roc1a | 1.64 | 0.31 | −1.32 | 0 |
| DRSC18713 | Rpt4 | 1.37 | 0.34 | −0.97 | 0 |
| DRSC19385 | CG11138 | 1.50 | 0.30 | −0.21 | 3 |
| DRSC19570 | CG14214 | 1.51 | 0.33 | −0.69 | 1 |
| DRSC21306 | xmas-2 | 1.63 | 0.35 | −1.55 | 0 |
| DRSC05281 | E(Pc) | 1.56 | 0.34 | 3.86 | 0 |
| DRSC09005 | dpr6 | 1.47 | 0.29 | −1.54 | 2 |
| DRSC09132 | CycA | 1.57 | 0.29 | 1.24 | 0 |
| DRSC04725 | zip | 1.59 | 0.26 | 1.58 | 0 |
| DRSC18419 | dalao | 1.66 | 0.28 | 0.49 | 0 |
| DRSC21641 | CG40127 | 1.52 | 0.28 | 1.71 | 0 |
| DRSC21554 | Syx1A | 1.59 | 0.30 | 0.04 | 0 |
| DRSC21831 | swm | 1.66 | 0.29 | −1.12 | 0 |
| DRSC22061 | olf186-F | 1.31 | 0.29 | −1.11 | 0 |
| DRSC22489 | zip | 1.64 | 0.26 | 3.28 | 0 |
| DRSC23010 | Atx2 | 1.49 | 0.33 | 0.63 | 0 |

DRSC, *Drosophila* RNAi Screening Center at Harvard University.

The consistent suppressive effect of Stim dsRNA validates the present screen. However, Stim is unlikely to constitute the CRAC channel, because multiple transmembrane segments are found in all identified ion-channel pore-forming subunits. The protein product of sec61 alpha is a subunit of the translocon complex, which recognizes and delivers newly synthesized membrane proteins into ER, and is likely a hit in this screen by altering synthesis or localization of other essential components. Ca-P60A is the SERCA pump gene in fly, whose products are located in the ER for filling/refilling the $Ca^{2+}$ store. Syx5 generates a single transmembrane-soluble N-ethylmaleimide-sensitive (NSF8) attachment receptor (SNARE) protein (Syntaxin 5), which is essential for vesicle fusion and likely modulates CCE by altered protein trafficking rather than serving as the channel pore. Thus, among the top 10 hits, olf186-F is the only gene of unknown structure and function that is predicted to contain multiple transmembrane segments.

Figure 3:
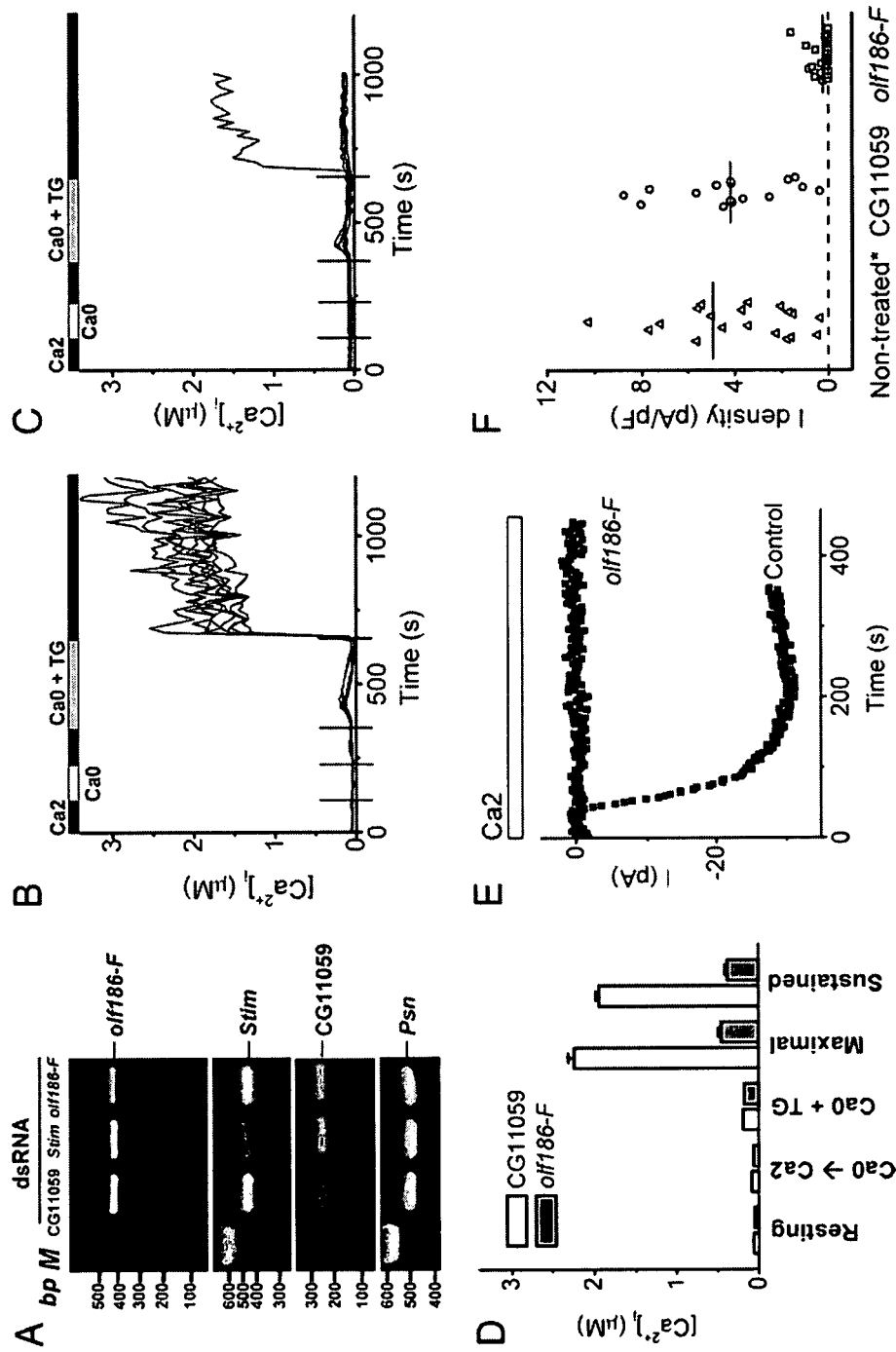
FIG. 3 depicts the suppression of TG-dependent $Ca^{2+}$ influx and CRAC current by olf186-F dsRNA. (A) Reduction of olf186-F mRNA expression in olf186-F dsRNA-treated cells. RT-PCR analysis on olf186-F, Stim, CG11059, and a control gene, Presenilin (Psn). (B) $[Ca^{2+}]_i$ in eight representative S2 cells treated with CG11059 dsRNA. Solution exchanges are indicated. (C) $[Ca^{2+}]_i$ in eight cells treated with olf186-F dsRNA. (D) Averaged $[Ca^{2+}]_i$ values ±SEM for control cells (n=195 cells in three experiments; white bars) and olf186-F dsRNA-treated cells (n=189 in four experiments; gray bars): resting $[Ca^{2+}]_i$, peak value upon readdition of 2 mM external $Ca^{2+}$ before TG treatment (Ca0–Ca2), peak $[Ca^{2+}]_i$ during TG-evoked release transient (Ca0+TG), and maximal and sustained (3 min) $[Ca^{2+}]_i$ after readdition of 2 mM external $Ca^{2+}$. (E) Representative time course of whole-cell currents recorded in control cells treated with CG11059 dsRNA and in cells treated with olf786-F dsRNA. (F) Suppression of CRAC current by olf186-F dsRNA pretreatment. Each point represents the maximal inward CRAC current density (pA/pF) in a single cell, plotted as absolute values in consecutive order from left to right within three groups of cells: untreated, cells treated with dsRNA to suppress CG11059, or olf186-F ($P<5\times10^{-6}$ compared with either control group). The untreated cell group includes two cells each with current density >12 pA/pF. Horizontal lines indicate the mean value of current density in each group.

Effects of olf186-F Knockdown and Overexpression on $Ca^{2+}$ Influx and CRAC Currents in Single Cells. To clarify effects of suppressing olf186-F at the level of single cells, we examined $Ca^{2+}$ signaling and CRAC currents in cells treated with dsRNA for olf186-F, in comparison with untreated cells or with cells treated with dsRNA for CG11059, an irrelevant cell adhesion molecule, as controls. RT-PCR showed >50% decrease of olf186-F mRNA expression, compared with controls (FIG. 3A). FIG. 3B illustrates ratiometric fura-2 $[Ca^{2+}]_i$ measurements before and after TG-evoked store depletion in eight individual control cells. Addition of TG in zero-$Ca^{2+}$ solution to deplete the store elicited a $Ca^{2+}$ release transient caused by net leak of $Ca^{2+}$ from the store when the reuptake pump is blocked. Upon readdition of external $Ca^{2+}$, a robust $Ca^{2+}$ signal was observed in every cell. In cells pretreated with olf186-F dsRNA, neither the resting $[Ca^{2+}]_i$ level nor the release transient were significantly altered, but the rise in $[Ca^{2+}]_i$ upon readdition of external $Ca^{2+}$ was strongly suppressed in the vast majority of the individual cells (FIG. 3C). FIG. 3D clearly demonstrates that suppression of olf186-F effectively inhibits both the early and sustained components of $Ca^{2+}$ entry evoked by TG at the single-cell level. Comparable inhibition was obtained in cells pretreated with Stim dsRNA as a positive control (data not shown).

Patch-clamp experiments confirmed a dramatic suppression of CRAC currents after knockdown of olf186-F F (FIGS. 3E and F). CRAC current normally develops after establishing the whole-cell recording configuration as the cytoplasm is dialyzed by a pipette solution containing a strong $Ca^{2+}$ chelator to reduce cytosolic $[Ca^{2+}]_i$ and deplete internal stores. With this method of "passive stores depletion," current increases after an initial delay to a maximum value before declining slowly. However, in the majority of cells pretreated with olf186-F dsRNA, CRAC current was completely suppressed, as illustrated by the representative traces in FIG. 3E and by a chart of CRAC current densities (FIG. 3F). Stim, olf186-F expression is required for normal CRAC channel activity.

Figure 4:
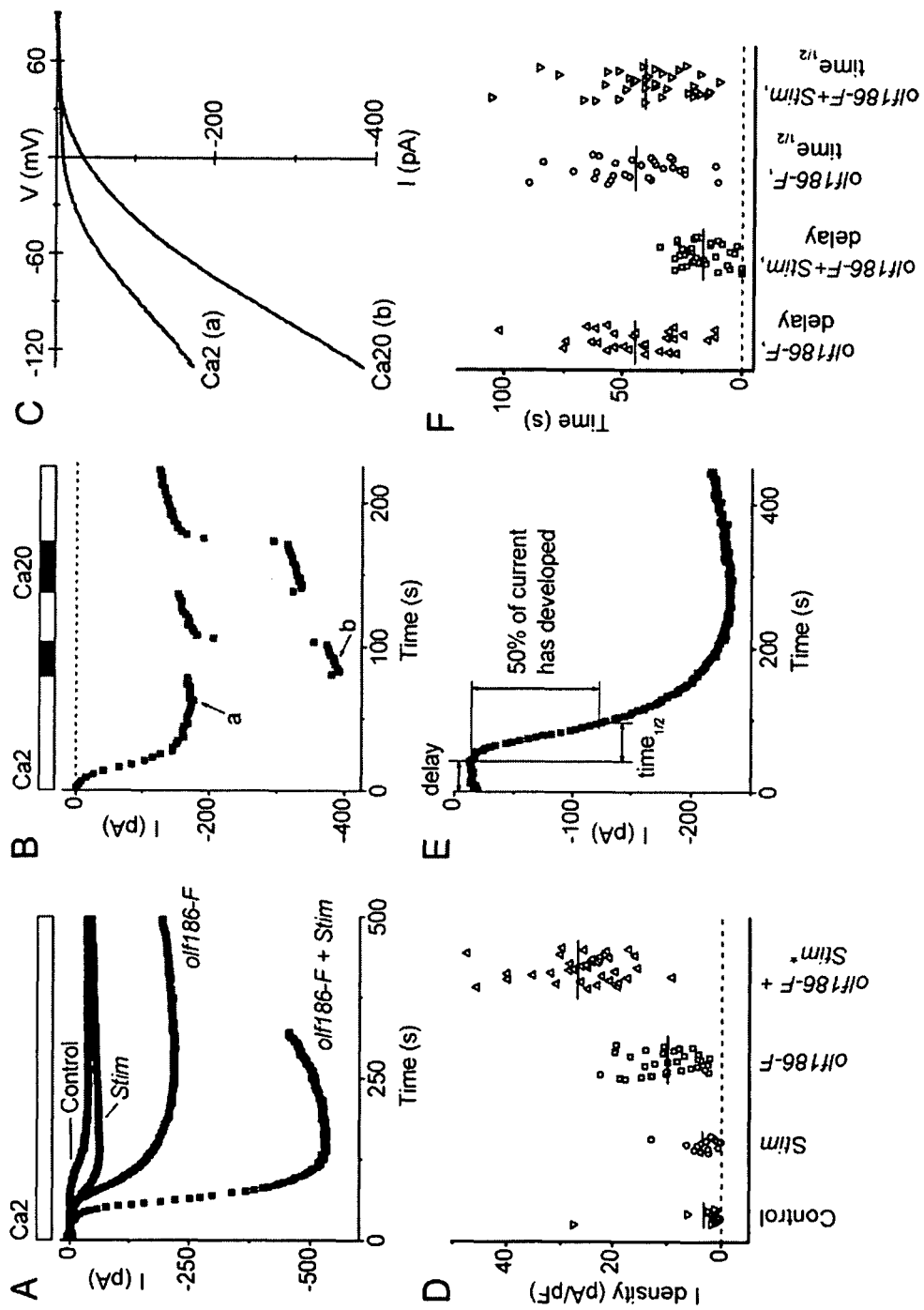
FIG. 4 depicts overexpression experiments of olf186-F leading to increased CRAC currents in S2 cells. (A) Representative CRAC currents in S2 cells transfected with GFP only (control), Stim, olf186-F, and olf186-F plus Stim. (B) $Ca^{2+}$ current in olf186-F+Stim cotransfected cell. Arrows a and b indicate the time corresponding to current-voltage curves in C. (C) Current-voltage relationship of CRAC current in the same cell. (D) CRAC current density in transfected S2 cells, plotted as in FIG. 2F, within four groups of cells: GFP-transfected control; Slim and GFP cotransfected (not significantly different from controls); olf186-F and GFP cotransfected ($P<10^{-3}$); and olf186-F, Stim, and GFP cotransfected ($P<5\times10^{-6}$). The group of cells cotransfected by olf186-F, Stim, and GFP includes one cell with current density >50 pA/pF. (B) Method to analyze kinetics of CRAC current development. (F) Effect of cotransfected Stim on delay kinetics. Delay times are significantly reduced ($P<5\times10^{-6}$), but $time_{1/2}$ values are not altered when Stim is expressed together with olf186-F, compared with olf186-F alone.

To examine further the function of olf186-F, we cloned its full-length cDNA from S2 cells and inserted it into a *Drosophila* expression vector. The olf186-F clone was overexpressed with or without a cotransfected Stim clone in S2 cells, by using a cotransfected GFP construct for identification of transfected cells. Increased expression levels of olf186-F and Stim after separate transfections or cotransfection were verified by RT-PCR (see FIG. 6A). FIG. 4A illustrates the time course of current development after break-in to achieve whole-cell recording in four representative cells. Expression of Stim by itself had no significant effect on current amplitude compared with control, untransfected cells. However, when olf186-F was overexpressed, CRAC current increased significantly, and when olf186-F was coexpressed with Stim, CRAC current was further enhanced. The induced current after cotransfection of olf186-F with Stim exhibited $Ca^{2+}$ selectivity and current-voltage shapes indistinguishable from native CRAC current (FIGS. 4B and C). When external $Ca^{2+}$ was elevated 10-fold, the current magnitudes approximately doubled, as is the case for native CRAC current in S2 cells, and current-voltage curves had the same inwardly rectifying characteristic. FIG. 4D illustrates CRAC current densities for individual cells in each group of transfected cells. Overexpression of olf186-F increased the average current density 3-fold, and although Stim by itself did not alter current density, cotransfection with olf186-F produced a remarkable 8-fold enhancement. Interestingly, cotransfection with Stim also decreased the initial delay to the onset of current development (FIGS. 4A, E, and F). Together, these results show that overexpression of olf186-F is sufficient to increase CRAC current density, that coexpression with Stim produces a further enhancement, and that interaction with Stim is likely a rate-limiting step for channel activation.

Figure 5:
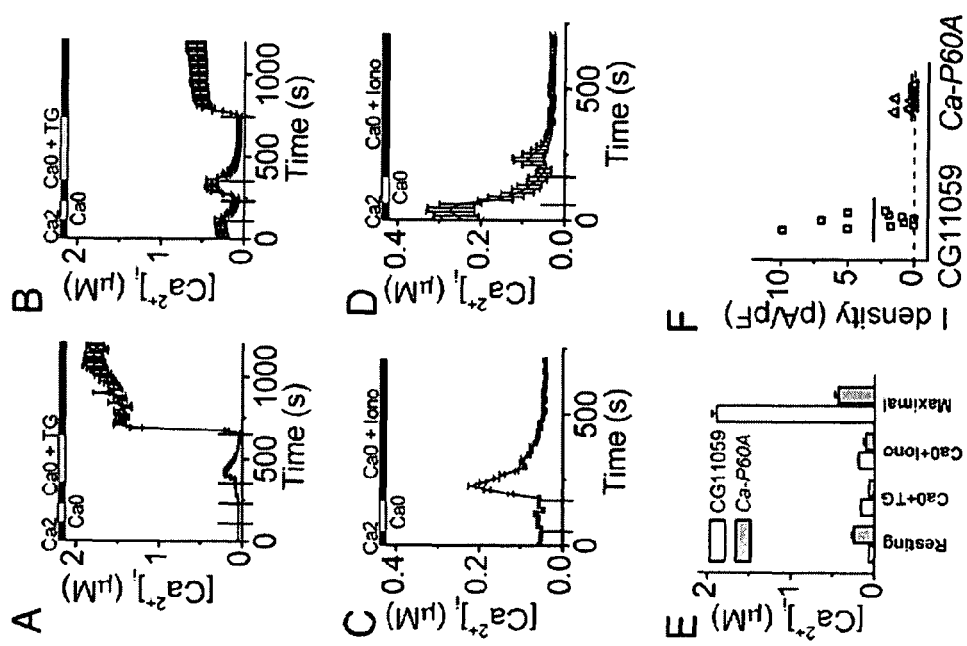
FIG. 5 depicts the effects of Ca-P60A ds RNA on $Ca^{2+}$ dynamics in individual S2 cells. (A) Averaged $[Ca^{2+}]_i$ in cells treated with control CG11059 dsRNA. (B) Averaged $[Ca^{2+}]_i$ in cells treated with Ca-P60A dsRNA. (C and D) $Ca^{2+}$ release evoked by 1 μM ionomycin in control cells and in cells treated with Ca-P60A dsRNA to knock down SERCA expression. (E) Averaged $[Ca^{2+}]_i$ values ±SEM for control cells (white bars) and Ca-P60A dsRNA-treated cells (gray bars) labeled as in FIG. 2D and including peak $[Ca^{2+}]_i$ during ionomycin-evoked release transient (Ca0+Iono). (F) Summary of inward CRAC current densities in control CG11059- and Ca-P60A dsRNA-treated cells (P=0.002), using the same plotting format as in FIG. 2F.

Apart from much larger current amplitudes, the $Ca^{2+}$-selective current in cells cotransfected with olf186-F and Slim exhibited biophysical properties that were indistinguishable from native CRAC currents. Monovalent ion selectivity upon removal of external $Ca^{2+}$ (divalent-free), $Na^+$ current inactivation, and potentiation of $Ca^{2+}$ current upon readdition of external $Ca^{2+}$ were similar to that described for native CRAC current in lymphocytes and S2 cells (see FIG. 5A). Current-voltage relations for the monovalent Nat current also showed inward rectification and a reversal potential of +45 mV (FIG. 5B), the same as native monovalent CRAC current and consistent with low permeability to $Ca^{2+}$. The response to voltage steps was also the same, with currents that increase slightly at very negative potentials (FIGS. 5C and D), as seen previously in S2 cells. Furthermore, the $Ca^{2+}$ current in olf186-F+Stim transfectants was sensitive to pharmacological agents that act on native CRAC currents (FIGS. 5E and F). $Gd^{3+}$ (50 nM) and 2-aminoethyldiphenyl borate (2-APB; 20 μM) blocked the enhanced $Ca^{2+}$ currents, and at lower concentration (5 μM) 2-APB exhibited a characteristic potentiation of current before blocking. In summary, the ion selectivity, development and inactivation kinetics, and pharmacological profile of the large induced $Ca^2$ current after overexpression of olf186-F plus Stim match native CRAC currents. Because the current is not enhanced by overexpression of Stim alone, these findings support the possibility that olf186-F itself is part of the channel.

Effects of Ca-P60A, Syx5 and tsr dsRNA Treatment on $Ca^{2+}$ Dynamics and CRAC Current. The SERCA pump also emerged from the RNAi screen as a putative regulator of SOC influx. However, because the screen was based on $Ca^{2+}$ influx induced by TG (which blocks the SERCA pump), we were concerned about the potential for a false-positive hit. We therefore performed single-cell $Ca^{2+}$ imaging and patch-clamp experiments using alternative stimuli (ionomycin, passive stores depletion) to deplete the $Ca^{2+}$ store. Selective lowering of Ca-P60A mRNA was first verified by RT-PCR (FIG. 6B). Knockdown of Ca-P60A significantly increased resting $[Ca^{2+}]_i$, reduced the store release transient upon addition of TG and strongly suppressed $Ca^{2+}$ influx upon readdition of external $Ca^{2+}$ (FIGS. 6A and B). In addition, ionomycin in zero-$Ca^{2+}$ solution applied to control cells evoked a sharp $Ca^{2+}$ release transient with a peak that averaged 200 nM, but a greatly reduced release transient in Ca-P60A dsRNA-treated cells (FIGS. 4C and D), indicating reduced $Ca^{2+}$ store content as a consequence of reduced SERCA pump activity. As shown by the summary of $Ca^{2+}$ imaging experiments (FIG. 4E), knockdown of SERCA has a strong $Ca^{2+}$ phenotype, raising resting $[Ca^{2+}]_i$, reducing release transients, and suppressing influx evoked by TG. Furthermore, patch-lamp experiments demonstrated that CRAC currents also were suppressed when stores were depleted passively by dialysis of a $Ca^{2+}$ chelator, confirming a requirement of Ca-P60A for activation of functional CRAC channels.

Figure 6:
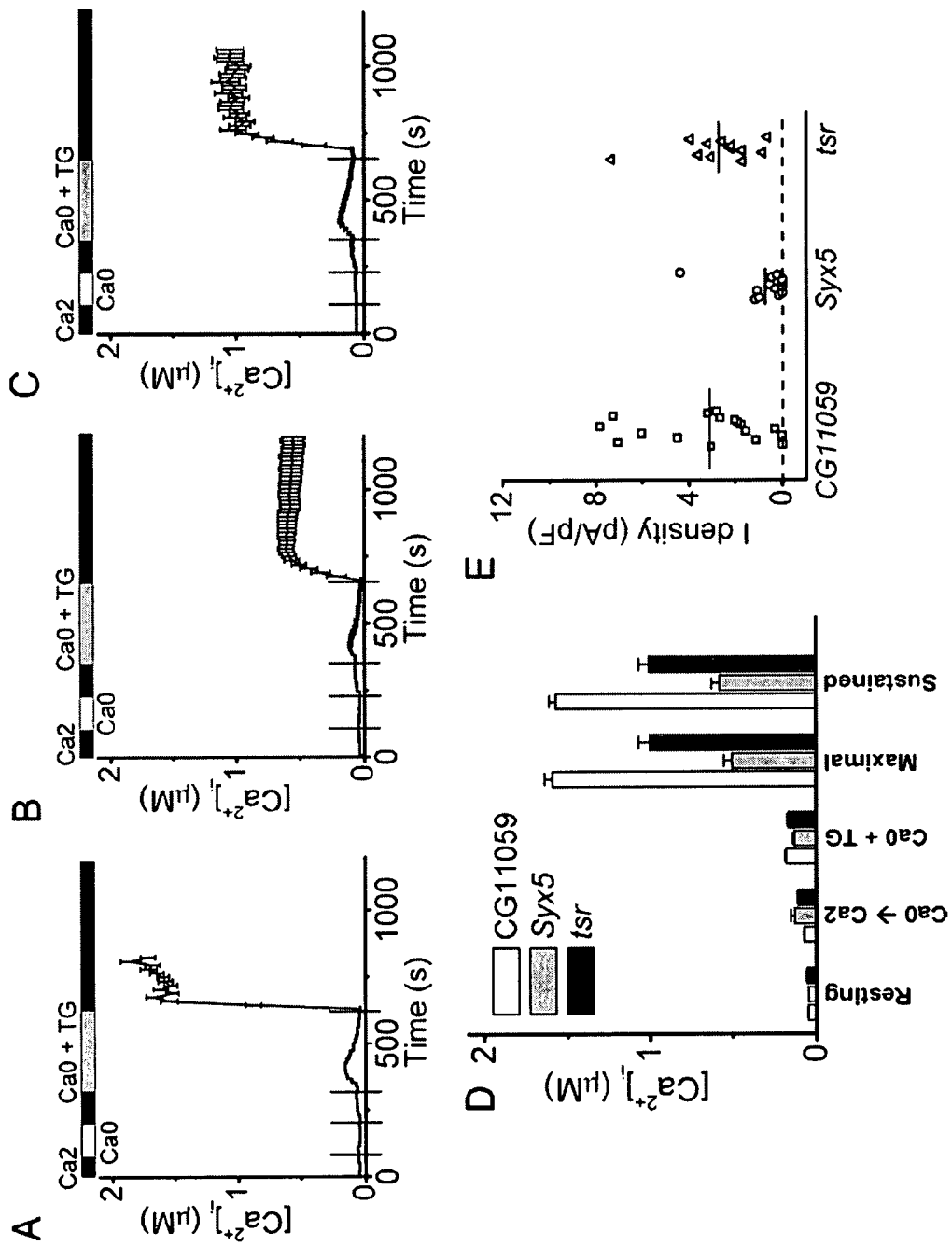
FIG. 6 depicts the suppression of $Ca^{2+}$ influx and CRAC current by Syx5 and tsr dsRNA. (A-C Averaged $[Ca^{2+}]_i$ in cells treated with control CG11059 dsRNA (A), Syx5 dsRNA (B), or tsr dsRNA (C). (D) Averaged $[Ca^{2+}]_i$ values ±SEM for control cells (white bars), Syx5 dsRNA-treated cells (gray bars), and tsr dsRNA-treated cells (black bars) labeled as in FIG. 2D. (E) Summary of inward CRAC current densities in Syx5 and tsr dsRNA-treated cells, using the same plotting format as in FIG. 2F. Mean values for CG11059 and Syx5 are significantly different (P=0.004). The mean values for CG11059 and tsr are not significantly different (P=0.65).

Several trafficking proteins also were identified as putative regulators of SOC activity (Table 2). Syx5 is a syntaxin, several of which have been implicated in SNARE complexes that regulate vesicle trafficking; and tsr is referred to as an actin-binding protein that regulates cytoskeleton remodeling. A putative role of its human homolog, cofilin, has been reported in activation of store-operated calcium entry in platelets. Both Syx5 and tsr dsRNA preincubation caused significant and selective lowering of mRNA levels (FIGS. 6 C and D) and a corresponding inhibition of TG-dependent $Ca^{2+}$ influx in S2 cells, without altering the resting $[Ca^{2+}]_i$ or store release (compare FIG. 6A-C). FIG. 6D summarizes the inhibition of TG-evoked $[Ca^{2+}]_i$ influx when Syx5 or tsr expression was knocked down. Patch-clamp experiments confirmed that CRAC currents were indeed suppressed during passive stores depletion when Syx5 was knocked down, but effects of tsr knockdown on CRAC currents did not achieve statistical significance (FIG. 6E).

Example 2

Stably Transfecting Cells with Orai1/STIM1

Jurkat T-cells are maintained in DMEM (Invitrogen cat#11960051), 10% FBS (Invitrogen cat#10082147), 1% Hepes (Invitrogen cat#15630080), 1% Sodium Pyruvate (Invitrogen cat#11360070), 1% Pen/Strep/Glutamine 100× (Invitrogen cat#10378016), 1 mL/L MEM NEAA 100× (Invitrogen cat#11140050), 1.5 g/L Sodium Bicarbonate (EMD cat#EM-SX0320-1), 2.5 mL/L Zeocin (Invitrogen cat#R25001), 20 mL/L Geneticin (G418) (Invitrogen cat#10131035). Cells are thawed by removing vials from liquid nitrogen and placing the vials in a 37° C. water bath until the frozen cells just begin to melt. The cells are diluted 1:10 with culture medium and transferred to a poly-D-lysine-(PDL, Sigma P-6407-5 mg) coated T-75 flask (coat flasks for 5 min with a solution of 1 mg PDL diluted into 50 mL water, then aspirate). Cells are Incubated at 37° C./6% $CO_2$ overnight. The next day, the cells are rinsed cells with 5-10 mLs D-PBS (Invitrogen cat#14190250), aspirated, and then added to 10 mLs fresh culture medium (to remove residual DMSO). The cells are monitored daily until the cells reach ~70% confluence (~1 week). The cells are expanded to PDL-coated T-150 flasks (pre-coated with 15 mLs PDL, as above).

The cells are passaged 1:3 every three days (when cells reach ~70% confluence). The cells should not go above 70% confluence, as the cells become unhealthy at higher confluence. When cells have reached confluence, the culture medium is aspirated and the cells rinsed with D-PBS. The cells are trypsinized in T-150 flask with 5 ml 0.25% trypsin (Invitrogen cat #15050065) and incubated for 5 minutes at 37° C./6% CO2. 5 mL culture medium is added to the flasks to inactivate the trysin, and the trypsinized cells triturated. 3.3 mL cells are transferred to 17 mL culture medium contained in a fresh PDL-coated T-150 flask.

Jurkat T-cells are stably co-transfected with a STIM1 nucleic acid and an Orai1 nucleic acid using calcium phosphate precipitation or electroporation methods. The co-transfected cells are monitored for co-expression of STIM1 and Orai1, isolated and propagated to form clonal populations.

Figure 7:
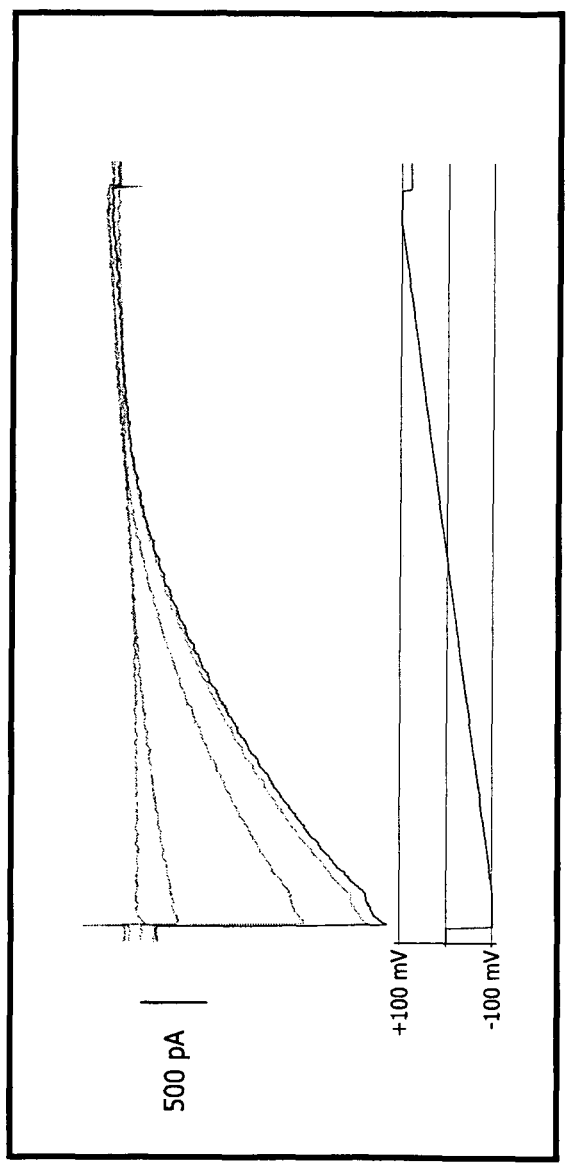
FIG. 7 depicts calcium current detected using patch claim analysis of cell lines stably expressed with Orai1/STIM1.
Figure 8:
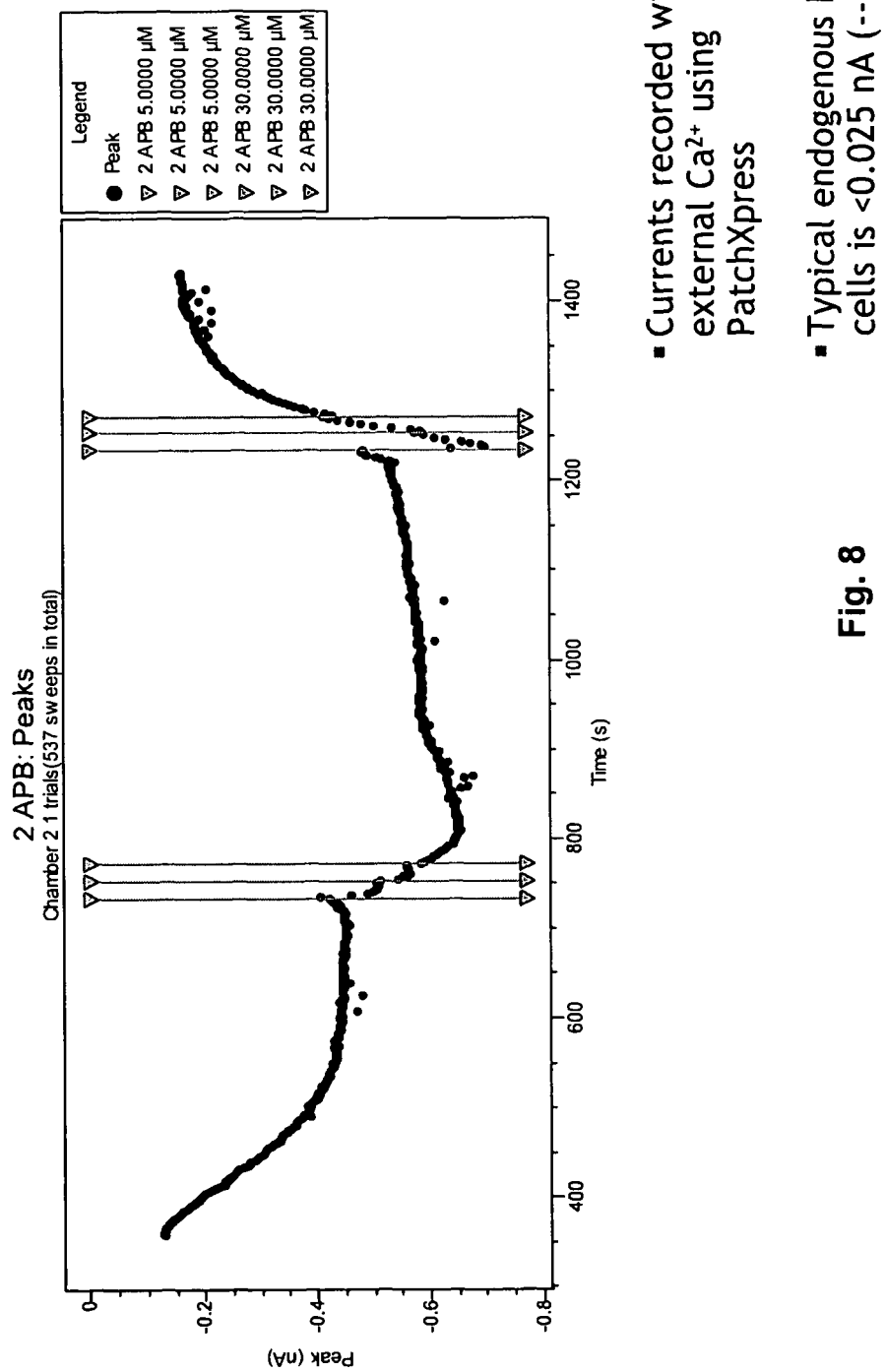
FIG. 8 depicts potentiation by 2-APB (2-aminoethoxydiphenyl borate) on CRAC channel currents using patch claim technology (PatchXpress).

Isolated, stably transfected cells were monitored with patch clamp analysis (PatchExpress) to detect calcium currents with overexpressed, stably transfected STIM1 and Orai1 nucleic acids. Stable, large and reproducible currents were detected, see FIG. 7. In addition, as seen in FIG. 8, sensitivity to 2-APB and $Gd^{3+}$ (data not shown), demonstrating that the currents detected represented bonafide $I_{CRAC}$ channel activity by virtue of these biophysical properties.

Example 3

Monitoring Protein Expression in Stably Transfected Cells

Western blot analysis is used to monitor protein STIM and Orai protein expression in stably transfected cells. Stim1 protein expression is monitored using a rabbit polyclonal antibody specific to STIM1. Orai1 protein expression is monitored using a mouse monoclonal antibody to a myc protein fragment, expressed as a tag on the C-terminal end of the expressed Orai1 protein.

4-20% acrylamide-15-well gels are prepared and used for Western blot analysis. Each well holds up to 17 µl sample. Samples are prepared by adding extracts to 2× sample buffer. The prepared gel wells are flushed by repeated pipetting and the samples loaded to each gel well. Benchmark Pre-stained Protein Ladder (5 ul/well) are loaded into one well for molecular weight reference. The gels are run at 150V (constant voltage) for 90 minutes. 2 Whatman paper and pre-cut nitrocellulose membrane (Invitrogen, Carlsbad, Calif.) are pre-soaked in transfer buffer (3.03 g Tris base, 14.1 g glycine, 20% MeOH, water to 1 liter). The gel plates are pried apart and Whatman paper placed over the gel; the gel is peeled from the plastic gel plate and placed onto a sponge, gel side up. The pre-wet nitrocellulose membrane is placed on top of the gel, taking care to remove any air bubbles by rolling a pencil or pipet piece over the 'gel sandwich'. The transfer cassette is closed and placed in the gel transfer apparatus by first filling the interior of the transfer cassette with transfer buffer, and filling the gel apparatus with water to cool unit while transferring. The proteins are transferred to nitrocellulose membrane at 25V (constant voltage) for 2 hours.

The transferred nitrocellulose membrane is first soaked in PonceauS stain 5 minutes, and the nitrocellulose membrane rinsed with water. The protein loading is then documented by photocopying or by scanning. The membrane is soaked in BLOTTO (PBS Tween (1 L PBS+0.05% Tween-20)+5 g instant milk/100 ml PBS-Tween, stored at 4° C.) for 30 minutes at room temperature on a place rocker. For a 10 cm plate, 10 ml of BLOTTO is used; for a 150 mm plate, 25 ml is used. The BLOTTO blocker is replaced with fresh BLOTTO, and the antibody added to the nitrocellulose membrane at the appropriate dilution. Commonly used antibody dilutions: Anti-GAPDH (Fitzgerald) 1:5000 (mouse monoclonal); Anti-STIM1 1:2000 (rabbit polyclonal); Anti-myc 1:1000 (mouse monoclonal). The membrane is incubated at 4° C. overnight on a plate rocker.

The nitrocellulose membrane is then washed 3× with BLOTTO, 10 minutes each wash at room temperature. Fresh BLOTTO is added and the appropriate secondary antibody (i.e. goat-anti-mouse for monoclonals; goat-anti-rabbit for polyclonals) at a dilution of 1:2500. The secondary antibod(ies) are incubated for 1 hour at room temperature on a plate rocker. The nitrocellulose membrane blot is washed 3-times with PBS-Tween, 10 minutes each wash at room temperature. The nitrocellulose membrane blot is placed on a plastic wrap or page protector, and the excess liquid removed. The signal is developed with an enhanced chemiluminescent ECL Western blot substrate (Amersham ECL or Pierce SuperSignal). For Amersham ECL, mix equal parts of solution A and solution B, and add to blot for 1 minute at room temperature. Remove excess liquid and expose to film. For Pierce SuperSignal, mix equal parts of solution A and solution B, and add to blot for 5 minutes at room temperature. Remove excess liquid and expose membrane to film. Take 1 second, 5 second, 1 minute and 5 minute exposures.

Example 4

Monitoring Intracellular Calcium Using FLIPR$^{384}$—Calcium FLUO-4-AM Tags

Cells are plated at 30K cells/50 uL media/well in PDL-coated 384-well plate (Greiner Cell Coat; VWR cat#82051-358) 24 hours before experiment. 20 µM Fluo-4-AM (Invitrogen cat#F-14201) are prepared, resuspended with 10 µl F-127, 20% pluronic solution in DMSO (Invitrogen cat#P3000MP), and added to 2.3 mL culture medium. Cells are loaded with dye by adding 5 µl of the 20 µM Fluo-4-AM solution to each well of the 384-well plate that already contained 50 µL of culture medium. The plates are kept in dark, RT, for approximately 1 hour. HBSS/1% HEPES/0.2 g/L MgCl$_2$ was prepared and cells transferred to a plate washer to remove dye-loading solution from cells. The cells are washed with HBSS/1% HEPES/0.2 g/L MgCl$_2$, being careful not to dislodge the cells. The final volume of buffer left on the cells should equal 40 µL. The cell plate is transferred to FLIPR monitoring instrument (Molecular Devices, Sunnyvale, Calif.), and 10 µL compound is added and incubated for 30 minutes. Data points (1/sec) are acquired prior to the addition of CaCl$_2$ to establish basal readings. 5 µL 11 mM CaCl$_2$ (1.0 mM CaCl$_2$ final) is added, and the fluorescence read every second for 1 minute, then every 10 seconds for 14 minutes. At the end of the experiment, 10 µL 1% Trition-X100 (prepared in 10 mM HEPES) are added to lyse cells to obtain a $F_{max}$ value, and incubated 10-15 min to visually confirm cell lysis A platewide FLIPR measurement is performed to obtain the Fmax value.

Figure 9:
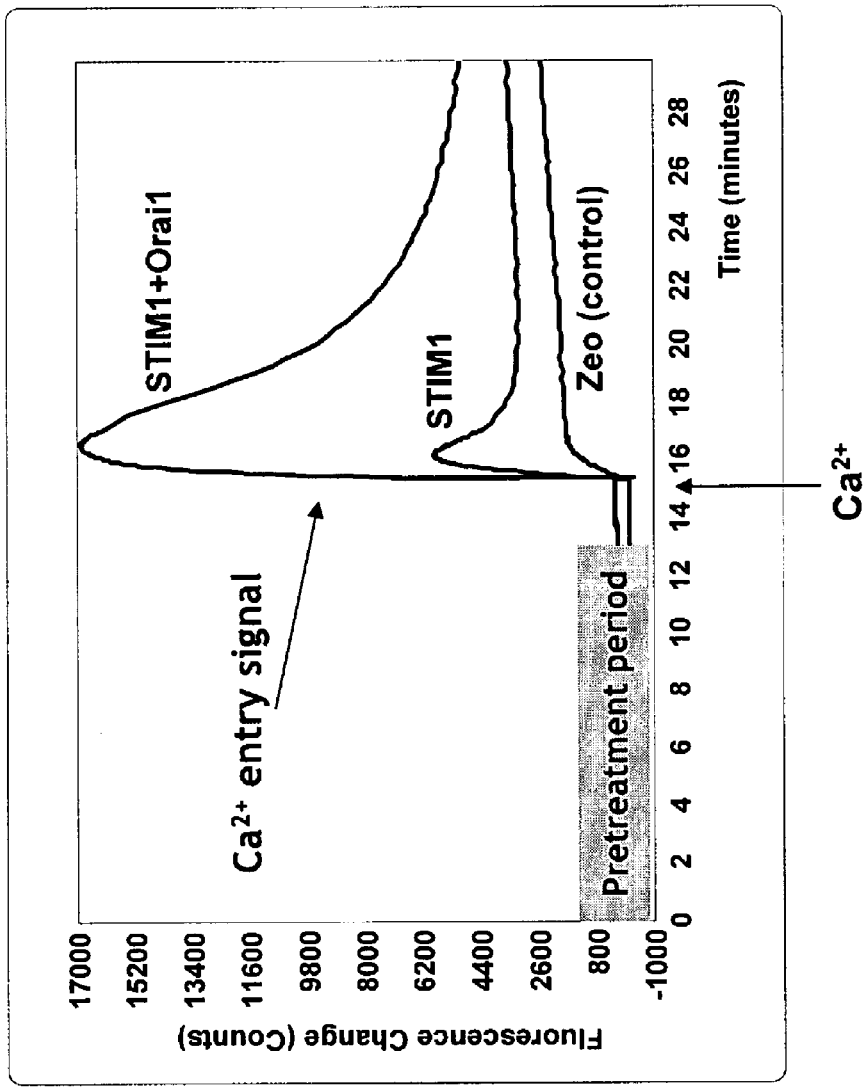
FIG. 9 depicts an enhanced calcium entry signal of human cells stably co-expressing hSTIM1 and hOrai1 in FLIPR assay, as compared to cells stably expressed with STIM1 alone.
Figure 10:
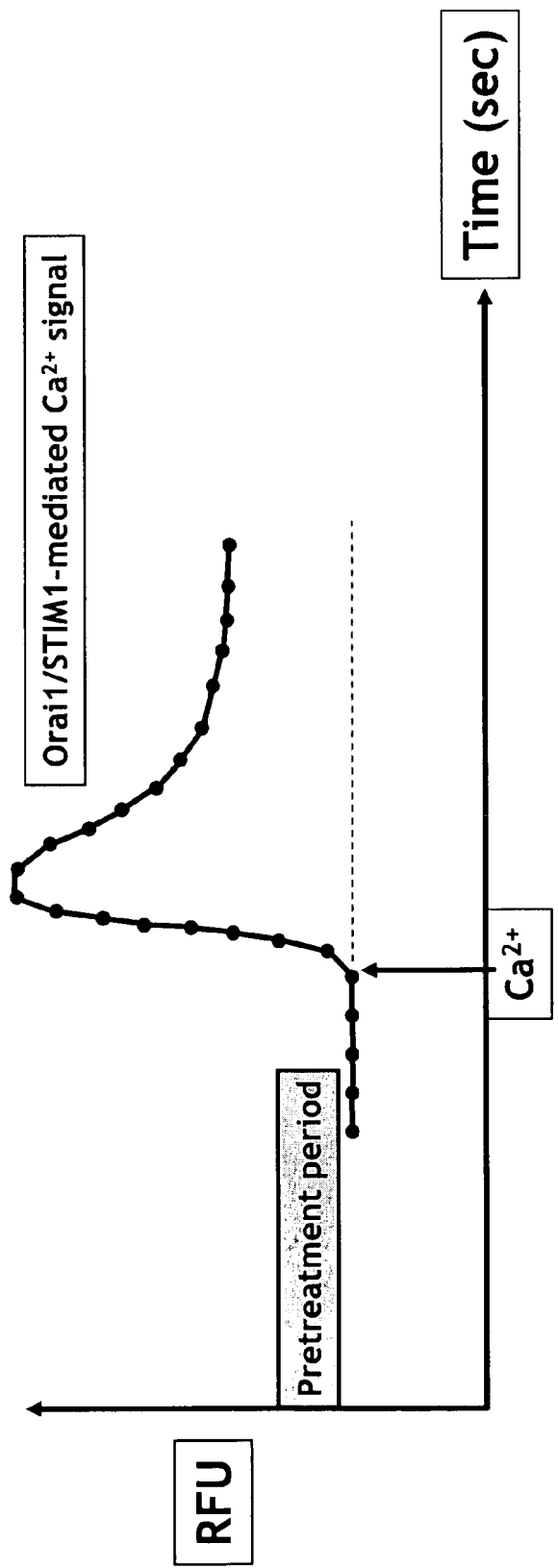
FIG. 10 depicts an Orai1/STIM1-mediated $Ca^{2+}$ signal to allow analysis of agents on CRAC channel function.

FLIPR$^{384}$ analysis of stably transfected Jurkat T-cells demonstrates the enhanced Ca$^{2+}$ entry signal of hSTIM1 and hOrai1 as compared to cells stably transfected with hSTIM1 alone. See FIG. 9. Stable transfection of STIM1 alone increased levels to approximately 2-fold, in contrast to the 9-fold increase with stably co-transfected hSTIM1 and hOrai1. Moreover, as seen in FIG. 10, the RFU (relative fluorescent unit) mapped over time allows the assay to map and detect multiple parameters that define CRAC-channel mediated Ca$^{2+}$ entry.

Example 5

In Vitro Screening for Agents that Modulate Intracellular Calcium Levels

Fluorescence-based assays are used for screening the compounds described herein, which modulate intracellular calcium.

A. Assay Protocol

RBL-2H3 cells plated in 384-well plates are loaded for 45 min with FLUO-4-AM (2 µM final concentration) in a Hanks-buffered salt solution. Cells are washed and placed in a nominally Ca$^{2+}$- and Mg$^{2+}$-free Hanks solution. One minute later, a test agent or vehicle is added. After a 15 minute incubation period, 1 µM thapsigargin (Tg) is added to inhibit the ER Ca$^{2+}$ pump and discharge intracellular Ca$^{2+}$ stores. Fifteen minutes after addition of Tg, store-operated calcium entry is initiated by adding external Ca$^{2+}$ to a final concentration of 1.8 mM and the cells monitored for a further 10-15 minutes. Calcium levels are monitored throughout the assay using a FLIPR$^{384}$ (Molecular Devices fluorimetric imaging plate reader for high throughput screening).

In an alternative screening assay procedure, one minute after washing out the FLUO-4-AM, 1 µM Tg is added to the S1-SY5Y cells. Fifteen minutes after addition of Tg, test compound or vehicle is added, followed by another 15 minute incubation in Ca$^{2+}$-free buffer. Store-operated calcium entry is then initiated by adding external Ca$^{2+}$ to a final concentration of 1.8 mM and the response monitored for a further 10-15 minutes.

A similar screening assay procedure is used with HEK293 and RBL-2H3 cells.

The screening assay alternatively uses external $Ba^{2+}$ (final concentration of 10 mM) in place of external $Ca^{2+}$. In this case, thapsigargin-induced store-operated $Ba^{2+}$ entry serves as a surrogate for store-operated $Ca^{2+}$ entry.

B. Data Analysis

The kinetic data from the FLIPR[384] are analyzed and stored in a relational database (ActivityBase; IDBS). Ten quantitative parameters are calculated that define various aspects of the store-operated calcium entry response. These parameters are as follows:

Mean Basal: basal fluorescence (relative fluorescence units, RFU) readings averaged over 30 seconds prior to addition of $Ca^{2+}$ to initiate store-operated calcium entry.

Up slope: linear regression of the increase in RFU from 2 to 30 sec after addition of $Ca^{2+}$.

Up rate constant (Up K): the rate constant derived from first-order association of RFUs from 2 seconds to peak response.

Peak: the peak RFU (single point) achieved after addition of $Ca^{2+}$.

Time to peak: the time at which the peak RFU is achieved.

Peak/Basal: the difference between peak and mean basal RFU.

Decay slope: linear regression of the decrease in RFU from the peak to the end of the measurement period.

Decay rate constant (Decay K): the rate constant derived from first-order decay of RFUs from the peak to the end of the measurement period.

Area under the curve (AUC): area under the curve from the addition of $Ca^{2+}$ to the end of the measurement period.

Combinations of these parameters are used to characterize the compounds capable of modulating intracellular calcium levels. Compounds are retested under identical conditions to confirm their activity. Compounds with confirmed activity are then analyzed for concentration-dependent effects, and subsequently, those compounds displaying concentration-dependent effects are categorized as compounds that modulate intracellular calcium.

Results

Two compounds, Cmpd A and Cmpd B, were found to inhibit CRAC-channel mediated $Ca^{2+}$ entry in stably transfected STIM1/Orai1 cells. Cmpd A and Cmpd B, which was isolated via high throughput screening are both fluorobenzamido compounds, and are represented by the following structures:

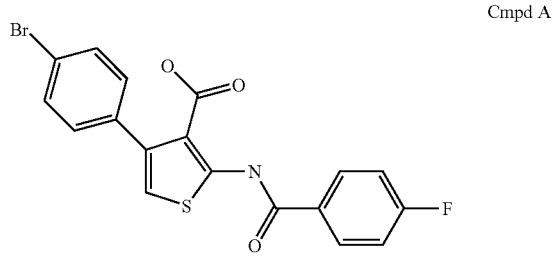

Cmpd A

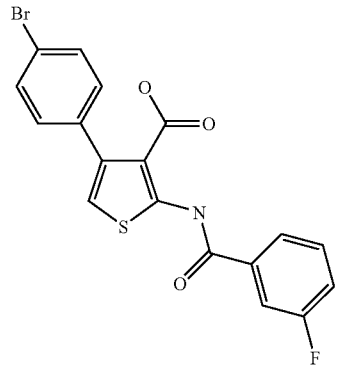

Cmpd B

The $IC_{50}$ for compound A was 3.3 M, with Cmpd B at 1.9 µM, demonstrating the efficacy of inhibiting calcium inflow at low micromolar levels.

Example 6

In Vitro Effects of Agents that Modulate Intracellular Calcium on Degranulation and Cytokine Release in RBL-2H3Cells To assess degranulation and cytokine release, RBL-2H3 cells are plated and stimulated with 20 nM thapsigargin/20 nM TPA for 20 hr in the presence or absence of compounds capable of modulating intracellular calcium levels. Media is collected and assayed for the release of the inflammatory mediator β-hexosaminidase or for the release of the cytokine TNF-α. The β-hexosaminidase enzymatic assay is performed by adding 200 µL1 mM p-nitrophenyl-acetyl-glucosamide substrate (Sigma #N9376) in 0.05M sodium citrate (pH 4.5) to 50 µL of conditioned medium, incubating for 60 min at 37-C, then adding 500 mL 0.05M sodium carbonate, 0.05M sodium bicarbonate pH 10.5, mixing thoroughly, and reading the absorbance at 405 nm in a BioRad plate reader. The TNF-α release assay is performed using the Rat Tumor Necrosis Factor-α Ultrasensitive ELISA Kit from BioSource.

Example 7

Modulation of Intracellular Calcium by a SOCE Inhibitor in STIM1 and Orai1-Overexpressing Cells Store-operated calcium entry is sensitive to the inhibitor 2-aminoethoxydiphenyl borate (2-APB). To test whether the $Ca^{24}$ entry pathway constitutively activated by STIM1 overexpression is pharmacologically similar to endogenous SOCE, HEK[STIM1] cells are pre-incubated with increasing doses of 2-APB and STIM1-induced $Ca^2$ entry is measured. Thapsigargin-mediated store depletion of both HEK-Zeo control cells and HEK[STIM1] cells followed by readdition of external calcium results in inhibition by 2-APB with similar $IC_{50}$ values of 11.8 µM and 10.5 µM, respectively. Treatment of HEK[STIM1] cells with 2-APB and examining calcium entry in the absence of store depletion results in a biphasic effect of 2-APB on calcium entry. The constitutive calcium entry is inhibited with an $IC_{50}$ value of 10.8 µM, similar to that reported for endogenous SOCE. However, at lower concentrations of 2-APB, calcium entry is potentiated. The ability to both potentiate and inhibit calcium entry is a property of 2-APB that has previously been shown to occur with the calcium release activated calcium (CRAC) channel.

Thus, overexpression of STIM1 in HEK293 cells confers a CRAC-like property to constitutive $Ca^{2+}$ entry measured in HEK293 cells. Accordingly, assays to identify agents that modulate intracellular calcium are optionally performed in cells overexpressing STIM1 in the absence of intracellular calcium depletion protocols.

Example 8

In Vitro Effects of Agents that Modulate Intracellular Calcium on IL-2 Secretion from Jurkat T Cells To measure IL-2 secretion from Jurkat T cells, cells are plated in a 96 well plate at a density of $1.5 \times 10^5$ cells/well. Cells are stimulated with 2.5 µg/ml PHA lectin +80 nM TPA for 20 hr in the presence or absence of a compounds capable of modulating intracellular calcium levels. The medium is then collected and analyzed for IL-2 levels by ELISA (BioSource) according to the manufacturer's protocols.

Example 9

Dose-Response Effects of Test Compound, CSA or Rapamycin in Mouse Footpad DTH

Purpose: Determine dose-response effects of Test Compound on mBSA induced DTH response in foot pads when dosing is done during the sensitization as well as induction phase.

Animals: 61 Male Swiss Webster Mice approx. 20-25 grams at start of study.

Materials: Methylated BSA (Sigma) Freund's complete adjuvant (Difco) plus supplemental *M. tuberculosis* H37 RA (Difco).

General Study Design:

Mice are anesthetized with Isoflurane and given intradermal antigen injections of 0.1 ml at the base of the tail (D0, D07). Antigen is prepared by making a 4 mg/ml solution in sterile water. Equal volumes of antigen and Freund's complete adjuvant to which 4 mg/ml MTB are added (sonicate for 5 minutes after adding MTB to oil), are emulsified by hand mixing until a bead of this material holds its form when placed in water. Treatment is initiated on day 0, qd (24 hr intervals) and continued through day 10 when challenge is done.

On day 10 animals are injected into the right hind footpad with 20 µl of 10 mg/ml mBSA. Five unsensitized males are injected with mBSA into the footpad. Twenty-four hours later (day 11) the right and left hind paws are transected at the medial and lateral malleolus and weighed and the weight difference induced by injection of antigen is determined.

Statistical Analysis. Paw weights (mean±SE) for each group are analyzed for differences using a Student's t test or ANOVA with Dunnett's post test. Statistical significance is set at $p \leq 0.05$.

TABLE 5

Treatment Groups Males

| Group | N | Treatment 10 ml/kg qd, po |
|---|---|---|
| 1 | 5 | Normal controls (no sensitization) Inject mBSA into right only |
| 2 | 8 | DTH + Vehicle (70% PEG400/30% Water) |
| 3 | 8 | DTH + Test Compound (50 mg/kg, po, qd) |
| 4 | 8 | DTH + Test Compound (100 mg/kg, po, qd) |
| 5 | 8 | DTH + Test Compound (200 mg/kg, po, qd) |

TABLE 5-continued

Treatment Groups Males

| Group | N | Treatment 10 ml/kg qd, po |
|---|---|---|
| 6 | 8 | DTH + Test Compound (300 mg/kg, po, qd) |
| 7 | 8 | DTH + CSA (100 mg/kg qd, ip) |
| 8 | 8 | DTH + Rapamycin (5 mg/kg qd, ip) |

Example 10

Effect of Test Compound in Rat Collagen Induced Arthritis (CIA) Model

Purpose: Determine efficacy of Test Compound administered by oral dosing qd, in inhibiting the inflammation, cartilage destruction and bone resorption of developing type II collagen arthritis in rats.

Animals: 44 Female Lewis rats (Charles River#7246950), weighing 125-150 g at the start of the study. 40 rats are injected with collagen to get 40 solid responders on days 10, 11 for 4 groups of 10. Four nonimmunized animals serve as normal controls.

Materials: Test Compound (sodium salt), PEG400 as liquid, Type II collagen, Freund's incomplete adjuvant, acetic acid. Test Compound is prepared at a concentration of up to 100 mg/ml in 70% PEG400/30% water. Collagen is prepared by making a 4 mg/ml solution in 0.01 N Acetic acid. Equal volumes of collagen and Freund's incomplete adjuvant, are emulsified by hand mixing until a bead of this material holds its form when placed in water.

General Study Design: Animals (10 rats/group for arthritis, 4 rats/group for normal control).

Animals in groups 2-5 are anesthetized with isoflurane and given collagen injections (D0); each animal gets 300 µl of the mixture spread over 3 subcutaneous sites on the back. On Day 6 (D6) the animals are anesthetized again and given a second collagen injection, as before.

Oral dosing of Test Compound at 24 hour intervals (qd) is initiated on Day 0 using a dose volume of 5 ml/kg for oral solutions. Rats are weighed on Days 0, 3, 6, and 9-17 of arthritis, and caliper measurements of ankles taken every day beginning on Day 9. Final body weights are taken on Day 17 of arthritis. On Day 17, all animals are anesthetized for terminal blood draw and then euthanized. Subsequently, hind paws and knees are removed, the hind paws are weighed and then (with knees) placed in formalin for processing for microscopy. Livers, spleen and thymus and kidneys are also removed, trimmed of extraneous tissue and weighed. Kidneys are retained in formalin for histopathology.

Sampling will occur over 1 day and involves groups 2-5 with samples retained from all groups. This results in all animals being treated similarly and is important for clinical parameters and final liver weights.

Example 11

Effect of Compounds Capable of Modulating Intracellular Calcium Levels on DNBS-Induced Ulcerative Colitis in Rats Procedure: Male Wistar rats weighing 200±20 g are fasted for 24 hours prior to use. Distal colitis is induced by intracolonic instillation of DNBS (2,4-dinotrobenzene sulfonic acid, 20 mg in 0.5 ml ethanol 30%) with a catheter of 12 cm in length, followed by gentle injection of air (2 ml) through the catheter to ensure that the solution remain in the colon. The animals are divided into groups of 5 each. Test substance and vehicle are administered either daily or twice daily by appropriate route of administration 24 hour and 1 hour before DNBS instillation and then for 6 consecutive days thereafter. One normal control group is treated with 0.9% NaCl alone without DNBS challenge. The animals are sacrificed 12 hours after the final bid dose and 24 hours after the final daily dose and the colon is removed and weighed. During the experiment, body weight, fecal occult blood and stool consistency are monitored daily. Furthermore, when the abdominal cavity is opened before removal of the colon, adhesions between the colon and other organs are noted as is the presence of colonic ulceration after removal and weighing of each colon (a macroscopic damage score is recorded according to established score criteria). The colon-to-body weight ratio is calculated according to the formula: Colon (g)/BW×100. The "Net" increase in ratio of Vehicle-control+DNBS group relative to Vehicle-control group is used as a base for comparison with individual treated groups and expressed as "Dec. (%)" (percent decrease). A 30% or more ($\geqq$30%) reduction in colon-to-body weight ratio, relative to the vehicle treated control group, is considered significant.

Sulfasalazine is used the standard test agent. (Hogaboam C M, et al., An orally active non-selective endothelin receptor antagonist, bosentan, markedly reduces injury in a rat model of colitis. *Eur J Pharmacol.* 309: 261-269, 1996; Yue G, et al., In some embodiments, the 21-aminosteroid tirilazid mesylate ameliorates inflammatory bowel disease in rats. *J Pharmacol Exp Ther.* 276: 265-270, 1996.)

The examples and embodiments described herein are for illustrative purposes only and in some embodiments, various modifications or changes are to be included within the purview of disclosure and scope of the appended claims.

What is claimed is:

1. An isolated mammalian cell comprising (a) a stromal interacting molecule (STIM) polypeptide or a polypeptide at least 95% identical to the amino acid sequence of the STIM polypeptide, and (b) an Orai polypeptide or a polypeptide at least 95% identical to the amino acid sequence of the Orai polypeptide, wherein one or both polypeptides are over-expressed.

2. The mammalian cell of claim 1, wherein the Orai polypeptide is Orai1, or a polypeptide at least 95% identical to the amino acid sequence of Orai1 polypeptide.

3. The mammalian cell of claim 1, wherein said STIM polypeptide is STIM1 or STIM2, or a polypeptide at least 95% identical to the amino acid sequence of STIM1 or STIM2 polypeptide.

4. An isolated mammalian cell comprising (a) a stromal interacting molecule (STIM) polypeptide or a polypeptide at least 95% identical to the amino acid sequence of the STIM polypeptide, (b) an Orai polypeptide or a polypeptide at least 95% identical to the amino acid sequence of the Orai polypeptide, wherein one or both polypeptides are recombinant.

5. The mammalian cell of claim 4, wherein both the orai gene and the stim gene are exogenous to the mammalian cell.

6. The mammalian cell of claim 4, wherein said STIM polypeptide is STIM1 or STIM2, or a polypeptide at least 95% identical to the amino acid sequence of the STIM1 or STIM2 polypeptide.

7. The mammalian cell of claim 4, wherein the Orai polypeptide is Orai1, or a polypeptide at least 95% identical to the amino acid sequence of the Orai1 polypeptide.

* * * * *

```
                            SEQUENCE LISTING

<160> NUMBER OF SEQ ID NOS: 24

<210> SEQ ID NO 1
<211> LENGTH: 6
<212> TYPE: PRT
<213> ORGANISM: Artificial Sequence
<220> FEATURE:
<223> OTHER INFORMATION: Description of Artificial Sequence:  Synthetic
      6x His tag

<400> SEQUENCE: 1

His His His His His His
  1               5

<210> SEQ ID NO 2
<211> LENGTH: 46
<212> TYPE: DNA
<213> ORGANISM: Artificial Sequence
<220> FEATURE:
<223> OTHER INFORMATION: Description of Artificial Sequence:  Synthetic
      primer

<400> SEQUENCE: 2
gaattaatac gactcactat agggagaata cgaatgtacc accggg                    46

<210> SEQ ID NO 3
<211> LENGTH: 48
<212> TYPE: DNA
<213> ORGANISM: Artificial Sequence
<220> FEATURE:
<223> OTHER INFORMATION: Description of Artificial Sequence:  Synthetic
      primer

<400> SEQUENCE: 3
gaattaatac gactcactat agggagacca agtgatgcta gacaatgt                  48

<210> SEQ ID NO 4
<211> LENGTH: 39
<212> TYPE: DNA
<213> ORGANISM: Artificial Sequence
<220> FEATURE:
<223> OTHER INFORMATION: Description of Artificial Sequence:  Synthetic
      primer

<400> SEQUENCE: 4
ctgaacatga agcggccgca tcatgtctgt gtggaccac                            39
```

```
<210> SEQ ID NO 5
<211> LENGTH: 32
<212> TYPE: DNA
<213> ORGANISM: Artificial Sequence
<220> FEATURE:
<223> OTHER INFORMATION: Description of Artificial Sequence:  Synthetic
      primer

<400> SEQUENCE: 5
gctgaactcg agctagacaa tgtccccgga tg                                       32

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence:  Synthetic
      primer

<400> SEQUENCE: 6
gaaagagtat gagtcccagc                                                     20

<210> SEQ ID NO 7
<211> LENGTH: 22
<212> TYPE: DNA
<213> ORGANISM: Artificial Sequence
<220> FEATURE:
<223> OTHER INFORMATION: Description of Artificial Sequence:  Synthetic
      primer

<400> SEQUENCE: 7
ccaacaattc gggcctagag ac                                                  22

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence:  Synthetic
      primer

<400> SEQUENCE: 8
gtaggtgggc gagtggagat c                                                   21

<210> SEQ ID NO 9
<211> LENGTH: 22
<212> TYPE: DNA
<213> ORGANISM: Artificial Sequence
<220> FEATURE:
<223> OTHER INFORMATION: Description of Artificial Sequence:  Synthetic
      primer

<400> SEQUENCE: 9
cagtggaagt gttcaggatc gc                                                  22

<210> SEQ ID NO 10
<211> LENGTH: 23
<212> TYPE: DNA
<213> ORGANISM: Artificial Sequence
<220> FEATURE:
<223> OTHER INFORMATION: Description of Artificial Sequence:  Synthetic
      primer

<400> SEQUENCE: 10
ccacatccat tgccttcaat gag                                                 23

<210> SEQ ID NO 11
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
ctcgcctaga cttatgtgac                                              20

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
ccagtagacc catcaaagtg                                              20

<210> SEQ ID NO 13
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
ctacggaggc gaacgaacg                                               19

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
ggcgattgtt catggaaagg                                              20

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
cgatatccgt atcacccaca                                              20

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
ctcaccgaac tcgtccagtt                                              20

<210> SEQ ID NO 17
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 17
cgcttccatt ccgactagtt                                                 20

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
gcttctccag ttttgcgtag                                                 20

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
gaaatgcgga cctggagagt                                                 20

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
cgacttcttg agagcatcga                                                 20

<210> SEQ ID NO 21
<211> LENGTH: 1497
<212> TYPE: DNA
<213> ORGANISM: Homo sapiens

<400> SEQUENCE: 21
agcggcgccg cgggcctgcg tgctggggca gcgggcactt cttcgacctc gtcctcctcg     60
tcctgtgcgg ccggccgggt gaggccgggc ccgcgtaggg ggcagtcggc ggctgcctcc    120
ggcggaggtg cctcgcggcg cccgggccgg cccgcgcctc ggcggcgtgc tccatgcatc    180
cggagcccgc cccgcccccg agccgcagca gtcccgagct tcccccaagc ggcggcagca    240
ccaccagcgg cagccgccgg agccgccgcc gcagcgggga cggggagccc cggggggccc    300
cgccaccgcc gccgtccgcc gtcacctacc cggactggat cggccagagt tactccgagg    360
tgatgagcct caacgagcac tccatgcagg cgctgtcctg gcgcaagctc tacttgagcc    420
gcgccaagct taaagcctcc agccggacct cggctctgct ctccggcttc gccatggtgg    480
caatggtgga ggtgcagctg gacgctgacc acgactaccc accggggctg ctcatcgcct    540
tcagtgcctg caccacagtg ctggtggctg tgcacctgtt tgcgctcatg atcagcacct    600
gcatcctgcc caacatcgag gcggtgagca acgtgcacaa tctcaactcg gtcaaggagt    660
ccccccatga gcgcatgcac cgccacatcg agctggcctg ggccttctcc accgtcatcg    720
gcacgctgct cttcctagct gaggtggtgc tgctctgctg ggtcaagttc ttgcccctca    780
```

| | | |
|---|---|---|
| agaagcagcc aggccagcca aggcccacca gcaagccccc cgccagtggc gcagcagcca | 840 | |
| acgtcagcac cagcggcatc accccgggcc aggcagctgc catcgcctcg accaccatca | 900 | |
| tggtgccctt cggcctgatc tttatcgtct tcgccgtcca cttctaccgc tcactggtta | 960 | |
| gccataagac tgaccgacag ttccaggagc tcaacgagct ggcggagttt gcccgcttac | 1020 | |
| aggaccagct ggaccacaga ggggaccacc ccctgacgcc cggcagccac tatgcctagg | 1080 | |
| cccatgtggt ctgggccctt ccagtgcttt ggccttacgc ccttcccctt gaccttgtcc | 1140 | |
| tgccccagcc tcacgacag cctgcgcagg gggctgggct tcagcaaggg gcagagcatg | 1200 | |
| gagggaagag gatttttata agagaaattt ctgcactttg aaactgtcct ctaagagaat | 1260 | |
| aagcatttcc tgttcttcca gctccaggtc cacctcctgt tgggaggcgg tggggggcca | 1320 | |
| aagtggggcc acacactcgc tgtgtcccct ctcctcccct gtgccagtgc cacctgggtg | 1380 | |
| cctcctcctg tcctgtccgt ctcaacctcc ctcccgtcca gcattgagtg tgtacatgtg | 1440 | |
| tgtgtgacac ataaatatac tcataaggaa aaaaaaaaa aaaaaaaaaa aaaaaaa | 1497 | |

<210> SEQ ID NO 22
<211> LENGTH: 2495
<212> TYPE: DNA
<213> ORGANISM: Homo sapiens

<400> SEQUENCE: 22

| | | |
|---|---|---|
| ggagagcctg agttggcatt cgtataaatg acctgcctgg ctcccaccat gagtgctgag | 60 | |
| cttaacgtgc ctatcgaccc ctctgctcct gcctgccctg agccaggcca taagggcatg | 120 | |
| gattaccggg actgggtccg ccgcagctac ctggaactgg tcacctctaa ccaccactcg | 180 | |
| gtacaggccc tgtcgtggcg gaagctctac ctgagcaggg ccaagctgaa ggcctccagc | 240 | |
| aggacctccg ccctcctctc cggctttgcc atggtggcca tggtggaggt gcagctggag | 300 | |
| acgcagtacc agtacccgcg gccgctgctg attgccttca gcgcctgcac cacggtgctg | 360 | |
| gtggccgtgc acctgttcgc cctcctcatc agcacctgca tcctgcccaa tgtggaggcc | 420 | |
| gtgagcaaca tccacaacct gaactccatc agcgagtccc cgcatgagcg catgcacccc | 480 | |
| tacatcgagc tggcctgggg cttctccacc gtgcttggca tcctactctt cctggccgag | 540 | |
| gtggtgctgc tctgctggat caagttcctc cccgtggatg cccggcgcca gcctggcccc | 600 | |
| ccacctggcc ctgggagtca cacgggctgg caggccgccc tggtgtccac catcatcatg | 660 | |
| gtgcccgtgg gcctcatctt cgtggtcttc accatccact tctaccgctc cctggtgcgc | 720 | |
| cacaaaacgg agcgccacaa ccgcgagatc gaggagctcc acaagctcaa ggtccagctg | 780 | |
| gacgggcatg agcgcagcct gcaggtcttg tgagggccg agggccgggg ctgggagcgg | 840 | |
| ccctgtgccc gggagtccgc agaggcgggg atttgtcaga tgcagacatt ttgcaaggct | 900 | |
| gccgggtagt tcaagaccaa agttttcctc ttgtcttaat accataagga ctggatgact | 960 | |
| tctcctgaga tagaaccgtt tggttcaatg agggactgtg ttgctaagag cgttggggc | 1020 | |
| aaagccaggc tggttccttg gcctcggggt ttcctgggtc ggggacacgg tgaagaggct | 1080 | |
| ccagcgggac ctgccatca gtcctgggcc aggaggggct ccaagcagca cccagcggtc | 1140 | |
| cgggggagtc tcagacccgg catgcgtggc tggcagacct gggagagcca ggcagggtt | 1200 | |
| ttgcgttcag agaaggattg ccccagagac ccgtggtgga cttcatgggt gctgagtggc | 1260 | |
| ccgtgtgaca gtgatgacac gaaggcttcg gcgtttgagt gggtgcaggt gcacgccagg | 1320 | |
| gcttggtgct tccctgcctg gcctggagg gagctgggtg gcctggcttc agggggaagac | 1380 | |
| aggagccagg acacacgtca gcccagcagg tgtgggggt gctgcagccc tcggcagtgg | 1440 | |

```
ggtcaggccc tggggatgt ttccaatggt gggcagcctg gccaggccgg agaagacatg    1500
ttcacgggca tctatcagat gccccttga ggaggctgag ttatttgagg gctgctgcaa    1560
agtacgctag gctcaaattc tcttttccca gccagagccc tggccacacg gactcagagg    1620
ggccaccggg gtggggaaag gaccctccc cgacccccg cagccactgg cctccagctc    1680
tcggccacag aatggcctct aaggctgact cagccgctcc cttgggctgt ggcagcagga    1740
ggcgggggct ctggctcagg ccccggagcc tgtgcagctt gcccatggcc ctaggcagcg    1800
aggggacagc ctgggggact tcctgcctag gcaaggtcat tggccgggcc tggcctgtgg    1860
atagtggggc caggggccgg cccaggccaa atgagtgccc tccttgttat gacaccaagt    1920
gactacaagg gaggcaagac ccctccaggc ctctcagccg acactgggtc ccaccacaca    1980
cagtgactgt gccgtgcagt gcaggttctg gccttttcct tgaaggcatc tggtagaccc    2040
gaagccacgc tctcgggccg cacatgcacg ccgcagcacc agctgccctg agctgcttgt    2100
acaaccaaac acctttcccc tcttctccag ctgtaacctg gagagtcagc catgccttgt    2160
cttttgttct cataaatagt cactggggcc gggcgcagtg actcacgcct gtaatcccag    2220
cactttggga ggcctaggtg gcggatcac ttgaggtcag gagttcgaga ccagcctggc    2280
caacatggtg aaaccctgtc tctactaaaa aaatacagaa aattagctgg gcgtggtggc    2340
gggcgcctgt agccccagct acttgggagg ctgaggtggg agaatggcaa tggcgtgaac    2400
ccgggaggca gagcttgcag tgagctgaga tggcgccact gcactccagc ctgggcgaca    2460
gagccagact caatctcaaa aaaaaaaaaa aaaaa                                2495

<210> SEQ ID NO 23
<211> LENGTH: 2239
<212> TYPE: DNA
<213> ORGANISM: Homo sapiens

<400> SEQUENCE: 23
cgctccggct cctggggctc cccgcagacg ctgcttttct tgctccactg ggggtgcctc      60
ttcctgggcg cccgccgcct gcatcctgct cgccctgtct gggaatgggg ccgccccgg    120 gcttgggccg gccggctgg gccccgag gcgcttccgc cccgtagtga ccgcctggtg      180
ccgccccccc ccaggatgaa gggcggcgag ggggacgcgg gcgagcaggc cccgctgaac    240
cctgagggcg agagccctgc aggctcggcc acgtaccggg agttcgtgca ccgcggctac    300
ctggacctca tgggggccag tcagcactcg ctgcgggcgc tcagctggcg ccgcctctac    360
ctcagccggg ccaagctcaa agcttccagc cgcacgtctg ccttgctctc gggcttcgcc    420
atggtggcca tggtggaggt gcagctggag agtgaccacg agtacccacc aggcctgctg    480
gtggccttca gtgcctgcac caccgtgctg gtggctgtgc acctcttgc actcatggtc    540 tccacgtgtc tgctgcccca cattgaagct gtgagcaaca tccacaacct caactctgtc    600
caccagtcgc cacaccagag actgcaccgc tacgtggagc tggcctgggg cttctccact    660
gccctgggca ccttctctctt ccttgctgaa gttgtcctgg ttggttgggt caagtttgtg    720
cccattgggg ctcccttgga cacaccgacc ccatggtgc ccacatcccg ggtgcccggg    780
actctggcac cagtggctac ctcccttagt ccagcttcca atctcccacg gtcctctgcg    840
tctgcagcac cgtcccaggc tgagccagcc tgcccacccc ggcaagcctg tggtggtggt    900
ggggcccatg ggccaggctg gcaagcagcc atggcctcca cagccatcat ggtacccgtg    960
gggctcgtgt ttgtggcctt tgccctgcat ttctaccgct ccttggtggc acacaagaca   1020
gaccgctaca gcaggaact agaggaactg aatcgcctgc agggggagct gcaggctgtg   1080
```

-continued

```
tgagactggt gttagccacc gctcactgca agcactgcct ccctccgggg tctgtaagag   1140
gccgcagggg cctacagacc tcatccccc atccctggc tggagccact tccagtggcc    1200
actctcaggc agagttcaga ttcctgcccg cagggtcctc tgggctggc cttggggcag   1260 ctcccacatt cccagggatt ttccccatca gtctgtccct tgggttttgc aagctactct   1320
gcacctgggc tggcctcagt tgaaggatca tgcagtagat agaggggagg cagggagagc   1380
ttgtgggacc ttcagtgctg actttagcca ccatttccat tcctatacag gatgtgaagg   1440
tcagaaggca gccaattgtt ggtttaattt ttttttttt tgagacagtc tgtttcccag    1500
gctggagtgt agtgatacag tcacagctca ctgtagcctc gaccttccag gctcaaaaga   1560
tgctcccacc acagcctccc aggtagtgag tagctggtac tacaggtgtg tgctgccaca   1620
cccgactaat ttttttgtag acgggggtt tcgctgttcc caggctggtc tcaaactcct    1680
gggctcaagt gaacctcccg cctcggcctc ccaaagtgct gggattcctt tctttatttc   1740
tgtagaatct attttatggt tggcattttg ggggaagatt tcgatgggtt ccacattctt   1800
gctttagttg ttgtagaggg atttgggtgt ttctacccaa ggcattggtc tagcttttcc   1860
tacaatgaac ctatctttgg aggtttaagc tccccaccctt ccccactgt ggtgacctgt   1920 ggccacttgc agaagggatg gtgcctgacc cactgcccta gccccacgct atgcaccaaa   1980
cttgttctcc ccgtcctggt ccagggctgg ggtcttaga gactgacagc ctctgcccca    2040
ggcctgagtc cttagcaagg gttgggtaag gaggttttaa gggagaaggt ccagtcctta   2100
gcccttgaaa tacaaagctc ttctgacact gaatttggat gcaccttgtt ttatataata   2160
aatcgtgttt cacagaaaaa aaaaaaaaaa aaaaaaaaaa aaaaaaaaaa aaaaaaaaaa   2220
aaaaaaaaaa aaaaaaaaa                                                2239
```

<210> SEQ ID NO 24
<211> LENGTH: 1065
<212> TYPE: DNA
<213> ORGANISM: Drosophila melanogaster

<400> SEQUENCE: 24

```
atcatgtctg tgtggaccac ggccaacaat tcgggcctag agacgccaac aaagtcgccg     60
atcacgtcgt cggttccgcg ggcatcgaga agttctgcgg tgatcaccac tggaaatcac    120
cagcagcacc acttccagca cgttgtggcc gccgccgttg cagccgccac ttcagtggcc    180
accggtcatc agttccagca gcagttcccg ctgcacgcac atccgcatcc gcatccacag    240
caccacagca acagtcccac gggtagcggc agcaacagca acaacagcgc aggtttccag    300
cgcaccagca tcagcaactc gctgctgcag ttcccgccgc cccgcccccc ttcctcacag    360
aaccaggcga agccgcgcgg acaccatcgc accgccagca gcagcatgtc gcaatccggc    420
gaggatctcc actcgcccac ctacctgtcc tggcggaagc tccagcttag tcgggccaag    480
ctaaaggcat ccagcaagac gtccgccctg ctctccggat tcgccatggt ggcgatggtg    540
gaggtgcaac tggatcacga tacgaatgta ccaccgggca tgctgatagc cttcgccatc    600
tgcaccaccc tcctggtggc ggtgcacatg ctggccctga tgatcagcac ctgtatcctg    660
ccaaatattg agacggtgtg taatttgcat agtatttccc tggtccacga atcgccacac    720
gagcgtctcc attggtacat tgaaacggcg tgggcattct ccacgctgct gggactcata    780
ctctttctac tggagatagc catcctgtgc tgggtgaaat tctatgacct aagtccgccg    840
gcggcttggc cagcgtgtgt ggtcctcata ccggtgatga tcatctttat ggccttcgcc    900
attcacttct atcgctccct ggtgtcgcac aaatatgagg tgacagtctc gggcattcgt    960
```

```
gagctggaga tgctcaagga gcagatggag caggatcatt tggagcatca caataacata    1020
cgaaataatg gcatgaacta tggcgcatcc ggggacattg tctag                    1065
```